(12) United States Patent
Choi et al.

(10) Patent No.: US 12,071,357 B2
(45) Date of Patent: Aug. 27, 2024

(54) STERILIZATION MODULE AND WATER PURIFYING DEVICE INCLUDING SAME

(71) Applicant: Seoul Viosys Co., Ltd., Ansan-si (KR)

(72) Inventors: Jae Young Choi, Ansan-si (KR); Woong Ki Jeong, Ansan-si (KR); Kyu Won Han, Ansan-si (KR); Yeo Jin Yoon, Ansan-si (KR)

(73) Assignee: Seoul Viosys Co., Ltd., Ansan-si (KR)

( * ) Notice: Subject to any disclaimer, the term of this patent is extended or adjusted under 35 U.S.C. 154(b) by 0 days.

(21) Appl. No.: 18/373,283

(22) Filed: Sep. 27, 2023

(65) Prior Publication Data
US 2024/0025770 A1   Jan. 25, 2024

Related U.S. Application Data

(63) Continuation of application No. 16/604,817, filed as application No. PCT/KR2018/004357 on Apr. 13, 2018, now Pat. No. 11,939,239.

(30) Foreign Application Priority Data

Apr. 14, 2017   (KR) .................. 10-2017-0048815
Sep. 29, 2017   (KR) .................. 10-2017-0126855

(51) Int. Cl.
    *C02F 1/32*   (2023.01)
(52) U.S. Cl.
    CPC ........ *C02F 1/325* (2013.01); *C02F 2201/322* (2013.01); *C02F 2303/04* (2013.01)
(58) Field of Classification Search
    CPC .............. C02F 1/325; C02F 2201/322; C02F 2303/04; C02F 2201/3227; C02F 2201/3228; C02F 1/32; C02F 2201/3222
    See application file for complete search history.

(56) References Cited

U.S. PATENT DOCUMENTS

| 4,535,247 A | 8/1985 | Kurtz |
| 5,861,123 A | 1/1999 | Schifftner |

(Continued)

FOREIGN PATENT DOCUMENTS

| KR | 10-2009-0081658 | 7/2009 |
| KR | 20-0468497 | 8/2013 |

(Continued)

OTHER PUBLICATIONS

Non-Final Office Action dated Dec. 22, 2021, issued to U.S. Appl. No. 16/604,817.

(Continued)

*Primary Examiner* — David A Vanore
(74) *Attorney, Agent, or Firm* — Oblon, McClelland, Maier & Neustadt, L.L.P.

(57) ABSTRACT

A light emitting module including a light source configured to irradiate ultraviolet light, a board on which the light source is disposed, a tube accommodating the board and including a transparent region to transmit the ultraviolet light emitted from the light source, a first base coupled to one side of the tube, a second base coupled to the other side of the tube, a fixation groove disposed in the tube and connected to at least one of the first and second bases, in which the board is coupled to be inserted into the fixation groove, and the fixation groove is spaced apart from a center of the first base when viewed in a cross-section perpendicular to a length direction of the tube.

20 Claims, 42 Drawing Sheets

(56) References Cited

U.S. PATENT DOCUMENTS

| | | |
|---|---|---|
| 10,197,254 B2 | 2/2019 | Crandell et al. |
| 10,458,638 B1 | 10/2019 | Tirosh |
| 2004/0112813 A1 | 6/2004 | Sawada |
| 2005/0082235 A1 | 4/2005 | Bernstein et al. |
| 2007/0267356 A1 | 11/2007 | Wong |
| 2008/0035581 A1 | 2/2008 | Kuhlmann et al. |
| 2008/0095661 A1 | 4/2008 | Kohler |
| 2010/0170857 A1 | 7/2010 | Williams et al. |
| 2011/0203515 A1 | 8/2011 | Krautter |
| 2011/0297844 A1 | 12/2011 | Vecziedins et al. |
| 2012/0169234 A1 | 7/2012 | Shew |
| 2012/0306342 A1 | 12/2012 | Dellian et al. |
| 2013/0148349 A1 | 6/2013 | Pasqualini et al. |
| 2014/0202948 A1 | 7/2014 | Li |
| 2015/0125355 A1 | 5/2015 | Lee et al. |
| 2015/0274549 A1 | 10/2015 | Hwang et al. |
| 2015/0336810 A1 | 11/2015 | Smetona et al. |
| 2015/0344329 A1 | 12/2015 | Smetona et al. |
| 2015/0360924 A1 | 12/2015 | Orita |
| 2016/0107904 A1 | 4/2016 | Rajagopatan et al. |
| 2016/0213444 A1 | 7/2016 | Kiremitci |
| 2018/0055960 A1 | 3/2018 | Reiber et al. |
| 2018/0086649 A1 | 3/2018 | Hayasi et al. |
| 2018/0112836 A1 | 4/2018 | Reider et al. |
| 2019/0142987 A1 | 5/2019 | Zhang et al. |
| 2019/0234564 A1 | 8/2019 | Han |

FOREIGN PATENT DOCUMENTS

| | | |
|---|---|---|
| KR | 10-2015-0115171 | 10/2015 |
| KR | 10-1601390 | 3/2016 |
| KR | 10-2016-0062921 | 6/2016 |

OTHER PUBLICATIONS

Final Office Action dated May 12, 2022, issued to U.S. Appl. No. 16/604,817.
Non-Final Office Action dated Nov. 15, 2022, issued to U.S. Appl. No. 16/604,817.
Notice of Allowance dated May 9, 2023, issued to U.S. Appl. No. 16/604,817.
International Search Report mailed Nov. 8, 2018, in International Application No. PCK/KR2018/004357 (with English Translation).

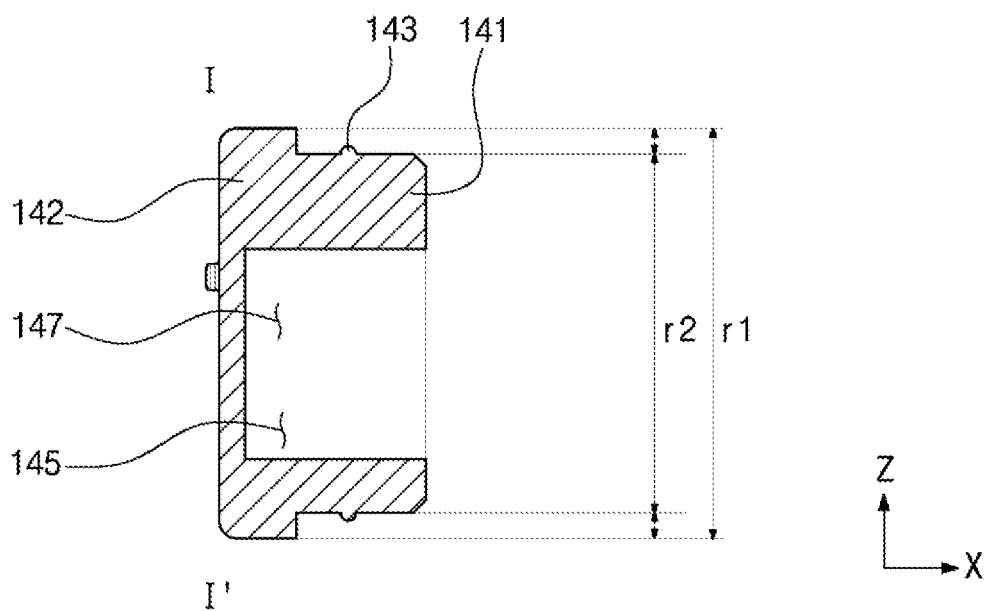

STERILIZATION MODULE AND WATER PURIFYING DEVICE INCLUDING SAME

CROSS-REFERENCE TO RELATED APPLICATIONS

This application is a Continuation of U.S. patent application Ser. No. 16/604,817, filed on Jan. 17, 2020, which is a National Stage Entry of International Application No. PCT/KR2018/004357, filed on Apr. 13, 2018, which claims priority from and the benefit of Korean Patent Application No. 10-2017-0048815, filed on Apr. 14, 2017, and Korean Patent Application No. 10-2017-0126855, filed on Sep. 9, 2017, each of which is hereby incorporated by reference for all purposes as if fully set forth herein.

BACKGROUND

Field

Exemplary embodiments relate to a sterilization module and a water purification device including the same.

Discussion of the Background

Ultraviolet (UV) light has different features depending on its wavelength, and is being applied to a sterilization device to utilize varying features of UV light depending on its wavelength. In general, a mercury (Hg) lamp is used in the sterilization device using UV light. Sterilization may take place using ozone ($O_3$) generated by the mercury lamp. However, because the mercury (Hg) lamp includes mercury inside, the environment may be polluted as the usage time increases.

The sterilization device using various UV rays has been recently developed and provided. Furthermore, objects to be sterilized have been also varied. As such, a sterilization device is embedded in a specific device, such as a refrigerator, washing machine, a humidifier, a water purifier, or the like.

The above information disclosed in this Background section is only for understanding of the background of the inventive concepts, and, therefore, it may contain information that does not constitute prior art.

SUMMARY

Sterilization module constructed according to exemplary embodiments of the invention are capable of improving sterilization efficiency and waterproof performance.

Additional features of the inventive concepts will be set forth in the description which follows, and in part will be apparent from the description, or may be learned by practice of the inventive concepts.

A sterilization module according to an exemplary embodiment includes a light source configured to irradiate ultraviolet light, a board on which the light source is mounted, a protective tube accommodating the board therein and configured to transmit ultraviolet light irradiated from the light source, a first base coupled to one side of the protective tube, and a second base coupled to the other side of the protective tube, in which at least one of the first base and the second base includes an insertion part to be inserted into the protective tube, the insertion part having a first diameter when viewed in a first cross-section perpendicular to a length direction of the protective tube, and a cover part integrally formed on the insertion part and having a second diameter greater than the first diameter in the first cross-section.

The insertion part may include a protrusion that protrudes from an outer peripheral surface of the insertion part to have an O-ring shape, and a diameter of an outer peripheral surface of the protrusion may be equal to or greater than a diameter of an inner peripheral surface of the protective tube.

The second diameter may be the same as a diameter of an outer peripheral surface of the protective tube.

A difference between the second diameter and the first diameter may be the same as a thickness of the protective tube.

The insertion part may include a fixation groove recessed from a surface of the insertion part, and into which the board is to be inserted and fixed, and a receiving groove recessed from the surface of the insertion part, and connected to the fixation groove.

The insertion part may further include a withdrawal groove recessed from the surface of the insertion part and connected to the fixation groove, the cover part may have at least one through-hole, and the withdrawal groove may be connected to the at least one through-hole.

The fixation groove may include a first fixation groove, into which one side surface of the board is to be inserted and fixed, and a second fixation groove, into which the other side surface of the board is to be inserted and fixed.

A depth at which the first fixation groove and the second fixation groove is recessed from the surface of the insertion part may be shorter than a depth at which the receiving groove is recessed from the surface of the insertion part.

The one side surface and the other side surface of the board may be respectively connected to the first fixation groove and the second fixation groove, and the board and an inner side surface of the cover part may be spaced apart by a predetermined distance.

The sterilization module may further include a connector electrically connected to the light source, in which a wire connected to the connector may be drawn to an outside via the predetermined distance.

A depth at which the withdrawal groove is recessed from the surface of the insertion part may be the same as a depth at which the receiving groove is recessed from the surface of the insertion part.

The cover part may include a first cover part connected to the withdrawal groove and a second cover part connected to the receiving groove, and a length of the second cover part extending along the board in a first direction may be greater than a length in the first direction of the first cover part.

The sterilization module may further include a protrusion formed on the insertion part, in which the protrusion may be formed integrally with the insertion part and the cover part.

A cross-section of the protective tube may be circular or polygonal.

The light source may be formed in plural to emit ultraviolet light in different directions.

At least one of the first base and the second base may further include a coupling part connected to the cover part to be coupled to an external device.

The cover part may have at least one through-hole, and the at least one through-hole may be connected to the receiving groove.

At least one of the first base and the second base may further include a coupling part formed integrally with the cover part and extend along a direction in which the board extends, the cover part may have a through-hole along the direction in which the board extends, and when viewed with respect to an extension surface extending along the board, the extension surface may be positioned between the through-hole and the coupling part.

The sterilization module may further include a connector electrically connected to the light source, in which the connector may be mounted on a back surface of the board, and the light source may be mounted on a front surface of the board.

The sterilization module may further include a connector electrically connected to the light source, in which each of the connector and the light source may be mounted on a front surface of the board.

The connector may be accommodated inside the receiving groove.

A sterilization module according to another exemplary embodiment includes a light source configured to irradiate ultraviolet light, a board having a light emitting surface, on which the light source is mounted, and a back surface opposite to the light emitting surface, a protective tube accommodating the board therein and configured to transmit ultraviolet light irradiated from the light source, and first and second bases respectively provided to both ends of the protective tube, in which one end of the board is coupled to be inserted into the first base and the other end of the board is coupled to be inserted into the second base, and the light emitting surface is spaced apart from a center of each of the first and second bases, when viewed in a first cross-section perpendicular to a length direction of the protective tube.

When viewed in the first cross-section, a longest distance between the light emitting surface and an outer peripheral surface of the first base or the second base may have a value different from a longest distance between the back surface and the outer peripheral surface of the first base or the second base.

When viewed in the first cross-section, the longest distance between the light emitting surface and the outer peripheral surface of the first base or the second base may have a value less than the longest distance between the back surface and the outer peripheral surface of the first base or the second base.

Each of the first base and the second base may include a fixation groove into which each end of the board is to be inserted, and the fixation groove may be spaced apart from a center of each of the first and second base, when viewed in the first cross-section.

The sterilization module may further include a connector provided on the light emitting surface of the board, in which at least one of the first and second base accommodates the connector and has a receiving groove connected to the fixation groove, and the receiving groove may be spaced apart from the center of each of the first and second base, when viewed in the first cross-section.

A sterilization module according to yet another exemplary embodiment includes a light source configured to irradiate ultraviolet light, a board having a light emitting surface, in which the light source is mounted, and a back surface opposite to the light emitting surface, a protective tube accommodating the board therein and configured to transmit ultraviolet light irradiated from the light source, and first and second bases respectively provided to both ends of the protective tube, in which one of both ends of the board are coupled to at least one of the first base and the second base, and the light emitting surface is spaced apart from a center of the protective tube, when viewed in a first cross-section perpendicular to a length direction of the protective tube.

When viewed in the first cross-section, a longest distance between the light emitting surface and the protective tube may have a value different from a longest distance between the back surface and the protective tube.

When viewed in the first cross-section, the longest distance between the light emitting surface and the protective tube may have a value less than the longest distance between the back surface and the protective tube.

A water purification device according to still another exemplary embodiment includes a reservoir storing water, a reservoir cover covering the reservoir, and a sterilization module mounted on at least one of the reservoir and the reservoir cover, in which the sterilization module includes a light source configured to irradiate ultraviolet light inside the reservoir, a board having a light emitting surface, on which the light source is mounted, and a back surface opposite to the light emitting surface, a protective tube accommodating the board therein and configured to transmit ultraviolet light irradiated from the light source, and first and second bases respectively provided to both ends of the protective tube, in which one end of the board is coupled to be inserted into the first base and the other end of the board is coupled to be inserted into the second base, and the light emitting surface is spaced apart from a center of each of the first and second bases, when viewed in a cross-section perpendicular to a length direction of the protective tube.

It is to be understood that both the foregoing general description and the following detailed description are exemplary and explanatory and are intended to provide further explanation of the invention as claimed.

BRIEF DESCRIPTION OF DRAWINGS

The accompanying drawings, which are included to provide a further understanding of the invention and are incorporated in and constitute a part of this specification, illustrate exemplary embodiments of the invention, and together with the description serve to explain the inventive concepts.

FIG. 9C is a cross-sectional view of a first base taken along line I-I' of FIG. 9B.

DETAILED DESCRIPTION

Figure 1:
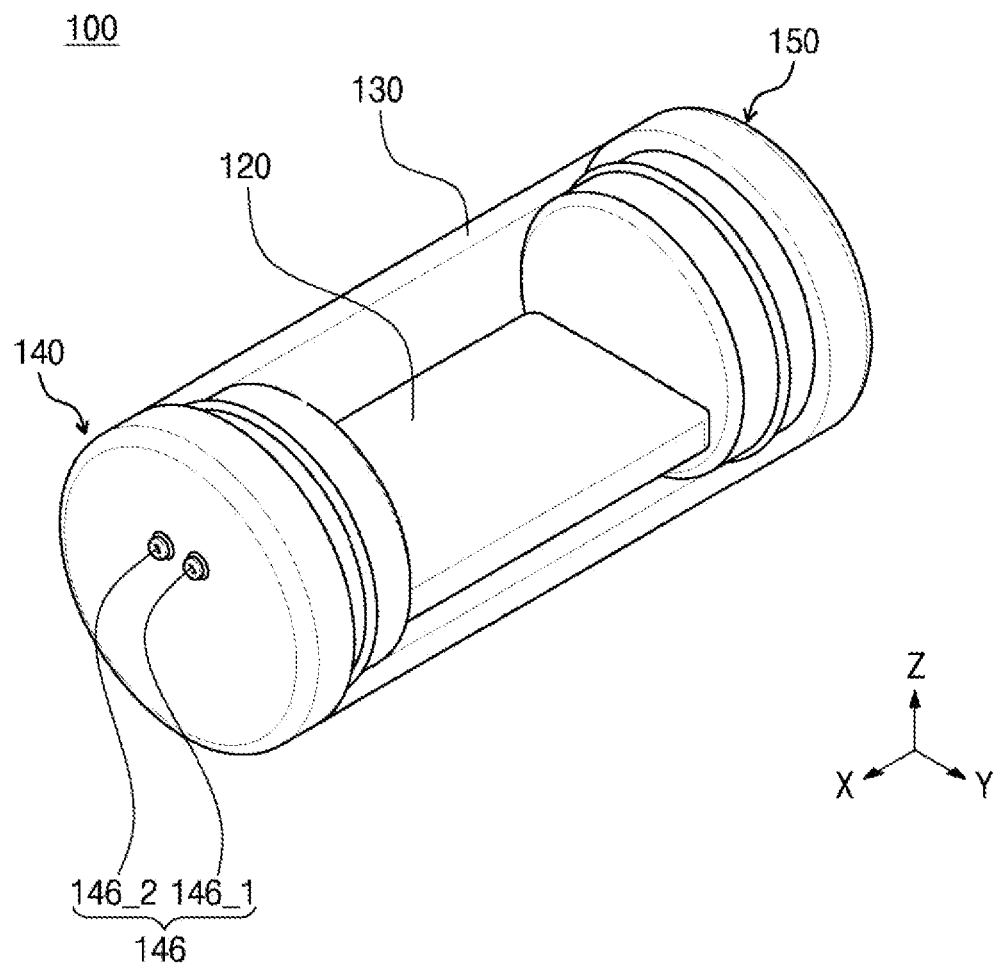
FIG. 1 and FIG. 2 are perspective views illustrating a sterilization module when viewed in different directions.

In the following description, for the purposes of explanation, numerous specific details are set forth in order to provide a thorough understanding of various exemplary embodiments or implementations of the invention. As used herein "embodiments" and "implementations" are interchangeable words that are non-limiting examples of devices or methods employing one or more of the inventive concepts disclosed herein. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments. Further, various exemplary embodiments may be different, but do not have to be exclusive. For example, specific shapes, configurations, and characteristics of an exemplary embodiment may be used or implemented in another exemplary embodiment without departing from the inventive concepts.

Unless otherwise specified, the illustrated exemplary embodiments are to be understood as providing exemplary features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an exemplary embodiment may be implemented differently, a specific process order may be performed differently from the described order. For example, two consecutively described processes may be performed substantially at the same time or performed in an order opposite to the described order. Also, like reference numerals denote like elements.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the D1-axis, the D2-axis, and the D3-axis are not limited to three axes of a rectangular coordinate system, such as the x, y, and z-axes, and may be interpreted in a broader sense. For example, the D1-axis, the D2-axis, and the D3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the exemplary term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various exemplary embodiments are described herein with reference to sectional and/or exploded illustrations that are schematic illustrations of idealized exemplary embodiments and/or intermediate structures. As such, variations from the shapes of the illustrations as a result, for example, of manufacturing techniques and/or tolerances, are to be expected. Thus, exemplary embodiments disclosed herein should not necessarily be construed as limited to the particular illustrated shapes of regions, but are to include deviations in shapes that result from, for instance, manufacturing. In this manner, regions illustrated in the drawings may be schematic in nature and the shapes of these regions may not reflect actual shapes of regions of a device and, as such, are not necessarily intended to be limiting.

As customary in the field, some exemplary embodiments are described and illustrated in the accompanying drawings in terms of functional blocks, units, and/or modules. Those skilled in the art will appreciate that these blocks, units, and/or modules are physically implemented by electronic (or optical) circuits, such as logic circuits, discrete components, microprocessors, hard-wired circuits, memory elements, wiring connections, and the like, which may be formed using semiconductor-based fabrication techniques or other manufacturing technologies. In the case of the blocks, units, and/or modules being implemented by microprocessors or other similar hardware, they may be programmed and controlled using software (e.g., microcode) to perform various functions discussed herein and may optionally be driven by firmware and/or software. It is also contemplated that each block, unit, and/or module may be implemented by dedicated hardware, or as a combination of dedicated hardware to perform some functions and a processor (e.g., one or more programmed microprocessors and associated circuitry) to perform other functions. Also, each block, unit, and/or module of some exemplary embodiments may be physically separated into two or more interacting and discrete blocks, units, and/or modules without departing from the scope of the inventive concepts. Further, the blocks, units, and/or modules of some exemplary embodiments may be physically combined into more complex blocks, units, and/or modules without departing from the scope of the inventive concepts.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

Hereinafter, exemplary embodiments of the inventive concepts will be described in detail with reference to the accompanying drawings.

Figure 2:
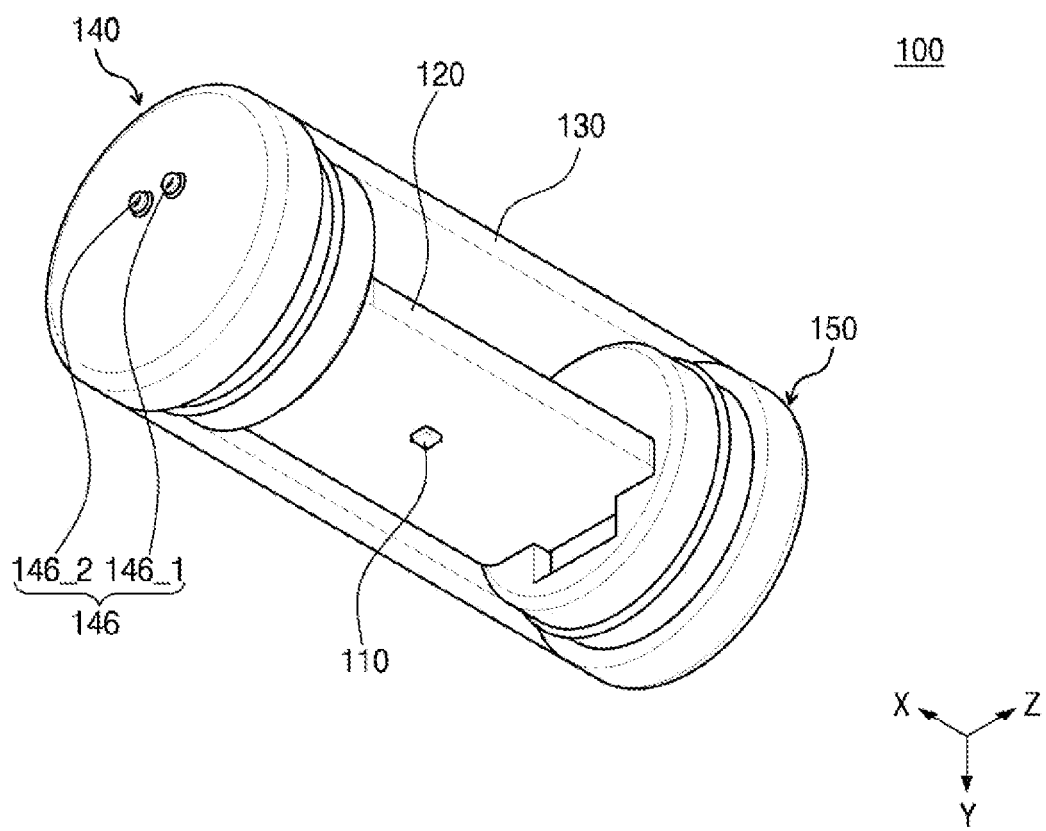
Figure 3:
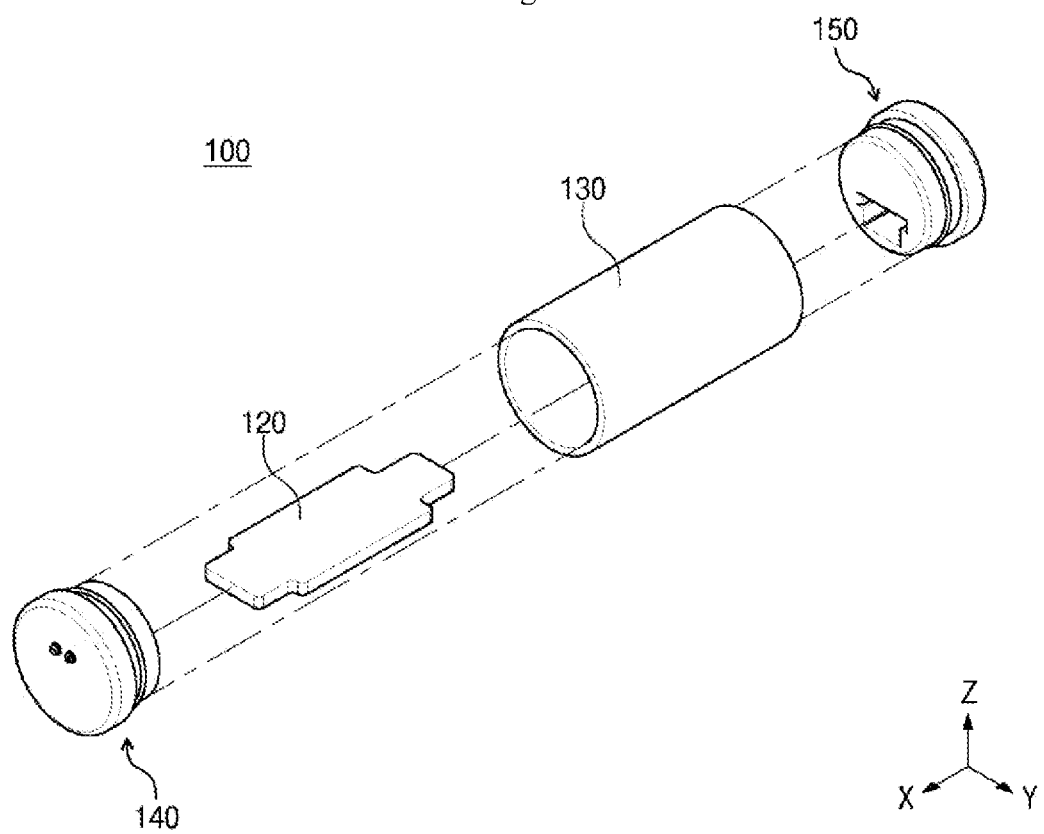
FIG. 3 is an exploded perspective view of a sterilization module.

FIGS. 1 to 3 are views illustrating a sterilization module 100 according to an embodiment. In particular, FIGS. 1 and 2 are perspective views illustrating the sterilization module 100 when viewed in different directions, respectively. FIG. 3 is an exploded perspective view of the sterilization module 100.

Referring to FIGS. 1 to 3, the sterilization module 100 includes a light source 110, a board 120, a protective tube 130, a first base 140, and a second base 150.

The light source 110 is mounted on the board 120 and irradiates UV light. For example, the light source 110 may emit UV light with a sterilization effect towards the water stored in a reservoir or water flowing into a tube. For example, the light source 110 may be a light emitting diode chip that emits UV light in a wavelength range of 200 nm to 280 nm, that is the UVC area. However, the inventive concepts are not limited thereto, and the type and the emission wavelength of the light source 110 are not particularly limited as long as the emitted UV light has a sterilization effect.

The light source 110 may be installed in the form of a metal can, or an injection-type lead frame package that is capable of being mounted on the board 120, or may be installed in the form in which through-hole mounting is possible. Moreover, the light source 110 may be mounted in the type of a bare chip or a flip chip. In this manner, the light source 110 may be implemented with a chip-on-board (COB) package, or may be installed in the form of an intermediate board used to improve heat dissipation or electrical properties.

The board 120 extends in the first direction (e.g., 'X' direction). The light source 110 may be mounted on the front surface of the board 120. The board 120 is electrically connected to the light source 110 so as to provide the light source 110 with power supplied from the outside. For example, the board 120 may be a circuit board, a printed circuit board (PCB), a metal board, or a ceramic board. However, the inventive concepts are not limited to a particular type of the board 120, as long as the board 120 is capable of being electrically connected to the light source 110.

In addition, the board 120 is formed in the form of a plate having the predetermined thickness and strength, such that bending deformation does not occur due to the weight of the board 120 and the weight of the light source 110, when only both ends of the board 120 in the length direction are supported.

The protective tube 130 extends in the first direction and accommodates the board 120 therein. That is, the protective tube 130 may be formed in the shape surrounding the board 120, so as to protect the board 120 and the light source 110 therein from external shocks or fluids. For example, as illustrated in FIGS. 1 to 3, the protective tube 130 may be formed in the shape of a tube having a circular cross-section. However, the inventive concepts are not limited to a particular shape of the protective tube 130, as long as the protective tube 130 is capable of accommodating the board 120 therein.

The protective tube 130 is formed using a material that transmits UV light, such that the UV light emitted from the light source 110 is capable of being emitted to the outside. For example, the protective tube 130 may be formed using at least one of quartz, fused silica, polymethyl methacrylate (PMMA) resin, and fluorinated polymer resin.

The first base 140 and the second base 150 are coupled to one end and the other end of the protective tube 130, respectively. The first base 140 and the second base 150 together with the protective tube 130 may form the appearance of the sterilization module 100, and block the interior of the sterilization module 100 from the exterior of the sterilization module 100. For example, the first base 140 and the second base 150 together with the protective tube 130 may provide a waterproof structure to seal the interior of the sterilization module 100, such that external water does not penetrate into the sterilization module 100.

According to an exemplary embodiment, each of the first base 140 and the second base 150 may be formed to have the same diameter and shape as the protective tube 130. Accordingly, the first base 140 and the second base 150 may be coupled to the protective tube 130 without steps. For example, as illustrated in FIGS. 1 to 3, each of the first base 140 and the second base 150 may include a receiving part, which is accommodated into the inside of the protective tube 130 and is coupled to be inserted into the inside of the protective tube 130, and a cover part contacting an end of the protective tube 130. In this case, each cover part of the first base 140 and the second base 150 may be formed to have the same diameter and shape as the protective tube 130. As such, when viewed from the outside, each of the first base 140 and the second base 150 is connected to the protective tube 130 without step, and when viewed from above the plane, the first base 140 and the second base 150 are each formed to have the plane of a rectangular shape. Accordingly, when coupled to a reservoir or the like, the sterilization module 100 according to an exemplary embodiment may be easily coupled to the reservoir because the shape thereof is simple. In addition, waterproof performance of the sterilization module 100 may be improved because the sealing thereof is easy, which will be described in more detail with reference to FIGS. 12 to 14 below.

Referring to FIGS. 1 to 3, a fixation groove for receiving and fixing one end and the other end of the board 120 is formed in each of the first base 140 and the second base 150. The board 120 is stably positioned in the inner space of the protective tube 130 by inserting both ends of the board 120 into the fixation grooves of the first base 140 and the second base 150. In this case, a specific spaced distance may be formed between the board 120 and the inner peripheral surface of the protective tube 130, such that one side of the board 120 is prevented from being broken because one side of the board 120 contacts the inner peripheral surface of the protective tube 130.

Each of the first base 140 and the second base 150 may include a receiving part, which is accommodated into the inside of the protective tube 130 and is coupled to be inserted into the inside of the protective tube 130, and a cover part contacting an end of the protective tube 130. According to an exemplary embodiment, the cover part and the receiving part may be formed integrally without being separated from each other, which may reduce the manufacturing costs due to simplified process of making the first base 140 and/or the second base 150. Furthermore, there is no small gap that may otherwise be occurred when different parts are coupled, and thus, the inside of the sterilization module 100 is completely blocked from the outside by integrally forming the first base 140 and the second base 150 without being separated from each other, thereby improving waterproof performance.

A through-hole for drawing a wire for supplying power to the light source 110 may be formed in at least one of the first base 140 and the second base 150. For example, as illustrated in FIGS. 1 to 3, two through-holes 146_1 and 146_2 for respectively drawing two wires may be formed in the first base 140. However, the inventive concepts are not limited to a particular shape of a through-hole or the number of through-holes.

As described above, the sterilization module 100 according to an exemplary embodiment includes the light source 110 mounted on the board 120, and the light source 110 emits UV light to the outside via the protective tube 130 surrounding the board 120. For example, the sterilization module 100 according to an exemplary embodiment may be installed in an external device, such as a water purification device, and may sterilize the water stored in the water purification device.

In particular, the sterilization module 100 according to an exemplary embodiment may be formed such that there is no step between the protective tube 130 and the bases 140 and 150. As such, the sterilization module 100 may be easily coupled to an external water purification device. In addition, the waterproof performance may be improved because the sealing to the external device is easy. Furthermore, the bases 140 and 150 of the sterilization module 100 according to an exemplary embodiment of may be integrally formed without being separated from each other. Accordingly, the manufacturing costs thereof may be reduced because a process of producing a base is simplified. In addition, there is no gap in the process of joining different parts, thereby increasing waterproof efficiency.

As used herein, in FIGS. 1 to 3, the direction in which the board 120 and the protective tube 130 extend is referred to as a first direction (e.g., 'X' direction), two directions on the plane intersecting the first direction are referred to as a second direction (e.g., 'Y' direction) and a third direction (e.g., 'Z' direction). However, the first to third directions X, Y, and Z are merely exemplary, and the first to third directions X, Y, and Z may be set differently in other exemplary embodiments.

Figure 4:
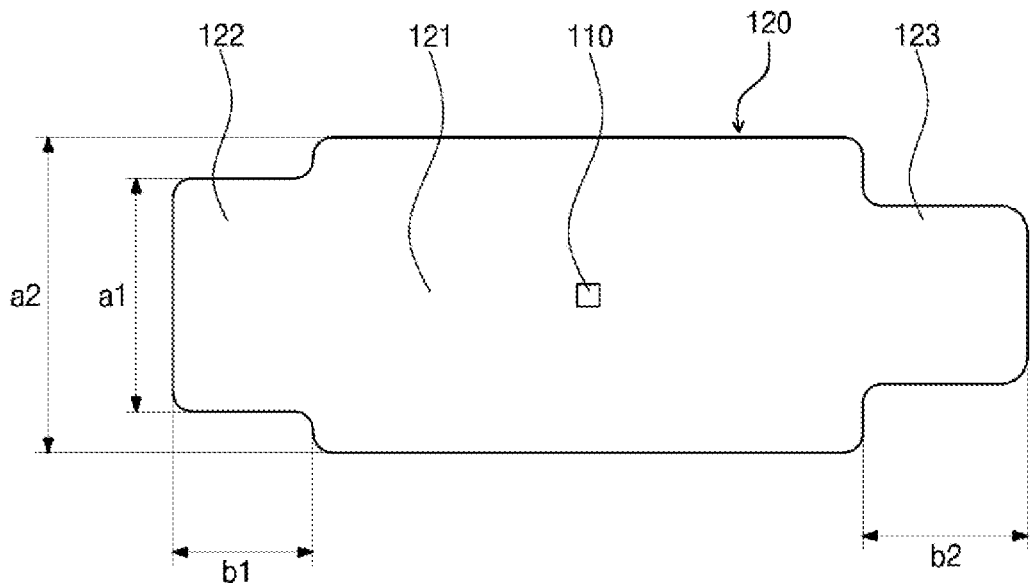
FIG. 4 is a plan view illustrating an appearance of a board and a light source.
Figure 5:
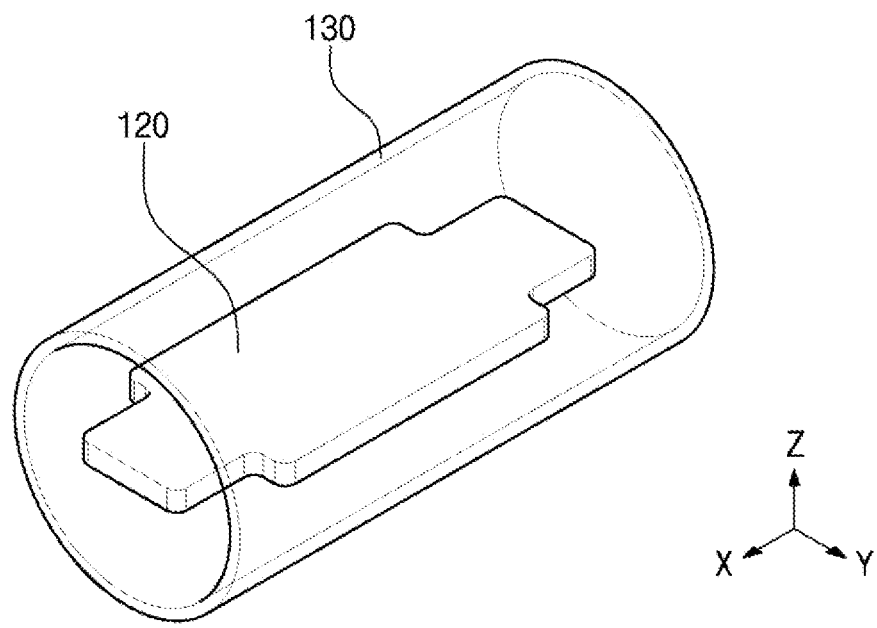
FIG. 5 is a perspective view illustrating an appearance of the board and the protective tube of FIG. 1.

FIGS. 4 and 5 are views for describing in more detail the light source 110 of FIG. and the board 120 for mounting the light source 110 thereon. In particular, FIG. 4 is a plan view illustrating the board 120 and the light source 110. FIG. 5 is a perspective view of the light source 110 in detail.

Referring to FIG. 4, the board 120 extends in the first direction and has a polygonal shape. The light source 110 is mounted at the central portion of the board 120. Accordingly, the central portion of the board 120 may be referred to as a chip mounting part 121. Peripheral circuits, such as connectors or the like, may be mounted on both sides of the board 120, respectively. Accordingly, both the sides of the board 120 may be referred to as peripheral circuit mounting parts 122 and 123.

The peripheral circuit mounting parts 122 and 123 are coupled to be inserted into the fixation grooves of the corresponding bases, respectively. Accordingly, a length a1 in the second direction of the peripheral circuit mounting parts 122 and 123 may be different from a length a2 in the second direction of the chip mounting part 121, such that the peripheral circuit mounting parts 122 and 123 are capable of stably being coupled to the corresponding fixation groove. For example, as illustrated in FIG. 4, the length a1 in the second direction of the peripheral circuit mounting parts 122 and 123 may be less than the length a2 in the second direction of the chip mounting part 121.

In this case, the length a1 in the second direction of the peripheral circuit mounting part 122 may correspond to the length of the fixation groove in the corresponding base. For example, referring to FIG. 9B, the length a1 in the second direction of the peripheral circuit mounting part 122 may be equal to or slightly greater than a distance c1 between a first fixation groove 144_1 and a second fixation groove 144_2, such that the peripheral circuit mounting part 122 of one side is coupled to be inserted into the first base 140.

Figure 11A:
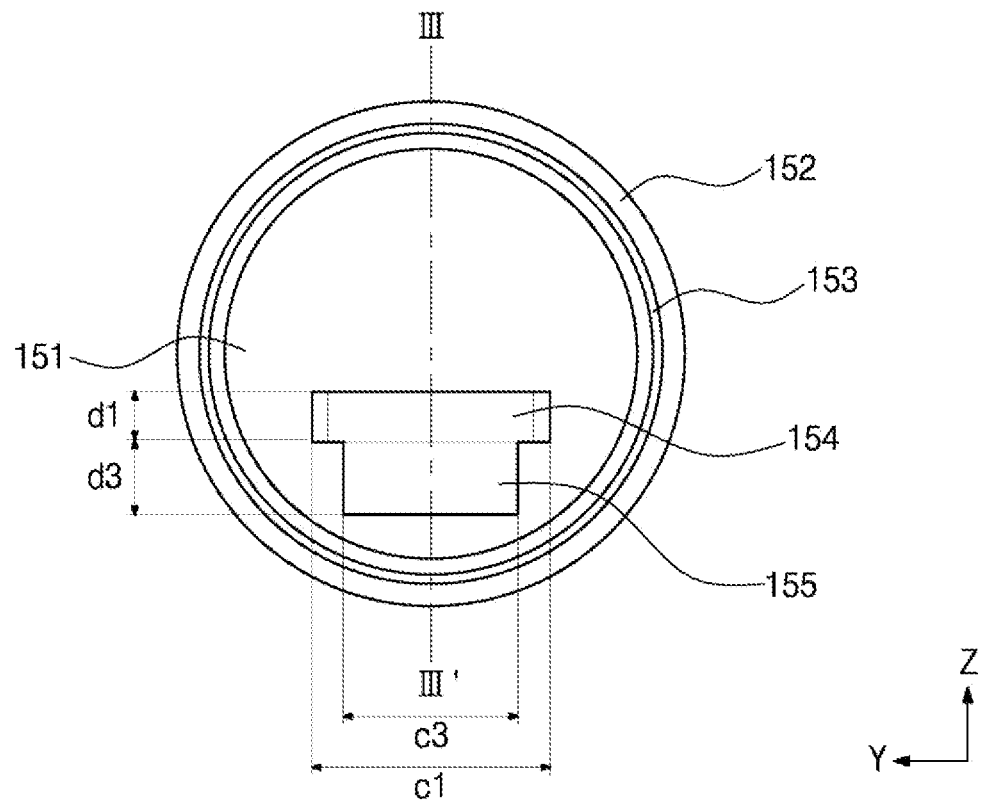
FIG. 11A is a plan view of a second base when viewed in a first direction.

Likewise, referring to FIG. 11A, the length a1 in the second direction of the peripheral circuit mounting part 123 may be equal to or slightly greater than a length c1 in the second direction of a fixation groove 154, such that the peripheral circuit mounting part 123 of the other side is coupled to be inserted into the second base 150. However, the inventive concepts are not limited thereto, as long as both ends of the board 120 may be stably fixed to the first and second fixation grooves 144 and 154, respectively.

Furthermore, for the purpose of forming a spaced space that allows the wire connected to the peripheral circuits, such as connectors or the like, to be drawn to the outside, the length in the first direction of at least one of the peripheral circuit mounting parts 122 and 123 may be less than the length in the first direction of the corresponding receiving groove. For example, referring to FIGS. 4 and 9D, a length b1 in the first direction of the peripheral circuit mounting part 122 of one side may be less than a length f1 in the first direction of a corresponding receiving groove 145. Accordingly, the wire connected to a connector 111 is guided to a withdrawal groove 147 via the spaced space formed between the board 120 and the peripheral circuit mounting part 122. The wire guided to the withdrawal groove 147 may be drawn via a through-hole 146. Moreover, referring to FIGS. 4 and 11B, a length b2 in the first direction of the peripheral circuit mounting part 123 of the other side may be the same as a length g2 in the first direction of the corresponding fixation groove 154, and thus, the board 120 may be supported stably.

According to an exemplary embodiment, reflection materials may be coated on the front surface of the board 120, on which the light source 110 is mounted, to increase sterilization efficiency. For example, the front surface of the board 120 may be coated with a material having high reflectance, such as stainless steel, aluminum, magnesium oxide, and Teflon. In this manner, UV light may be prevented from being lost because the UV light is reflected by the front surface of the board 120, thereby increasing the sterilization efficiency of the sterilization module 100.

The board 120 may be, but is not limited to, a heat dissipation board. For example, the board 120 may be a PCB, a metal board, or a ceramic board.

Referring to FIG. 4, the light source 110 is mounted on the front surface of the board 120 and emits UV light having sterilization effect. The board 120 of FIG. 4 according to the illustrated exemplary embodiment is shown as including a single light source 110 mounted on the front surface of the board 120. However, the inventive concepts are not limited to a particular number of the light sources 110 mounted on the board 120. For example, a plurality of light sources 110 may be mounted on the upper surface of the board 120.

According to an exemplary embodiment, the light source 110 may be mounted on the board 120 in a variety of manners. For example, the light source 110 may be an LED, and the LED may be formed by growing a conductive semiconductor layer, an active layer, and the like on an epitaxial substrate. The LED may be a flip chip type. In this case, when the LED is mounted on the board 120, the epitaxial substrate faces the protective tube 130 while being spaced apart from the board 120. As such, UV light may be emitted through the epitaxial substrate. In this case, because the beam angle of UV light passing through the epitaxial substrate is greater than the beam angle of UV light not passing through the epitaxial substrate, a wider range may be sterilized effectively.

Although not illustrated, the light source 110 according to an exemplary embodiment may include a light emitting structure including a first conductive semiconductor layer, an active layer, and a second conductive semiconductor layer sequentially formed the an epitaxial substrate. The first and second electrodes may be provided on the first conductive semiconductor layer and the second conductive semiconductor layer, respectively. The light source 110 may be provided in the form of a flip chip having a mesa structure. The stacked structure may be inverted and the first electrode and the second electrode may be connected to the above-described board 120. As such, the epitaxial substrate may be disposed to be spaced apart from the board 120, and the light emitting structure may be interposed between the epitaxial substrate and the board 120.

According to an exemplary embodiment, the first and second electrodes of the light source 110 may be mounted on the board 120, directly or via pads.

For example, when the light source 110 is mounted on the board 120 via a pad, two pads interposed between the light source 110 and the board 120 may be provided, and the two pads may be in contact with the first electrode and the second electrode, respectively. For example, the pad may be, but is not limited to, a solder or eutectic metal. For example, AuSn may be used as the eutectic metal.

As another example, when the light source 110 is mounted directly on the board 120, the first electrode and second electrode of the light source 110 may be directly bonded to the wire on the board 120. In this case, the bonding material may include an adhesive material having conductive properties. For example, the bonding material may include a conductive material of at least one of silver (Ag), tin (Sn), and copper (Cu). However, the inventive concepts are not limited thereto. In some exemplary embodiments, the bonding material may include various other materials having conductivity.

Figure 6:
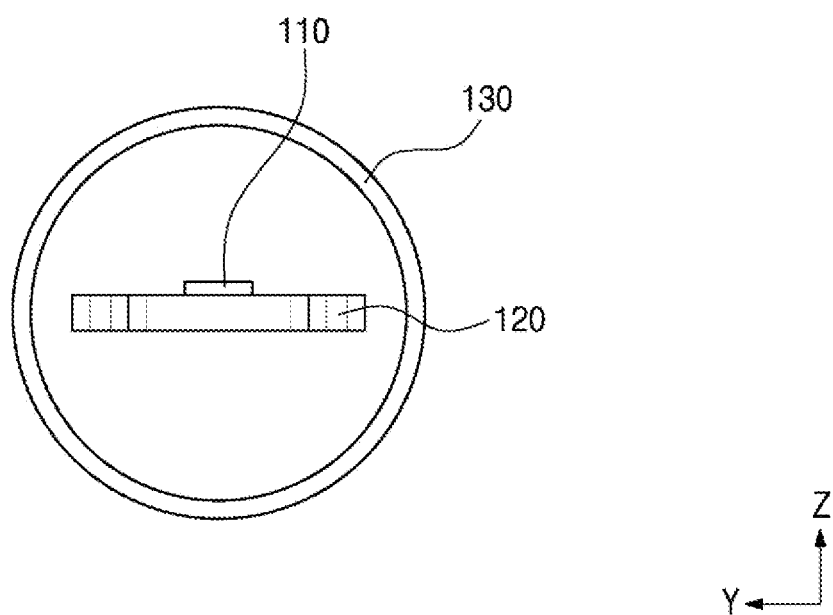
FIG. 6 is a cross-sectional view illustrating an appearance of the board and the protective tube of FIG. 1.
Figure 7A:
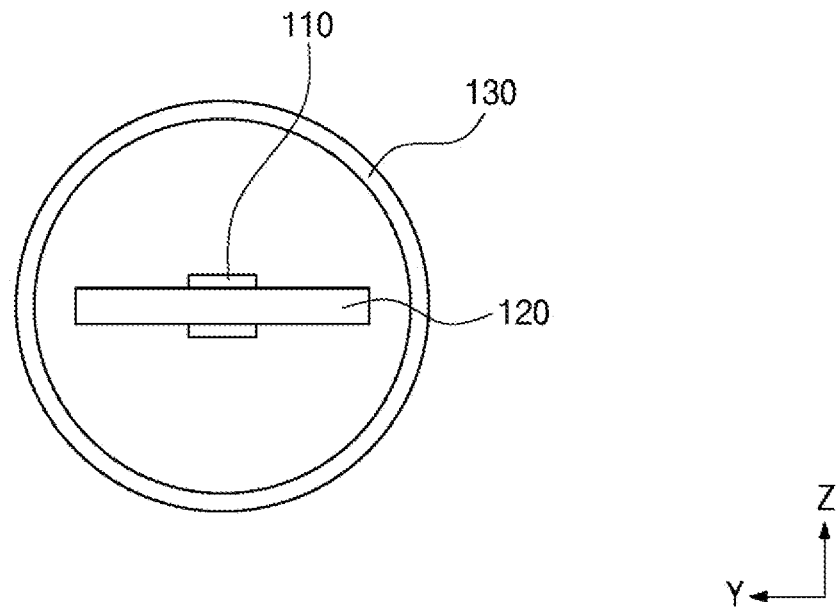
FIG. 7A, FIG. 7B, and FIG. 7C are cross-sectional views illustrating a shape of a board according to exemplary embodiments.
Figure 7B:
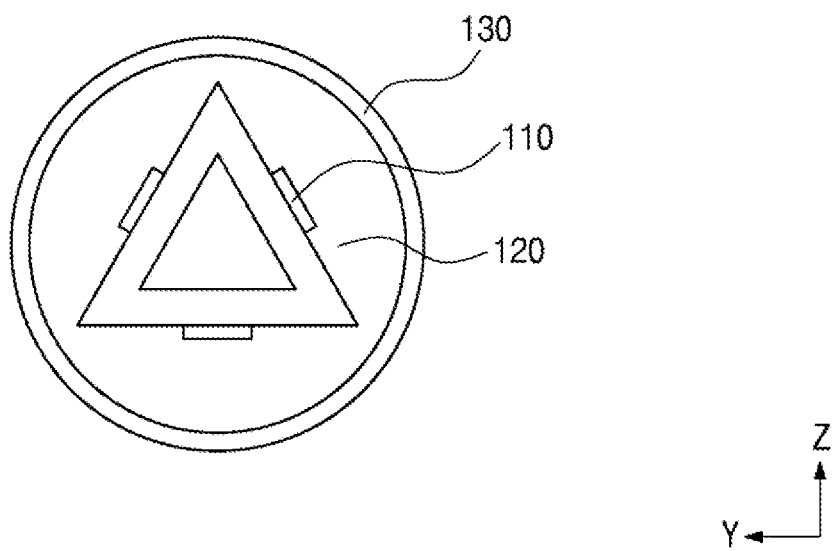
Figure 7C:
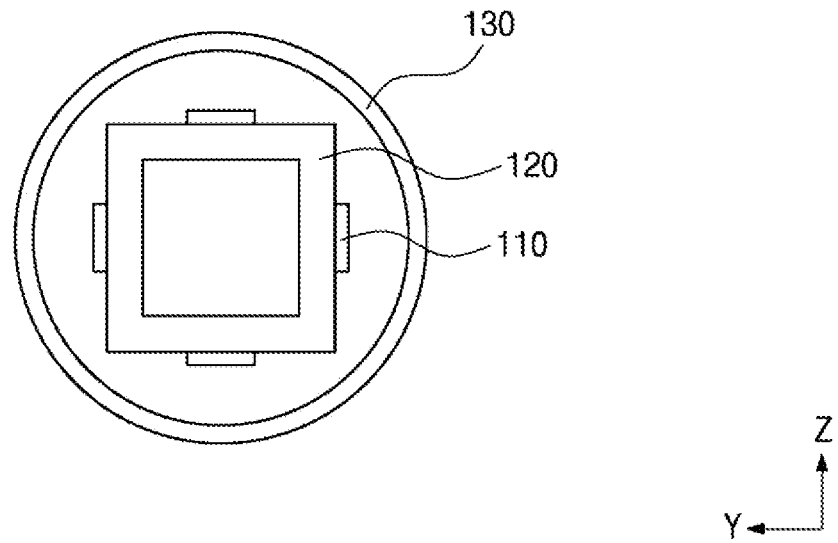
Figure 8A:
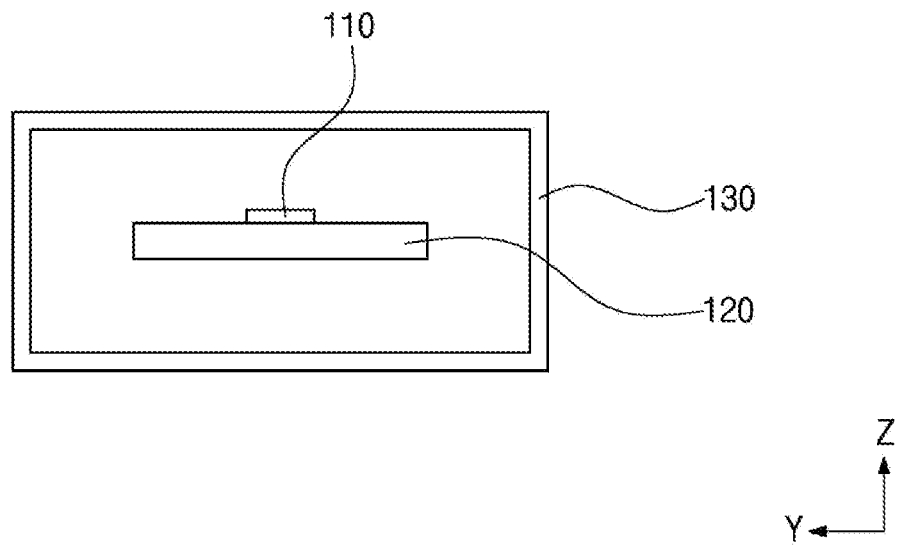
FIG. 8A and FIG. 8B are cross-sectional views illustrating a shape of a protective tube according to another exemplary embodiment.
Figure 8B:
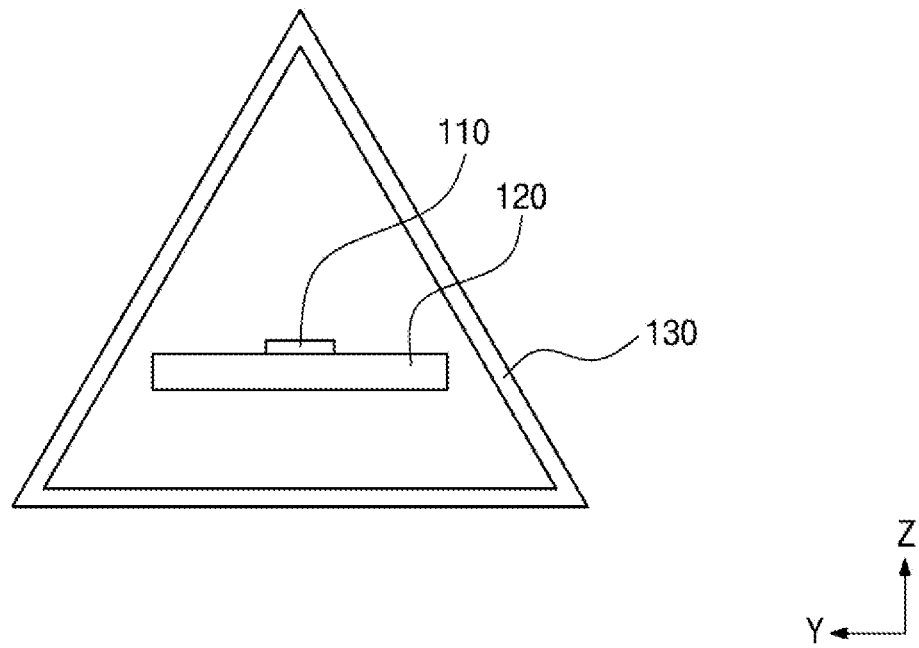

FIGS. 6, 7A, 7B, 7C, 8A, and 8B are views for describing the board 120 and the protective tube 130 of FIG. 1 in more detail. In particular, FIGS. 5 and 6 are a perspective view and a cross-sectional view illustrating the board 120 and the protective tube 130 of FIG. 1, respectively. FIGS. 7A to 7C are cross-sectional views illustrating a shape of the board 120 according to exemplary embodiments. FIGS. 8A and 8B are cross-sectional views illustrating a shape of the protective tube 130 according to another exemplary embodiment.

Referring to FIGS. 5 and 6, each of the board 120 and the protective tube 130 extends in the first direction. The diameter in the second direction of the protective tube 130 is greater than the length in the second direction of the board 120, and thus, the board 120 is disposed to be inserted in the inner space of the protective tube 130. That is, the protective tube 130 is disposed to surround the board 120. In this case, the board 120 may be positioned near the center of the protective tube 130, such that the board 120 may not be broken by contacting the inner peripheral surface of the protective tube 130. As such, because the protective tube 130 surrounds the board 120 while not being in contact with the board 120, the board 120 and the light source 110 may be protected from the outside by the protective tube 130.

According to an exemplary embodiment, the epitaxial substrate of the light source 110 is mounted, so as to be positioned in the direction opposite to the direction of the board 120. That is, the light source 110 is mounted on the board 120 in the form of a flip chip. In this case, as described above, because UV light is emitted through the epitaxial substrate, the beam angle of UV light emitted from the light source 110 is greater than that of a general light source.

In the case of a general sterilization module, as the beam angle of UV light becomes wider, UV light may be lost, and thus, the sterilization efficiency may be decreased. For example, in the case of a general sterilization module that irradiates UV light through a protective tube in the shape of a plate, a spacer for forming a spaced space between the plate-shaped protective tube and a light source is formed between the board and the protective tube. This spacer may interfere with sterilization efficiency by absorbing and/or blocking UV light emitted from the light source. In addition, as the beam angle becomes wider, the loss of UV light also increases due to the impact on the spacer supporting the protective tube, which may lead to the decrease in sterilization efficiency. On the other hand, the sterilization module 100 according to an exemplary embodiment provides the cylindrical protective tube 130 surrounding the board 120 and the light source 110. Accordingly, even though the light source 110 mounted on the board 120 has a wide beam angle, UV light may be emitted to the outside without loss, thereby increasing the sterilization efficiency.

According to an exemplary embodiment shown in FIGS. 5 and 6, the single light source 110 and the single board 120 are provided, and the light source 110 is shown as irradiating UV light in a direction. However, the inventive concepts are not limited thereto. For example, as illustrated in FIGS. 7A to 7C, a plurality of light sources 110 may be provided on the board 120, such that a plurality of light sources 110 emit UV light in different directions. For example, as illustrated in FIG. 7A, a double-sided board may be provided to irradiate UV light in two different directions. As illustrated in FIGS. 7B and 7C, a multi-sided board may be provided to irradiate UV light in three or more different directions.

In FIGS. 5 and 6, the cross-section in the second direction of the protective tube 130 is shown as being a circular shape when viewed in the first direction. However, the inventive concepts are not limited thereto. For example, as illustrated in FIGS. 8A and 8B, the protective tube 130 according to another exemplary embodiment may be formed to have a shape, in which the cross-section in the second direction is polygonal.

Figure 9A:
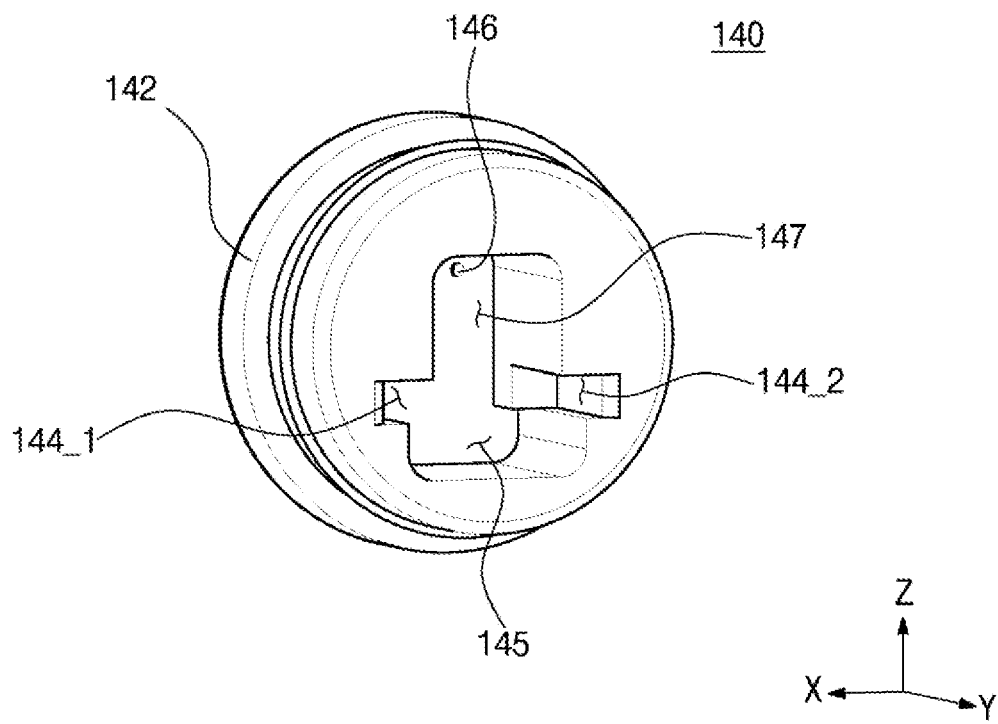
FIG. 9A is a perspective view illustrating an overall view of a first base.
Figure 9B:
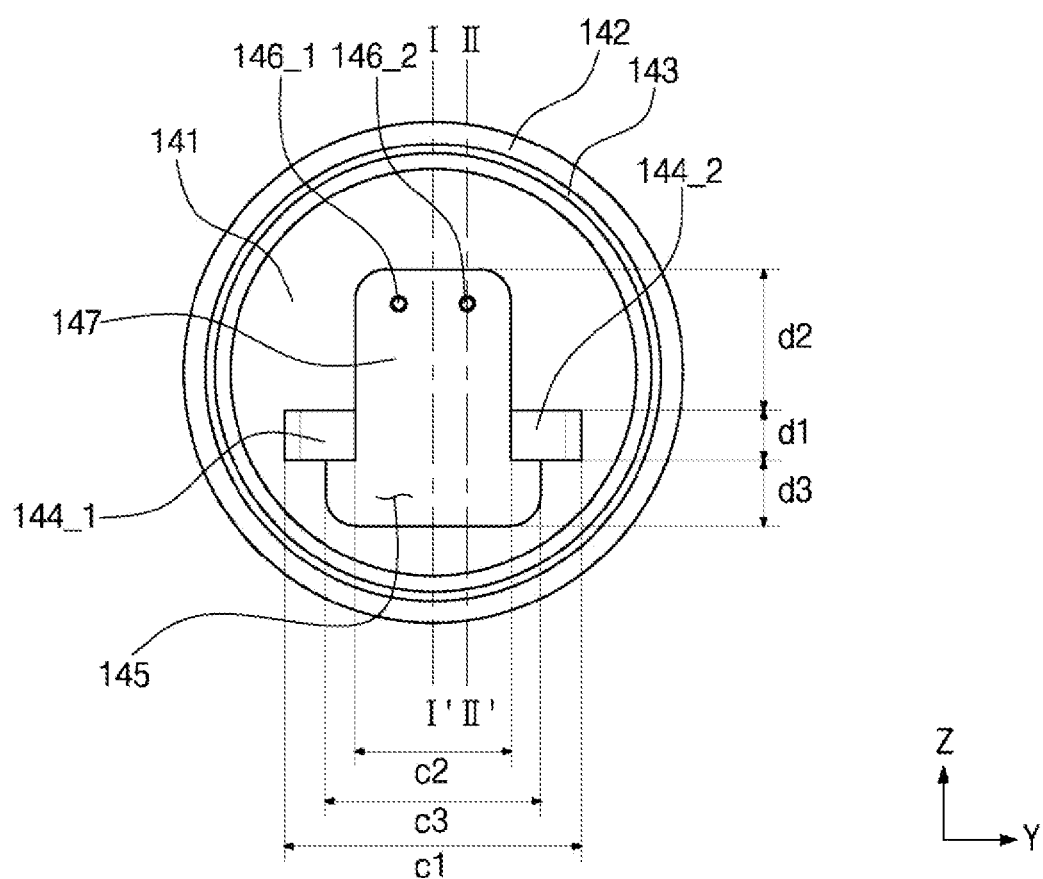
FIG. 9B is a plan view of a first base when viewed in a first direction.
Figure 9D:
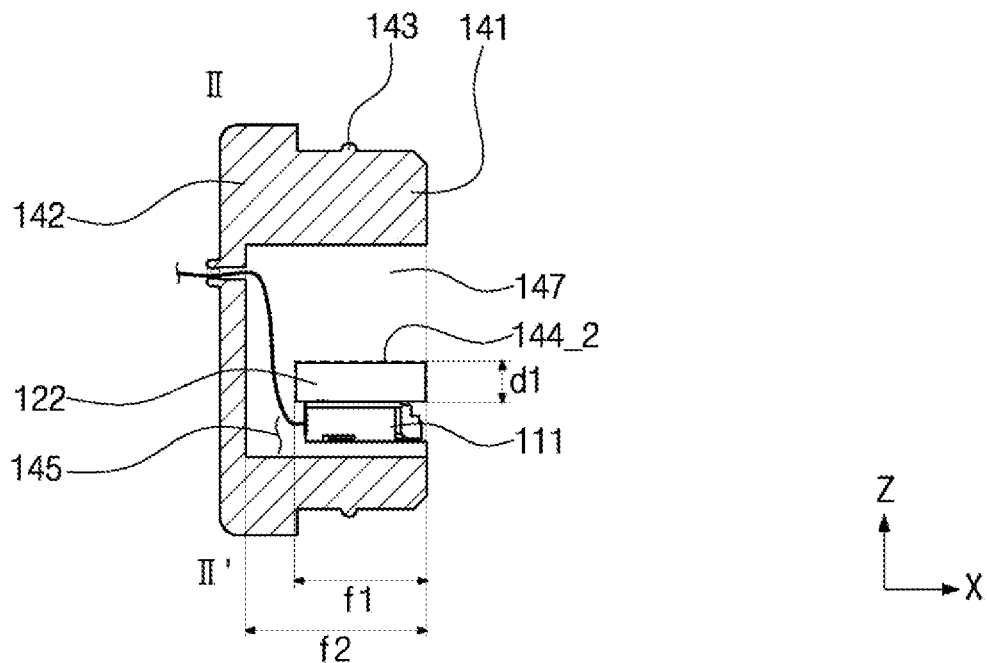
FIG. 9D is a cross-sectional view of a first base taken along line II-IF of FIG. 9B when a board is coupled, as a view illustrating a coupling relationship with a board.

FIGS. 9A to 9D are views illustrating the first base 140 of FIG. 1 in detail. In particular, FIG. 9A is a perspective view illustrating the overall view of the first base 140. FIG. 9B is a plan view of the first base 140 when viewed in the first direction. FIG. 9C is a cross-sectional view of the first base 140 taken along line I-I' of FIG. 9B. FIG. 9D is a cross-sectional view of the first base 140 taken along line II-IF of FIG. 9B when the board 120 is coupled, as a view illustrating a coupling relationship with the board 120.

Referring to FIGS. 9A to 9D, the first base 140 includes an insertion part 141 and a cover part 142.

The insertion part 141 is the portion inserted into the protective tube 130, and has a diameter corresponding to the inner diameter of the protective tube 130 when viewed in a cross-section perpendicular to the length direction of the protective tube 130. For example, the insertion part 141 may have a diameter less than the inner diameter of the protective tube 130, so as to be inserted easily into the protective tube 130. Furthermore, when the first base 140 is elastic, the insertion part 141 may have a diameter substantially the same as the inner diameter of the protective tube 130.

The cover part 142 may be formed on one side of the insertion part 141, and may be integrally formed without being separated from the insertion part 141. According to an exemplary embodiment, when viewed in a cross-section perpendicular to the length direction of the protective tube 130, the cover part 142 has the diameter greater than that of the insertion part 141. That is, when viewed in the cross-section perpendicular to the length direction of the protective tube 130, and when the diameter of the insertion part 141 is a second diameter r2 and the diameter of the cover part 142 is a second diameter r1, the second diameter r2 is less than the first diameter r1.

As such, a stepped part may be formed at a point where the insertion part 141 and the cover part 142 are connected due to the greater diameter of the cover part 142. Until the end of the protective tube 130 reaches the stepped part, the insertion part 141 may be inserted into the protective tube 130.

According to an exemplary embodiment, the first diameter r2 may correspond to the inner diameter of the protective tube 130, and the second diameter r1 may correspond to the outer diameter (i.e., the diameter of the outer surface) of the protective tube 130. That is, the first diameter r2 may be substantially the same as the inner diameter of the protective tube 130, and the second diameter r1 may be substantially the same as the outer diameter of the protective tube 130. The difference between the second diameter r1 and the first diameter r2 may correspond to the thickness of the protective tube 130. As such, the second diameter r1 is provided equal to the diameter of the outer peripheral surface of the protective tube 130, and thus, the outer surface of the sterilization module has a smooth shape without steps, such as irregularities even after the first base 140 is inserted into the protective tube 130.

As described above, when the sterilization module has a relatively smooth shape without separate irregularities, such as stepped parts, it is easy to implement a waterproof structure in the device requiring waterproofing, as well as the sterilization module may be easily mounted on other components. In particular, because the diameter r1 in the third direction of the cover part 142 is the same as the diameter r1 in the third direction of the protective tube 130, the first base 140 and the protective tube 130 may be coupled without steps. When being coupled to an external device, such as a water purification device and/or a water bath, the sterilization module 100 according to an exemplary embodiment may be easily installed in the external device to be sealed, thereby preventing the leakage between the external device and the sterilization module.

The first and second fixation grooves 144_1 and 144_2, the receiving groove 145, and the withdrawal groove 147 are formed in the insertion part 141.

The first and second fixation grooves 144_1 and 144_2 are recessed from the surface of the insertion part 141. One end of the peripheral circuit mounting part 122 of the board 120 is accommodated and fixed in the first and second fixation grooves 144_1 and 144_2.

For example, as illustrated in FIGS. 4, 9A, and 9B, the distance c1 in the second direction between the first fixation groove 144_1 and the second fixation groove 144_2 corresponds to the distance a1 in the second direction of the peripheral circuit mounting part 122, and the height d1 of the first fixation groove 144_1 and the second fixation groove 144_2 corresponds to the thickness of the peripheral circuit mounting part 122. Moreover, referring to FIGS. 4, 9A, and 9D, the depth f1 in the first direction of the first fixation groove 144_1 and the second fixation groove 144_2 corresponds to the depth b1 in the first direction of the peripheral circuit mounting part 122. Accordingly, both side surfaces of the peripheral circuit mounting part 122 may be accommodated and fixed in the first fixation groove 144_1 and the second fixation groove 144_2, respectively.

The receiving groove 145 is connected to the first and second fixation grooves 144_1 and 144_2, and is recessed from the surface of the insertion part 141. A peripheral circuit, such as a connector mounted on the peripheral circuit mounting part 122, is accommodated in the receiving groove 145. For example, as illustrated in FIG. 9D, the connector 111 may be accommodated in the receiving groove 145. However, the inventive concepts are not limited thereto, and in some exemplary embodiments, various peripheral circuits and/or electronic elements may be accommodated in addition to the connector. As such, the peripheral circuit may be accommodated in the receiving groove 145, and thus, the shortened lifetime, malfunction, and/or discoloration of the peripheral circuit due to UV light emitted from the light source 110 mounted on the board 120 may be prevented.

The receiving groove 145 is formed to accommodate the peripheral circuit therein, and the receiving groove 145 is formed deeper than the fixation grooves 144_1 and 144_2 so as to form the spaced space for drawing the wire connected to the peripheral circuit to the outside.

In more detail, for example, as illustrated in FIGS. 9B and 9D, the receiving groove 145 may provide a space for accommodating the connector 111. That is, the length c3 in the second direction of the receiving groove 145 may be formed to be greater than the length in the second direction of the connector 111, and less than the distance c1 between the first and second fixation grooves 144_1 and 144_2. Also, the height d3 in the third direction of the receiving groove 145 may be formed to be greater than the height of the connector 111.

Moreover, as illustrated in FIGS. 9C and 9D, the depth f2 in the first direction of the receiving groove 145 may be formed to be deeper than the depth f1 in the first direction of the first and second fixation grooves 144_1 and 144_2. Accordingly, when the board 120 is coupled, the spaced space may be formed between the peripheral circuit mounting part 122 and the receiving groove 145, and the wire connected to connector 111 may be guided to the withdrawal groove 147 through the spaced space. Furthermore, the wire guided to the withdrawal groove 147 may be drawn to the outside through the through-hole 146. As such, the wire connected to the board 120 may be easily withdrawn to the outside by forming the depth f2 in the first direction of the receiving groove 145 deeper than the depth f1 in the first direction of the fixation grooves 144_1 and 144_2.

The withdrawal groove 147 is connected to the first and second fixation grooves 144_1 and 144_2 and the receiving groove 145, and is recessed from the surface of the insertion part 141. The withdrawal groove 147 provides an inner space for drawing the wire connected to the board 120 to the outside.

For example, as illustrated in FIG. 9B, a length c2 in the second direction of the withdrawal groove 147 may be formed to be less than the length c3 in the second direction of the receiving groove 145 and the distance c1 between the first and second fixation grooves 144_1 and 144_2. Also, the height d2 in the third direction of the withdrawal groove 147 may be formed to be greater than the height of the receiving groove 145 or the height of each of the fixation grooves 144_1 and 144_2. However, the inventive concepts are not limited thereto, as long as the length c2 in the second direction of the withdrawal groove 147 is capable of guiding the wire to the through-hole 146.

Moreover, for example, as illustrated in FIG. 9D, the withdrawal groove 147 may be connected to the receiving groove 145. The depth f2 in the first direction of the withdrawal groove 147 may be formed to be the same as the length f2 in the first direction of the receiving groove 145, and to be greater than the depth f1 in the first direction of the fixation groove 144_2. Accordingly, the wire connected to connector 111 may be guided into the withdrawal groove 147 through the spaced space between the peripheral circuit mounting part 122 and the cover part 142. However, the inventive concepts are not limited thereto, as long as the depth f2 in the first direction of the withdrawal groove 147 is capable of guiding the wire to the withdrawal groove 147.

The cover part 142 contacts one end of the protective tube 130. The cover part 142 forms the appearance of the sterilization module 100 together with the protective tube 130. For example, the diameter r1 in the third direction of the cover part 142 may be the same as the diameter r1 in the third direction of the protective tube 130, and may be greater than the diameter r2 in the third direction of the insertion part 141.

The through-hole 146 connected to the withdrawal groove 147 is formed in the cover part 142. For example, the through-hole 146 is provided to draw a wire for supplying power to the light source 110 mounted on the board 120. For example, the diameter of the through-hole 146 may be formed to be equal to or greater than the diameter of the wire. As another example, for the purpose of improving the waterproof effect, the diameter of the through-hole 146 may be slightly less than the diameter of the wire. In FIG. 9A, the cover part 142 is illustrated as including two through-holes 146. However, the inventive concepts are not limited thereto, and in some exemplary embodiments, the through-hole 146 may be formed of a single hole or may be formed of three or more holes.

According to an exemplary embodiment, the insertion part 141 and the cover part 142 that form the first base 140 are integrally formed without being separated from each other. Accordingly, a gap that may otherwise be formed between the parts when different parts are assembled is minimized, thereby improving the waterproof performance.

Referring to FIGS. 9A to 9D, according to an exemplary embodiment, the fixation grooves 144_1 and 144_2 may be spaced from the center of the first base 140 when viewed in the cross-section perpendicular to the length direction of the protective tube 130. When the first base 140 is provided in the form of a circle when viewed in the cross-section perpendicular to the length direction of the protective tube 130, the fixation grooves 144_1 and 144_2 are provided at locations spaced from the center of the circle. When the fixation grooves 144_1 and 144_2 are out of the center of the first base 140, the end of the board, that is, the peripheral circuit mounting part, which is inserted into the fixation grooves 144_1 and 144_2, is also located at a location spaced from the center of the first base 140. In this manner, light may be maximally emitted in a predetermined direction when light needs to be irradiated in a particular direction. The locations of the fixation grooves 144_1 and 144_2 and the location of the board inserted into the fixation grooves 144_1 and 144_2 may be set in consideration of the direction or area to which the light source irradiates. For example, when the sterilization module according to an exemplary embodiment is mounted in the same place as the cover of the reservoir, and light needs to be emitted into the reservoir, the light source may be positioned close to the inside of the reservoir within the protective tube 130, such that light may maximally be emitted inside the reservoir without the disturbance of other components.

According to an exemplary embodiment, the distance or direction, in which the fixation grooves 144_1 and 144_2 and the board are spaced from the center, may be changed in accordance to a side of the board inserted into the fixation grooves 144_1 and 144_2, on which the light source is mounted. For example, when the surface, on which the light source is mounted on the board, is the light emitting surface and the surface opposite to the light emitting surface is the back surface, the light emitting surface may be spaced apart from the center of the first base 140 after the board is inserted into the fixation grooves 144_1 and 144_2 and then mounted.

Also, the longest distance between the light emitting surface and the outer peripheral surface of the first base 140 has a value different from the longest distance between the back surface and the outer peripheral surface of the first base 140. In particular, when viewed in the cross-section perpendicular to the length direction of the protective tube 130, the longest distance between the light emitting surface and the outer peripheral surface of the first base 140 has a value less than the longest distance between the back surface and the outer peripheral surface of the first base 140.

In addition, when viewed in the cross-section perpendicular to the length direction of the protective tube 130, the receiving groove 145 for accommodating a connector or the like may also be spaced apart from the center of the first base 140.

Referring to FIGS. 9A to 9D, an O-ring shaped protrusion may be provided on the outer peripheral surface of the insertion part 141, such that the insertion part 141 is tightly fastened to the protective tube 130 on the insertion part 141 without an empty gap. A protrusion 143 may be formed, such that the diameter of the protrusion 143 is equal to or greater than the diameter of the inner peripheral surface of the protective tube 130, so as to be tightly inserted into the protective tube 130. For example, when the diameter of the insertion part 141 is slightly smaller than the diameter of the inner peripheral surface of the protective tube 130, the O-ring may be provided to have a diameter substantially the same as the diameter of the inner peripheral surface of the protective tube 130. Alternatively, when the diameter of the insertion part 141 is substantially the same as the diameter of the inner peripheral surface of the protective tube 130, the O-ring may be formed to be greater than the diameter of the insertion part 141.

The insertion part 141 or the O-ring shaped protrusion part 143 is formed integrally, and may be formed of an elastic member. As such, the insertion part 141 and the protrusion 143 are easily inserted into the inside of the protective tube 130 depending on the degree of elasticity. After being inserted, the insertion part 141 or the protrusion 143 may be set to have a diameter that is enough to tightly contact inner peripheral surface of the protective tube 130. As such, the protrusion 143 contacts the inner peripheral surface of the protective tube 130, and prevents water from penetrating a gap between the first base 140 and the protective tube 130.

In FIGS. 9A and 9B, the insertion part 141 is illustrated as having a single protrusion 143. However, the inventive concepts are not limited thereto, and in some exemplary embodiments, a plurality of protrusions 143 may be formed on the insertion part 141. Furthermore, in other exemplary embodiments, a protrusion may be omitted from the insertion part 141. For example, for the purpose of improving the waterproof performance, a sealing member, such as a separate O-ring may be provided, instead of the protrusion 143.

In more detail, as illustrated in FIGS. 9A to 9D, for example, when the protrusion 143 is formed on the insertion part 141, the insertion part 141, the cover part 142, and the protrusion 143 that form the first base 140 may be integrally formed without being separated from one another.

In this case, the insertion part 141, the cover part 142, and the protrusion 143 that form the first base 140 may be formed using a soft material having elasticity or an adhesive material. For example, the first base 140 may be formed of an elastic body having a predetermined elasticity as a soft material, such as an O-ring. Thermoplastic resin, thermosetting resin, silicone resin, or the like may be used as the elastic body. For example, the elastic body may include polyethylene, polypropylene, polymethylpentene, polybutene, polybutadiene, polyvinyl chloride, polyvinyl acetate, polyvinylidene chloride, ethylene vinyl acetate copolymer, ethylene-propylene copolymer, ethylene-propylene-diene copolymer, ionomer, polymethyl methacrylate, polytetrafluoroethylene, ethylene polytetrafluoroethylene copolymer, polyacetal (polyoxymethylene), polyamide, polycarbonate, polyphenylene ether, polyethylene terephthalate, polybutylene terephthalate, polyarylate, polystyrene, polyethersulfone, polyimide, polyamideimide, polyphenylene sulfide, polyoxybenzoyl, polyetheretherketone, polyetherimide, polystyrene, polyurethane, polyester, 1, 2-polybutadiene, phenolic resin, urea resin, melamine resin, benzoguanamine resin, diallyl phthalate resin, alkyd resin, epoxy resin, silicon resin, and the like. Alternatively, the elastic body may also include silicone rubber, one-component room temperature vulcanizing (RTV) rubber, two-component RTV rubber, low temperature vulcanizable (LTV) silicone rubber, oil resistant thermosetting rubber, and the like. The elastic body may include at least one of the above-described materials. According to an exemplary embodiment, the first base 140 may be formed of silicone rubber. However, the inventive concepts are not limited to a particularly material of the elastic body forming the first base 140, and in some exemplary embodiments, the elastic body having a predetermined elasticity may be formed of other materials known in the art.

As another example, when the protrusion 143 is not formed on the insertion part 141, the insertion part 141 and the cover part 142 forming the first base 140 may be formed integrally, and an additional sealing member for providing a waterproof structure may be provided. In this case, the first base 140 may be formed using a material of plastic series, and the sealing member may be formed using a soft material having elasticity or an adhesive material.

In FIGS. 9A to 9D, the length in the first direction at the upper portion of the insertion part 141 is shown as being the same as the length in the first direction at the lower portion. However, the inventive concept are not limited thereto. For example, in some exemplary embodiments, the insertion part 141 may be formed, such that the length at the upper portion is different from the length at the lower portion.

Figure 10:
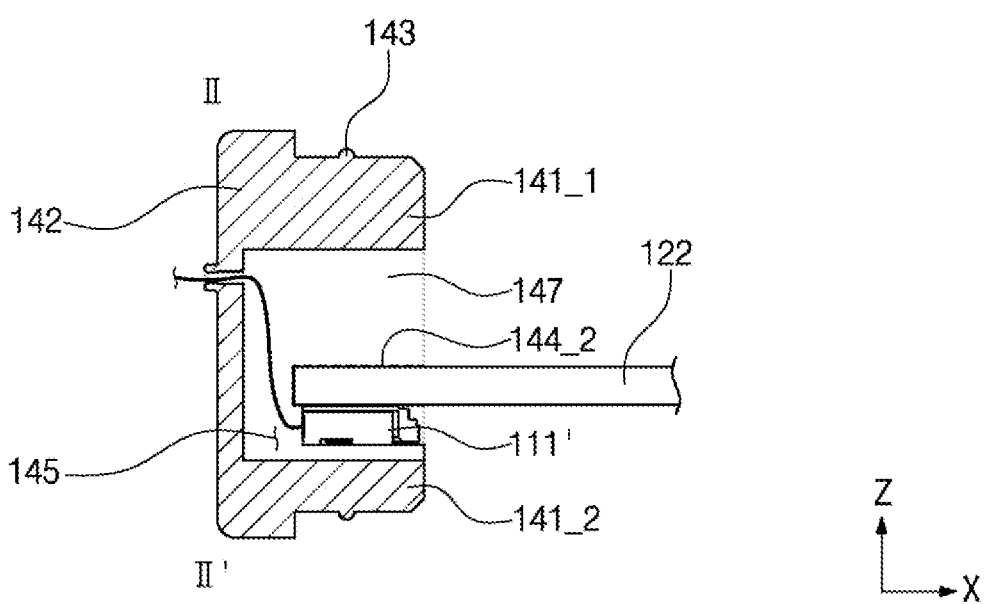
FIG. 10 is a view illustrating a first base according to an exemplary embodiment.

In more detail, referring to FIG. 10, the insertion part 141 of the first base 140 according to an exemplary embodiment includes an upper portion insertion part 141_1 and a lower portion insertion part 141_2. As used herein, the terms "upper portion" and "lower portion" are relative terms based on the board 120, and actual directions thereof may be set differently in other exemplary embodiments. For example, the upper portion insertion part 141_1 may refer to a portion forming the withdrawal groove 147 in the insertion part 141, and the lower portion insertion part 141_1 may refer to a portion forming the receiving groove 145 in the insertion part 141. The connector mounted on the peripheral circuit mounting part 122 may have various lengths. For example, the length in the first direction of the connector 111' of FIG. 10 may be greater than that of connector 111 of FIG. 9D.

In this case, when the lengths of the upper portion insertion part and the lower portion insertion part are the same as each other as illustrated in FIG. 9D, a part of connector 111' may be exposed to the outside without being accommodated in the receiving groove 145. In this case, the part exposed to the outside may be exposed to UV light, and shortened lifetime, malfunctions, and/or discoloration may occur.

As illustrated in FIG. 10, for the purpose of preventing the connector 111' from being exposed to UV light, the connector 111' may be formed, such that the lower portion insertion part 141_2 has a greater length in the first direction than the upper portion insertion part 141_1. In this case, the length in the first direction of the lower portion insertion part 141_2 may correspond to the length in the first direction of connector 111', or may be greater than the length in the first direction of connector 111 in the first direction of the lower portion insertion parexemplary embodiment may mount the peripheral circuit more safely by forming the length of the lower portion insertion part 141_2 in the first direction greater than the upper portion insertion part 141_1.

Figure 11B:
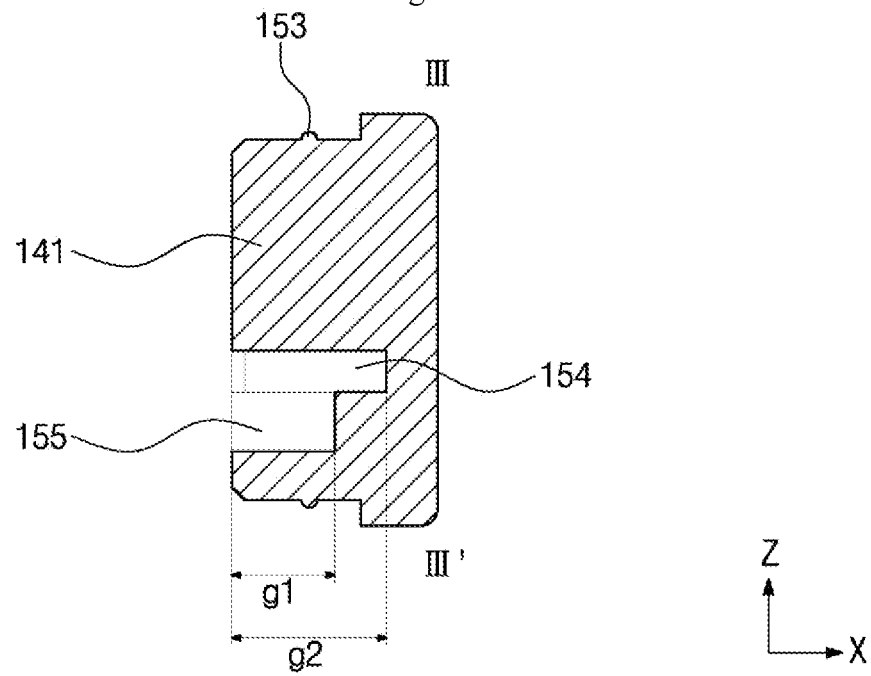
FIG. 11B is a cross-sectional view of a first base taken along line III-III' of FIG. 11A.

FIGS. 11A to 11B are views illustrating the second base 150 of FIG. 1 in detail. In particular, FIG. 11A is a plan view of the second base 150 when viewed in the first direction. FIG. 11B is a cross-sectional view of the first base 140 taken along line III-III' of FIG. 11A.

The second base 150 of FIGS. 11A and 11B is substantially similar to the first base 140 of FIGS. 9A to 9D. Accordingly, similar components are denoted by similar reference numerals, and for the purpose of avoiding redundant descriptions, the differences from the first base will be described mainly.

The second base 150 illustrated in FIGS. 11A and 11B is disposed to face the first base 140 with respect to the protective tube 130. Referring to FIGS. 11A and 11B, the second base 150 includes an insertion part 151 and a cover part 152.

The fixation groove 154 and a receiving groove 155 are formed in the insertion part 151. The fixation groove 154 is recessed from the surface of the insertion part 151. One end of the peripheral circuit mounting part 123 of the board 120 is fastened to the fixation groove 154 and is fixed. For example, the length c1 in the second direction of the fixation groove 154 may correspond to the length a1 in the second direction of the peripheral circuit mounting part 123 (refer to FIG. 4) of the board 120. The height d1 in the third direction of the fixation groove 154 may correspond to the thickness in the third direction of the peripheral circuit mounting part 123.

The receiving groove 155 is connected to the fixation groove, and is recessed from the surface of the insertion part 151. The receiving groove 155 provides a space for accommodating the parts mounted in the peripheral circuit mounting part 123. For example, the length c3 in the second direction of the receiving groove 155 may be formed to be greater than the length in the second direction of the peripheral circuit. The height d3 in the third direction of the receiving groove 155 may be formed to be greater than the height in the third direction of the peripheral circuit. Moreover, the depth g1 in the first direction of the receiving groove 155 may be formed to be greater than the length in the first direction of the peripheral circuit. In this case, the depth g2 in the first direction of the fixation groove 154 may be formed to be greater than the depth g1 in the first direction of the receiving groove 155, such that the board 120 is fastened to the fixation groove 154 and is supported stably.

Unlike the first base 140 illustrated in FIGS. 9A to 9D, the second base 150 of FIGS. 11A and 11B does not include a withdrawal groove and a through-hole. That is, the second base 150 does not provide a configuration for drawing the wire connected to the peripheral circuit to the outside. Accordingly, all the power provided to the peripheral circuit is provided via the wire connected to the first base 140. However, the inventive concepts are not limited thereto. In another exemplary embodiment, the power may be supplied through the second base 150. In this case, the second base 150 may be formed in the same shape as the first base 140 described above, and thus, repeated descriptions thereof will be omitted.

As described above, the sterilization module 100 according to an exemplary embodiment may irradiate UV light with sterilization effect, and may sterilize the stored water after being installed in external device, such as a reservoir. Hereinafter, in FIG. 12, various examples, in each of which the sterilization module 100 of FIG. 1 is installed in an external device, will be described in more detail.

Figure 12A:
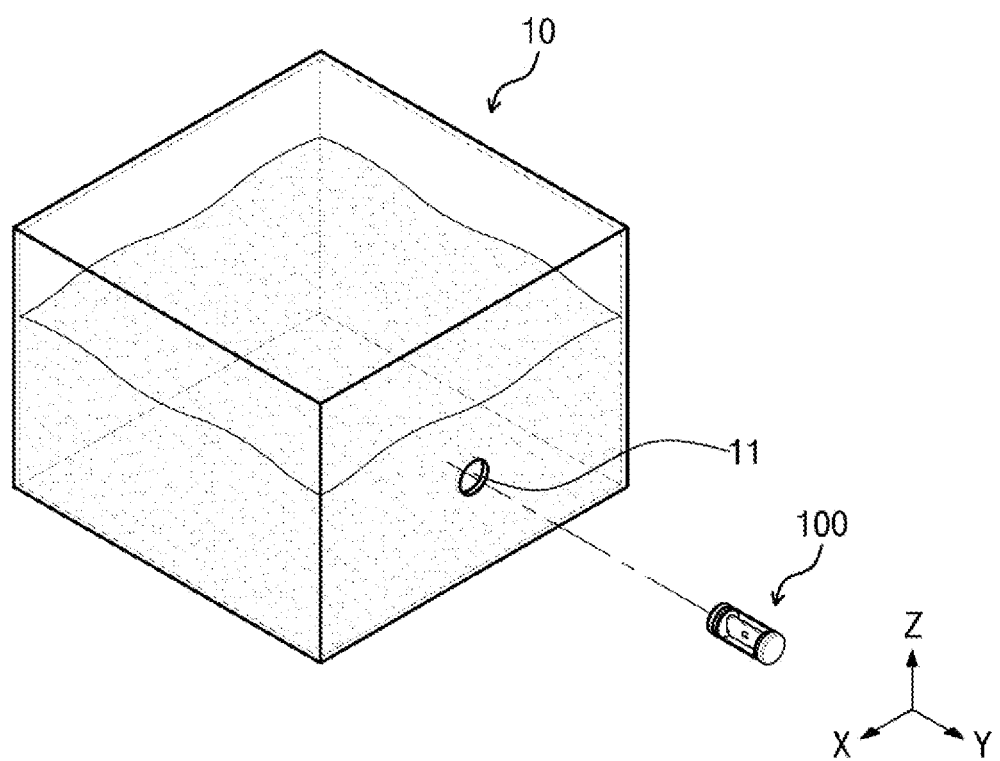
FIG. 12A is a view illustrating a sterilization module installed in a reservoir.
Figure 12B:
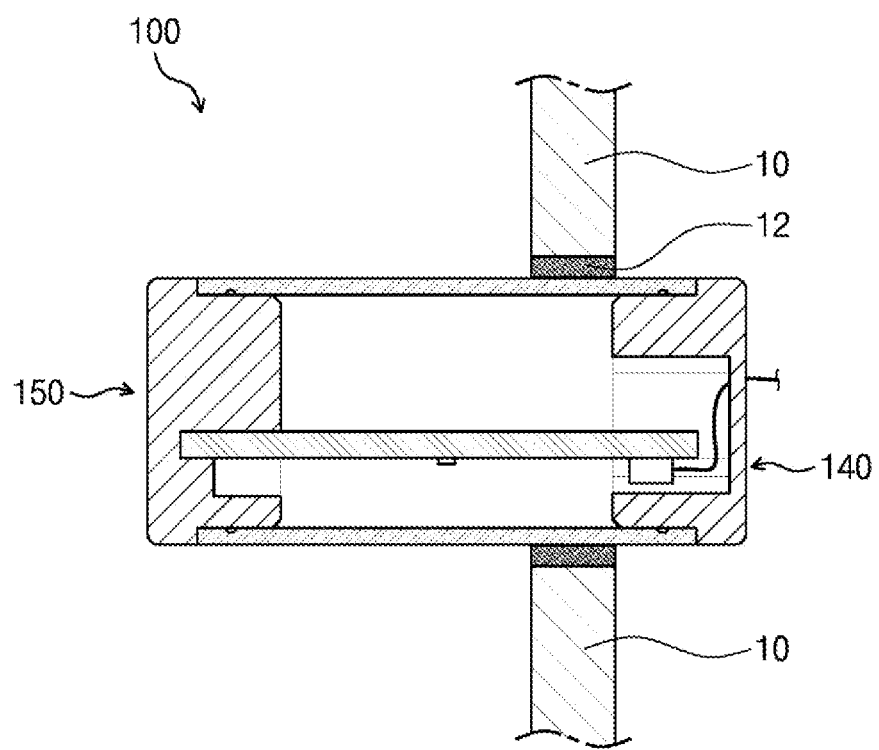
FIG. 12B, FIG. 12C, and FIG. 12D are cross-sectional views illustrating a sterilization module installed in a water purification device.
Figure 12C:
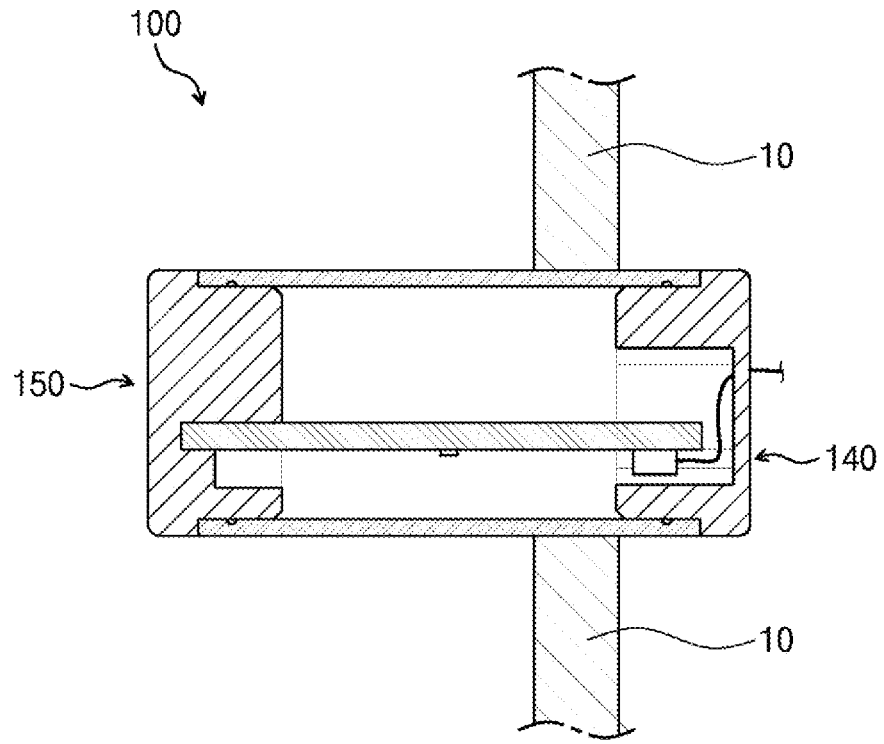
Figure 12D:
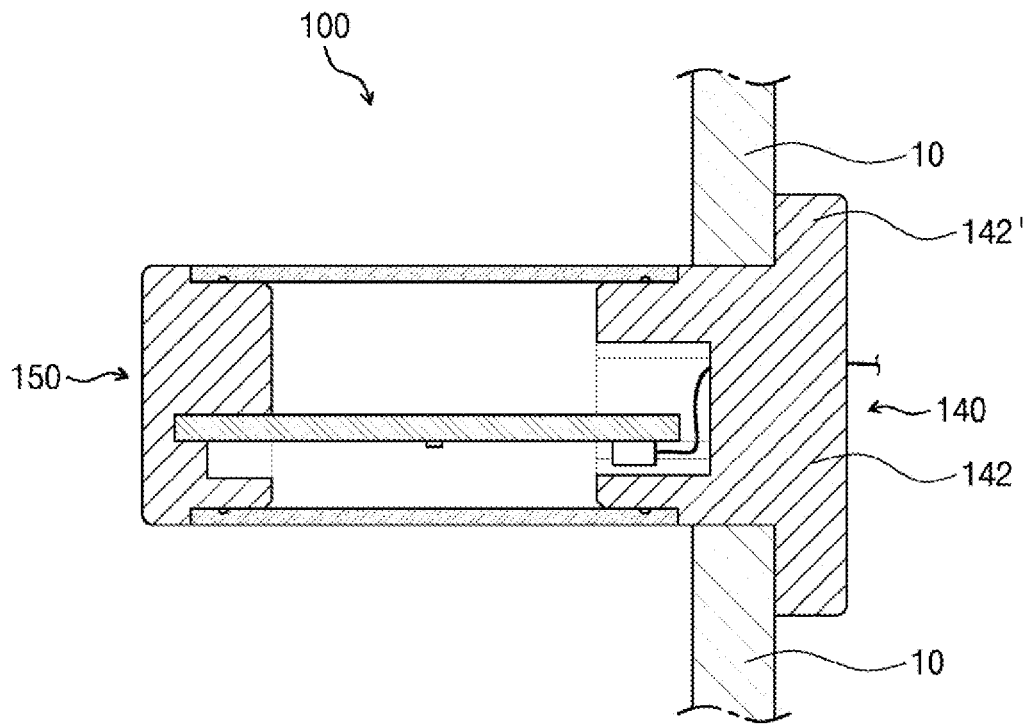

FIGS. 12A to 12D are views illustrating a reservoir 10, in which the sterilization module 100 is installed, according to an exemplary embodiment. In particular, FIG. 12A is a view illustrating the sterilization module 100 installed in the reservoir 10. FIGS. 12B to 12D are cross-sectional views illustrating the sterilization module 100 installed in the reservoir 10 of water purification device.

Referring to FIG. 12A, the reservoir 10 stores water therein, and an installation hole 11 is formed on at least one side surface of the reservoir 10. For example, the installation hole 11 may be formed in the shape of a circle-shaped opening. The opening shape of the installation hole 11 may correspond to the cross-section of each of the first and third directions of the sterilization module 100. In this case, the sterilization module 100 may be coupled to be inserted into the installation hole 11 along the direction (e.g., the second direction), in which the board extends.

Referring to FIGS. 12A and 12B, the sterilization module 100 may be coupled to be inserted into the reservoir 10. In this case, for the purpose of preventing the stored water from leaking via a gap that may be formed when coupling the sterilization module 100 to the reservoir a sealing member 12, such as an O-ring, may be interposed between the installation hole 11 and the protective tube. In this case, the sealing member 12 may be formed using a soft material having elasticity or an adhesive material; for example, the sealing member 12 may be formed of Viton®, ethylene propylene (E.P.R), Teflon®, or Karlez®.

Referring to FIGS. 12A and 12C, the sterilization module 100 may be coupled to be inserted into the reservoir 10 without a sealing member, such as an O-ring. In this case, for the purpose of improving waterproof performance, a part of the base of the sterilization module 100 may contact the installation hole 11. The base formed of an elastic material may contact the installation hole 11, and thus, the water in the reservoir 10 may be prevented from leaking without including a sealing member, such as an O-ring.

Referring to FIGS. 12A and 12D, for the purpose of being reliably coupled to the reservoir 10, the first base 140 of the sterilization module 100 may be connected to the cover part 142, and the coupling part 142', in which the length of the cross-section perpendicular to a board is greater than the diameter of the installation hole 11, may be formed. As illustrated in FIGS. 12A and 12D, the diameter of the coupling part 142' is greater than the diameter of the installation hole 11. Accordingly, the sterilization module 100 may be stably fixed to the reservoir 10.

As described above, the sterilization module 100 according to an exemplary embodiment may be installed in the reservoir 10 to perform a sterilization operation. In particular, as described above, in the sterilization module 100 according to an exemplary embodiment, the light source 110 is mounted on the board 120 in the form of a flip chip. Accordingly, the beam angle of UV light is greater than that in the general case. Accordingly, the sterilization module 100 according to an exemplary embodiment may perform a sterilization operation on a wider range.

Also, as illustrated in FIGS. 7A to 7C, the sterilization module 100 according to an exemplary embodiment may include a plurality of light sources 110, which may emit UV light in different directions. For example, as illustrated in FIG. 7A, the light sources 110 may be provided on a double-sided board to irradiate UV light in two different directions, or as illustrated in FIGS. 7B and 7C, the light sources 110 may be provided on a multi-sided board to irradiate UV light in three or more different directions.

In this case, the area of water irradiated with UV light may be maximized by installing the sterilization module 100 according to an exemplary embodiment in the reservoir 10 as illustrated in FIG. 12A. Accordingly, the sterilization module 100 according to an exemplary embodiment may effectively sterilize a large amount of water in a short time.

Figure 13A:
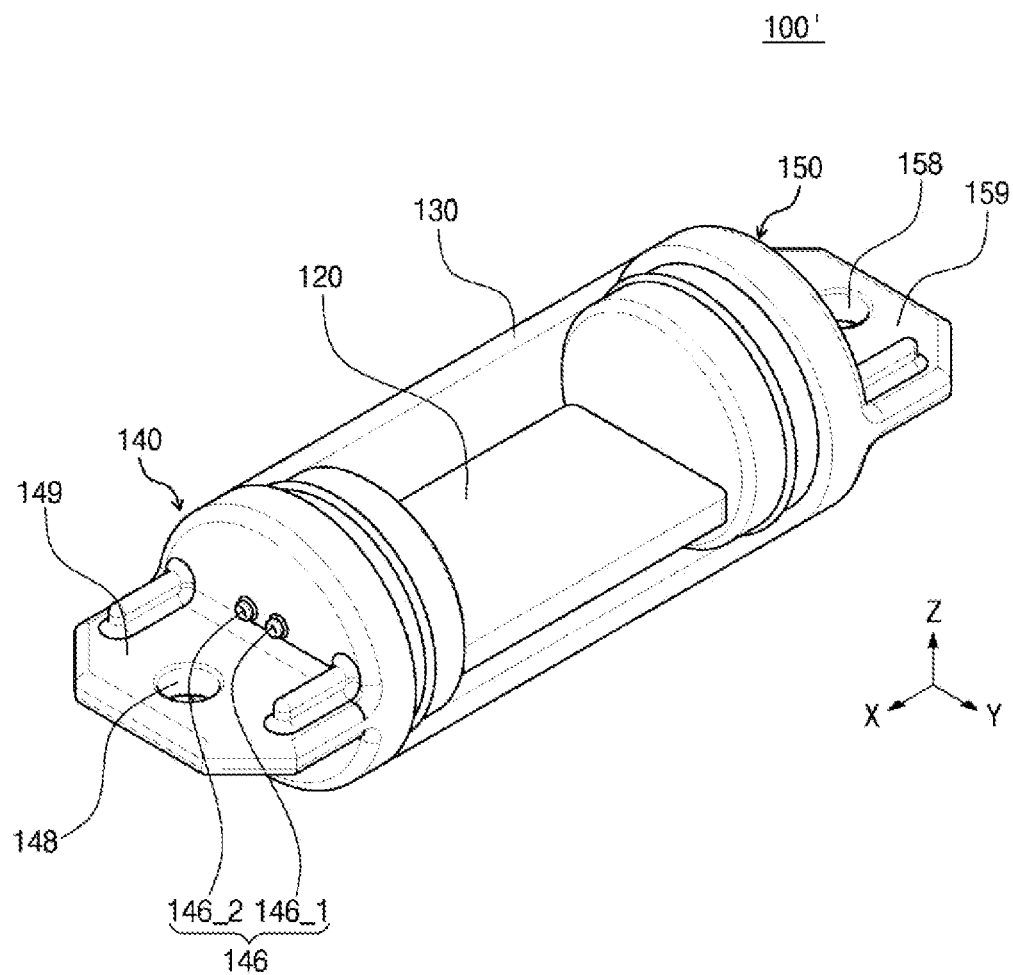
FIG. 13A and FIG. 13B are perspective views illustrating a sterilization module in different directions, according to another exemplary embodiment.
Figure 13B:
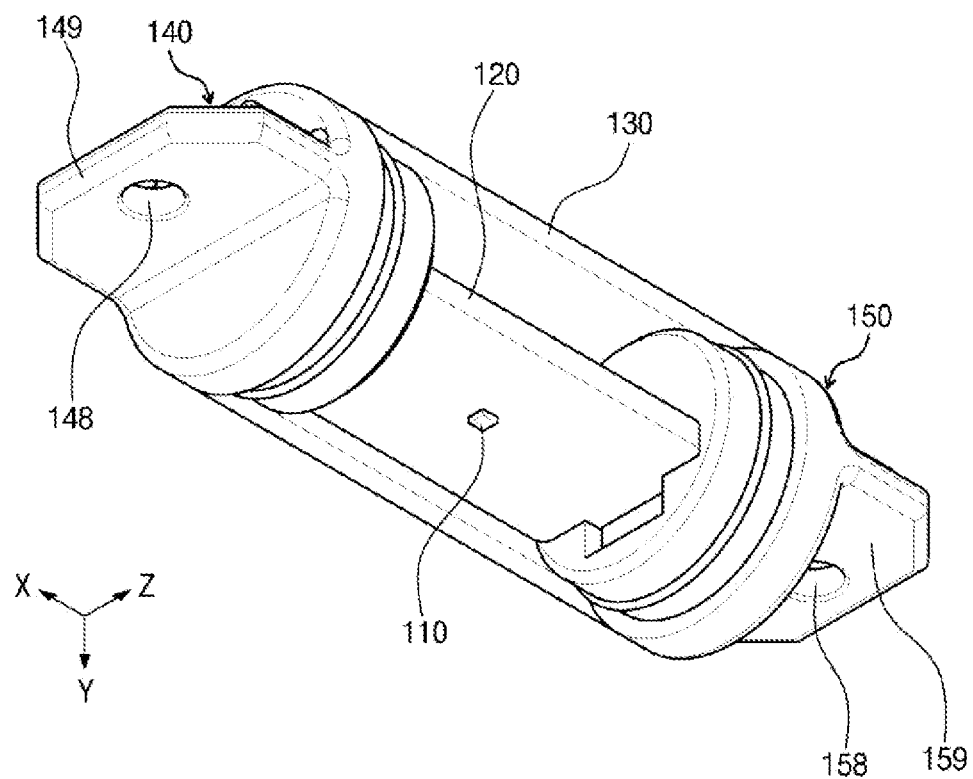

FIGS. 13A and 13B are perspective views illustrating a sterilization module 100' in different directions, according to another exemplary embodiment. The sterilization module 100' of FIGS. 13A and 13B is similar to the sterilization module 100 of FIG. 1. Accordingly, identical or similar components are indicated using the same or similar reference numerals, and thus, repeated descriptions thereof will be omitted below.

Referring to FIGS. 13A and 13B, the sterilization module 100' includes the light source 110, the board 120, the protective tube 130, the first base 140, and the second base 150.

Unlike the sterilization module 100 of FIG. 1, the bases 140 and 150 of the sterilization module 100' of FIGS. 13A and 13B further include coupling parts 149 and 159, respectively. For example, the first base 140 extends along the first direction, and includes the first coupling part 149 integrally formed with the first cover part, the second base 150 is connected along the first direction and includes the second coupling part 159 integrally formed with the second cover part. First and second coupling holes 148 and 158 are formed in the first and second coupling parts 149 and 159, respectively.

As such, the first and second coupling parts 149 and 159 may be formed in the first and second bases 140 and 150, respectively, and thus, the sterilization module 100' according to an exemplary embodiment may be easily installed on each side surface of the reservoir 10. Hereinafter, the sterilization module 100' installed in the reservoir 10 according to exemplary embodiments will be described in more detail.

Figure 14A:
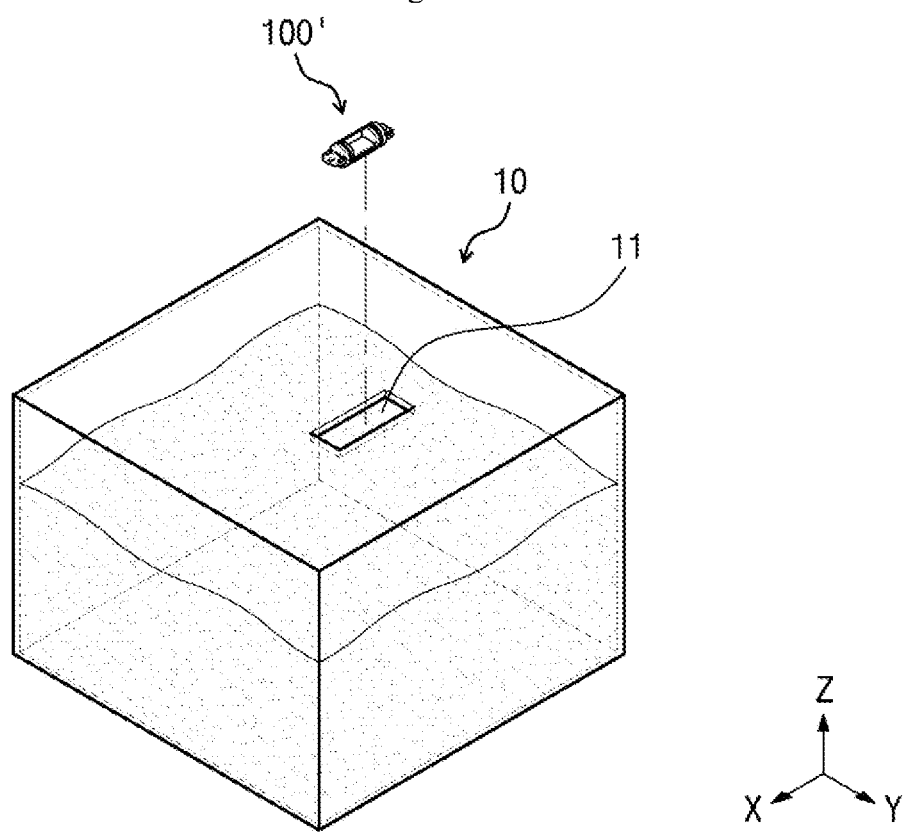
FIG. 14A and FIG. 14B are views illustrating a sterilization module of FIGS. 13A and 13B installed in a reservoir.
Figure 14B:
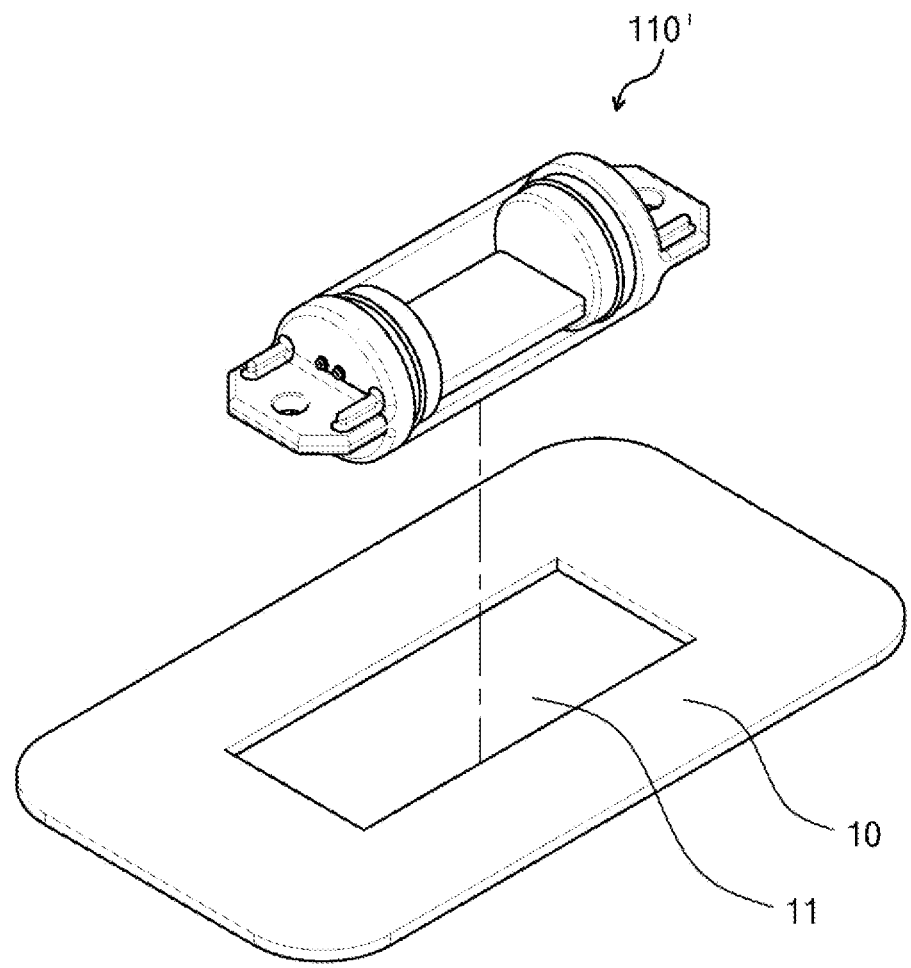
Figure 14C:
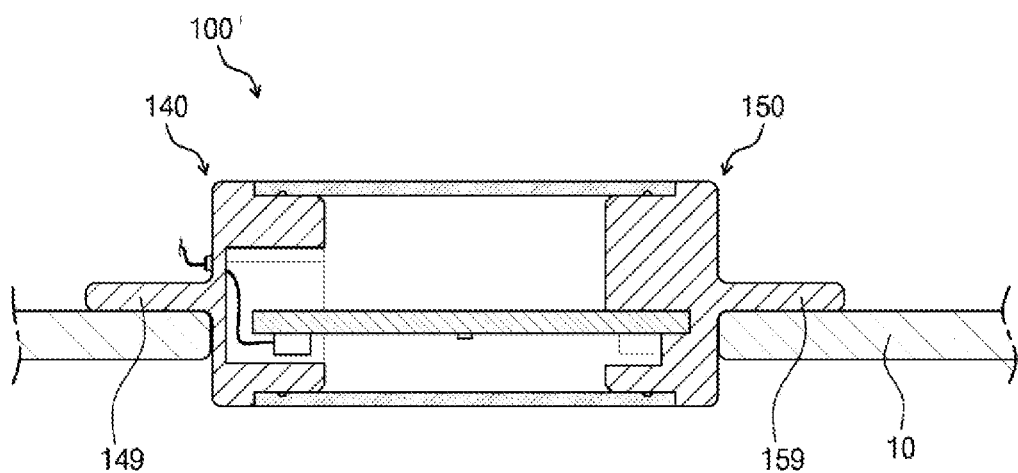
FIG. 14C, FIG. 14D, and FIG. 14E are cross-sectional views illustrating a sterilization module installed in a reservoir.
Figure 14D:
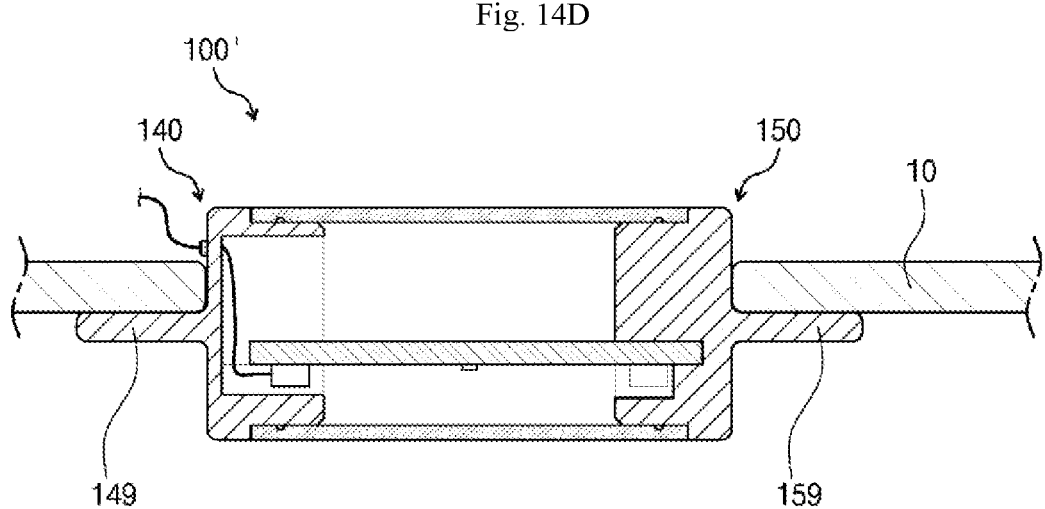
Figure 14E:
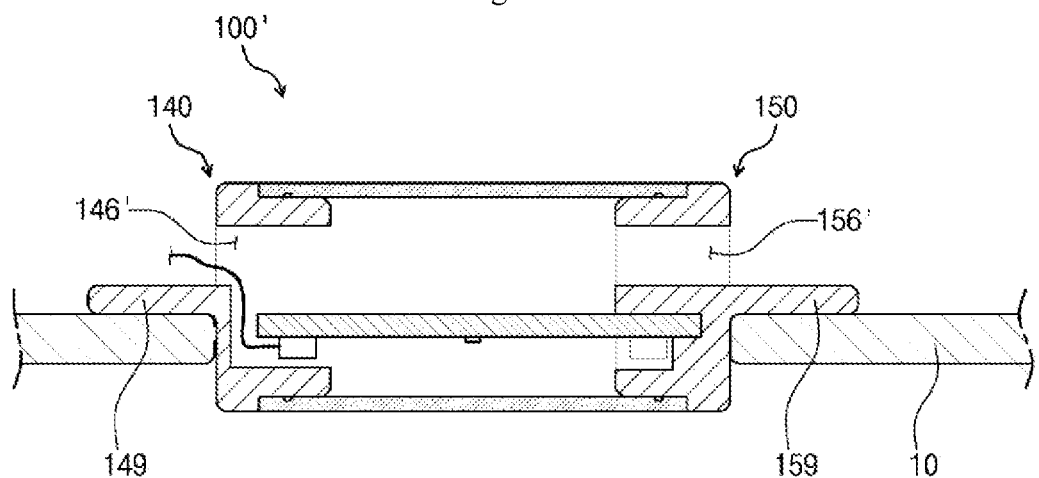

FIGS. 14A and 14B are views illustrating the sterilization module 100' of FIGS. 13A and 13B installed in the reservoir 10. FIGS. 14C to 14E are cross-sectional views illustrating the sterilization module 100' installed in the reservoir 10. In FIG. 14B, only the part of the reservoir is exemplarily illustrated for convenience of description.

Referring to FIGS. 14A and 14B, the installation hole 11 is formed on at least one surface of the reservoir 10. The sterilization module 100' is installed to cover the installation hole 11. In this case, for the purpose of preventing the leakage between the installation hole 11 and the sterilization module 100', the installation hole 11 and the sterilization module 100' are installed to have shapes corresponding to each other.

For example, as described above, in the sterilization module 100' according to an exemplary embodiment, the base and the protective tube are coupled to each other without steps, and thus, the sterilization module 100' has a rectangular shape when viewed from above the plane. In this case, the installation hole 11 is formed to have a rectangular shape corresponding to the sterilization module 100'. As such, according to an exemplary embodiment, each of the sterilization module 100' and the installation hole 11 may be formed in a simple rectangular shape, and thus, the possibility of leakage between the sterilization module 100' and the installation hole 11 is reduced due to their simple shape.

According to an exemplary embodiment, the sterilization module 100' may be installed in the reservoir 10 in various manners. For example, as illustrated in FIG. 14B, the sterilization module 100' may be installed to cover the installation hole 11 (refer to FIG. 13) from the outside to the inside of the reservoir 10. As another example, as illustrated in FIG. 14C, the sterilization module 100' may be installed to cover the installation hole 11 from the inside to the outside of the reservoir 10.

In this case, in both FIG. 14B and FIG. 14C, the wire connected to the connector is drawn to the outside of the reservoir 10 via the through-hole 146. Accordingly, the water stored in the reservoir 10 may be prevented from being penetrated via the through-hole 146.

According to the illustrated exemplary embodiment, the through-hole 146 for drawing the wire connected to the connector is described as being less than or equal to the diameter of the wire. However, the inventive concepts are not limited thereto. For example, for the purpose of radiating heat generated from the light source to the outside, a through-opening greater than the diameter of the wire may be formed in at least one of the two bases of the sterilization module. In this manner, the heat inside the sterilization module 100' may be released to the outside via the through-opening, as well as the wire is drawn to the outside via the through-opening.

For example, as illustrated in FIG. 14E, through-openings 146' and 156' may be formed in the first and second bases 140 and 150 of the sterilization module 100', respectively. In particular, the first through-opening 146' is formed in the first base 140. As such, the heat inside the sterilization module 100' may be released to the outside, as well as drawing the wire connected to the connector to the outside. Furthermore, the second through-opening 156' is formed in the second base 150, and the internal heat may be released to the outside. In this case, each of the first and second through-openings 146' and 156' may be positioned at the outside of the reservoir 10, thereby preventing the water stored in the reservoir 10 from flowing into the sterilization module 100' via the first and second through-openings 146' and 156'.

However, the inventive concepts are not limited thereto. For example, the sterilization module according to other exemplary embodiments may be variously modified and applied.

Hereinafter, the modification and application examples of the sterilization module will be described in more detail with reference to the drawings.

Figure 15:
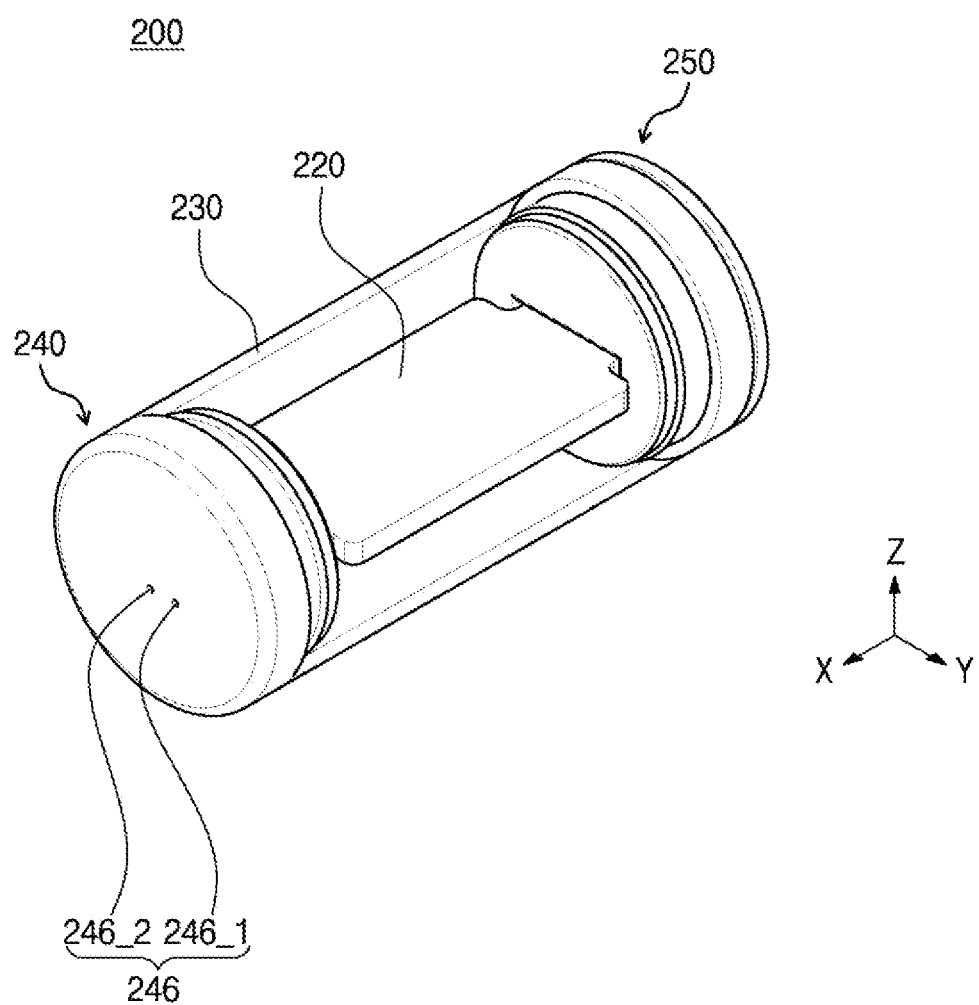
FIG. 15 and FIG. 16 are perspective views illustrating a sterilization module when viewed in different directions.
Figure 16:
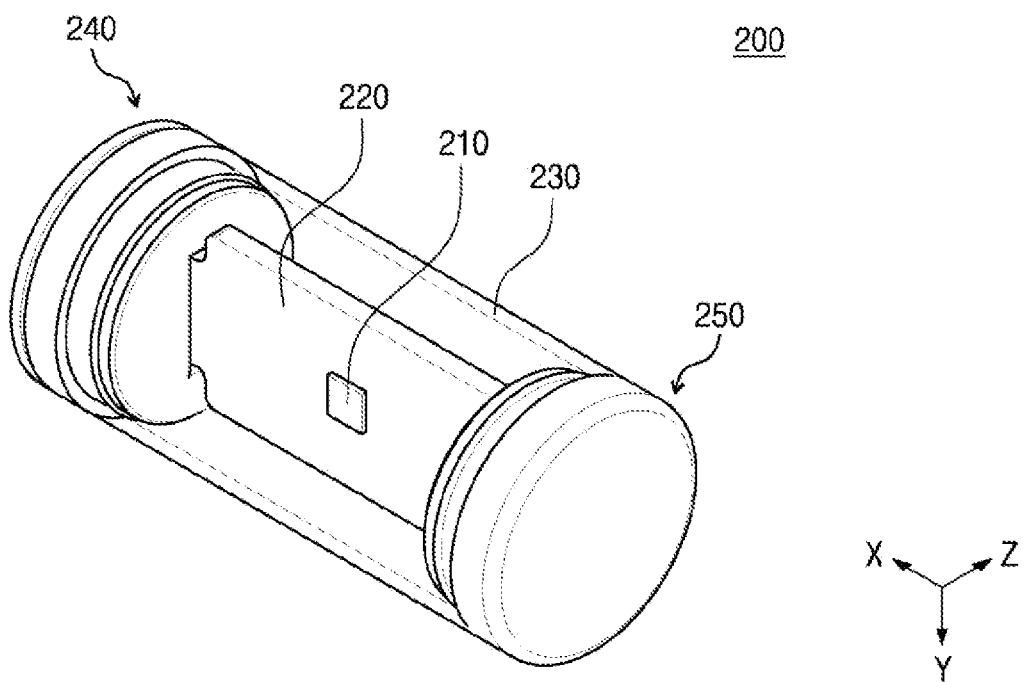
Figure 17:
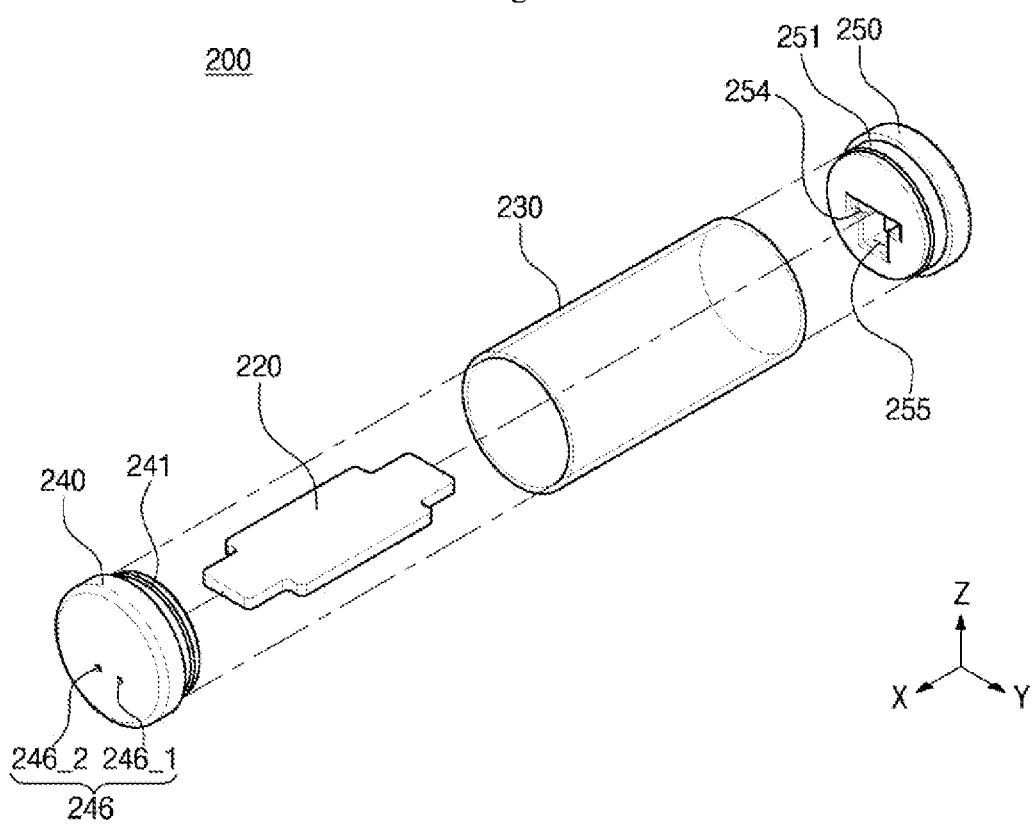
FIG. 17 is an exploded perspective view of a sterilization module.

FIGS. 15 to 17 are views illustrating a sterilization module 200 according to an exemplary embodiment. In particular, FIGS. 15 and 16 are perspective views illustrating the sterilization module 200 when viewed in different directions, respectively. FIG. 17 is an exploded perspective view of the sterilization module 200.

The sterilization module 200 of FIGS. 15 to 17 is similar to the sterilization module 100 of FIGS. 1 to 3. Accordingly, similar components will be indicated with similar reference numerals, and thus, repeated descriptions thereof will be omitted to avoid redundancy.

Referring to FIGS. 15 to 17, the sterilization module 200 includes a light source 210, a board 220, a protective tube 230, a first base 240, and a second base 250.

Similarly to the sterilization module 100 of FIGS. 1 to 3, the sterilization module 200 of FIGS. 15 to 17 includes the first and second bases 240 and 250. Each of the first and second bases 240 and 250 are coupled to the protective tube 230, so as not to have a step. As such, the sterilization module 200 of FIGS. 15 to 17 may be easily coupled to an external device, such as a reservoir, and may effectively perform a sterilization operation.

However, unlike the sterilization module 100 of FIGS. 1 to 3, the first base 240 and/or the second base 250 of the sterilization module 200 of FIGS. 15 to 17 do not include a separate withdrawal groove. That is, the fixation grooves 144_1 and 144_2, the receiving groove 145, and the withdrawal groove 147 are formed in the first base 140 described in FIGS. 1 to 3, however, only the fixation groove and the receiving groove are formed in the first base 240 of FIGS. 15 to 17, and the withdrawal groove is not formed. Furthermore, the through-hole 146 of FIGS. 1 to 3 is connected to the withdrawal groove 147, while a through-hole 246 of FIGS. 15 to 17 is connected to the receiving groove.

In this case, each of the ends of the board 220 may be coupled to be inserted into the fixation groove formed at the first base 240 of FIGS. 15 to 17, rather than a part thereof. Accordingly, the board 220 may be fixed more securely.

Figure 18A:
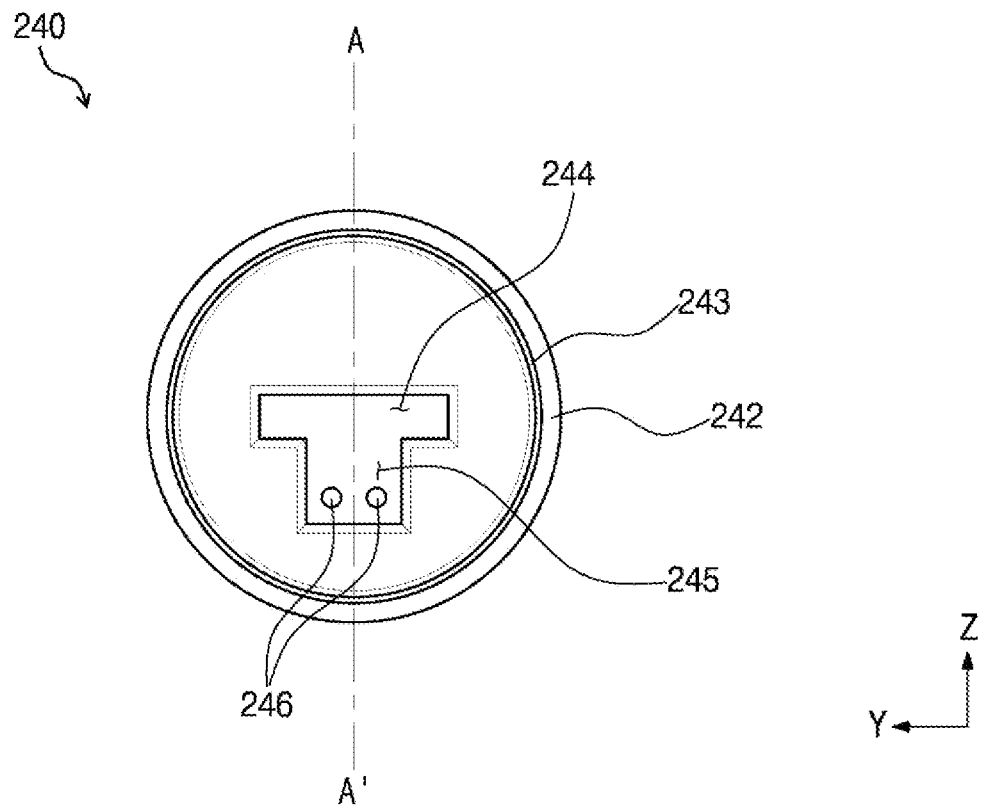
FIG. 18A is a plan view of a first base when viewed in a first direction.
Figure 18B:
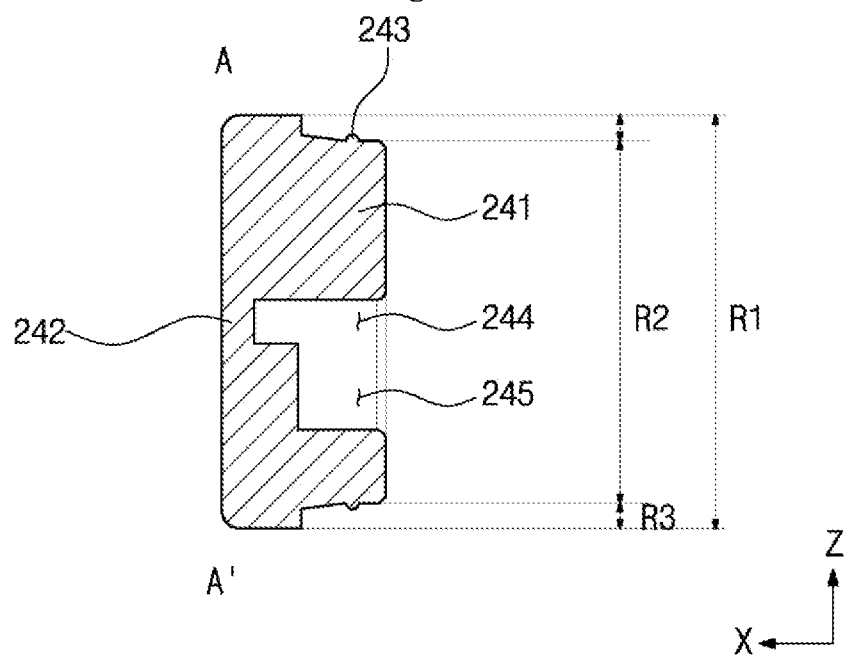
FIG. 18B is a cross-sectional view of a first base taken along line A-A' of FIG. 18A.

FIGS. 18A to 18B are views illustrating the first base 240 of FIGS. 15 to 17 in detail. In particular, FIG. 18A is a plan view of the first base 240 when viewed in the first direction. FIG. 18B is a cross-sectional view of the first base 240 taken along line A-A' of FIG. 18A.

Referring to FIGS. 18A and 18B, the first base 240 includes an insertion part 241 and a cover part 242.

The insertion part 241 is inserted into the inside of the protective tube 230, and is coupled to be inserted into the protective tube 230. For the purpose of being inserted inside the protective tube 230, the diameter R2 in the third direction of the insertion part 241 is less than the diameter R1 in the third direction of the protective tube 230. However, the inventive concept are not limited thereto, and in some exemplary embodiments, for the purpose of being coupled to be tightly inserted into the protective tube 230, the diameter R2 in the third direction of the insertion part 241 may be formed to be the same as the diameter R1 in the third direction of the protective tube 230.

A fixation groove 244 and a receiving groove 245 are formed in the insertion part 241. One end of the board 220 is fastened to the fixation groove 244 and is fixed, and a peripheral circuit, such as a connector, is accommodated in the receiving groove 245. A through-hole 246 is formed at the cover part 242, and the through-hole 246 is connected to the receiving groove 245. Accordingly, the wire connected to the peripheral circuit, such as a connector, is drawn to the outside via the receiving groove 245 and the through-hole 246.

Since the through-hole 246 is connected to the receiving groove 245, the through-hole 246 of FIGS. 18A and 18B are located at the lower portion of the extension surface with respect to the extension surface extending along the board 220 in the first direction. That is, as compared to the through-hole 146 formed in the first base 140 of FIGS. 9A to 9D positioned at the upper portion of the extension surface when viewed with respect to an extension surface extending along the board 120, the through-hole 246 of FIGS. 18A and 18B is located in the lower portion of the extension surface.

In this manner, since a separate withdrawal groove is not formed in the first base 240 according to an exemplary embodiment, each of the ends of the board 220 may be coupled to be inserted into the fixation groove 244 of the first base 240. Accordingly, the first base 240 according to an exemplary embodiment may support the board 220 more stably.

Figure 19A:
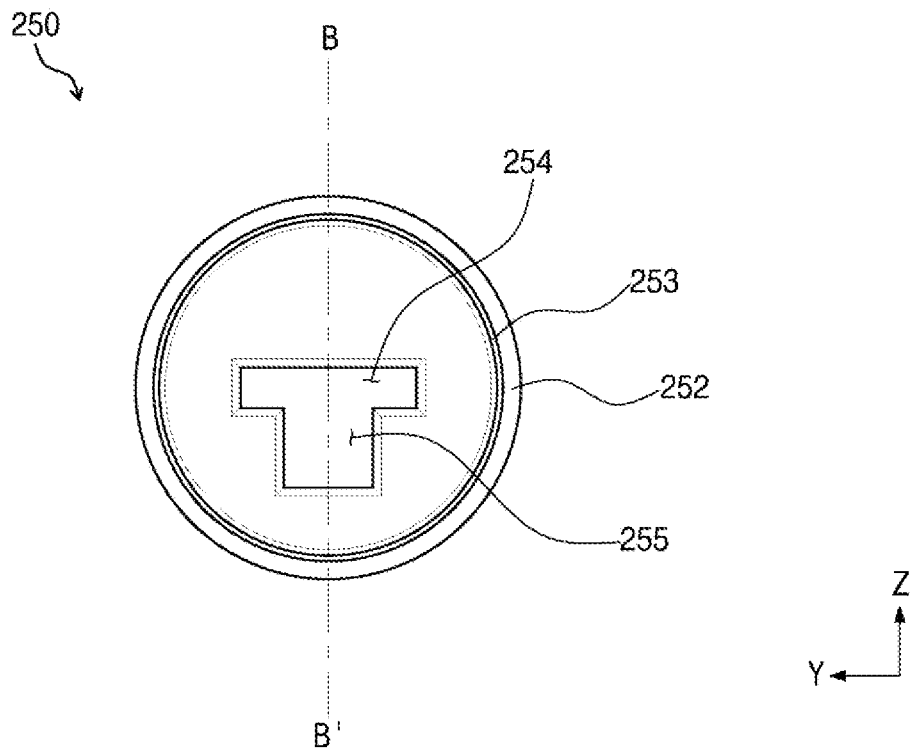
FIG. 19A is a plan view of a second base when viewed in a first direction.
Figure 19B:
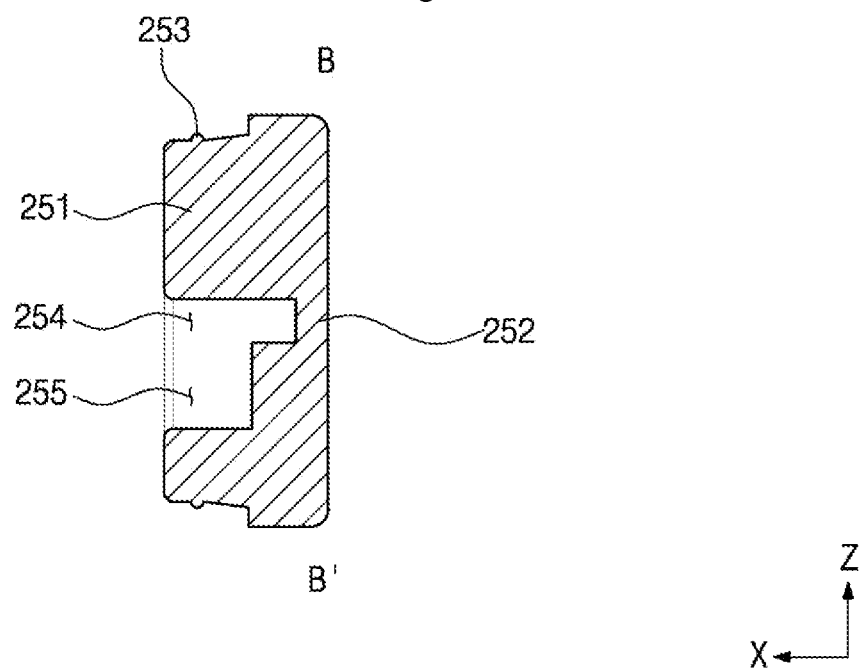
FIG. 19B is a cross-sectional view of a second base taken along line B-B' of FIG. 19A.

FIGS. 19A to 19B are views illustrating the second base 250 of FIGS. 15 to 17 in detail. In particular, FIG. 19A is a plan view of the second base 250 when viewed in the first direction. FIG. 19B is a cross-sectional view of the second base 250 taken along line B-B' of FIG. 19A.

Referring to FIGS. 19A and 19B, the second base 250 includes an insertion part 251 and a cover part 252. The insertion part 251 is inserted into the inside of the protective tube 230 and is coupled to be inserted into the protective tube 230. A fixation groove 254 and a receiving groove 255 are formed in the insertion part 251. The fixation groove 254 supports the board, and the receiving groove 255 provides the space for accommodating a peripheral circuit.

The structure, shape, or the like of the second base 250 illustrated in FIGS. 19A and 19B is similar to that of the first base 240 except that the through-hole 146 is not present. As such, repeated descriptions of substantially similar elements will be omitted below.

Figure 20A:
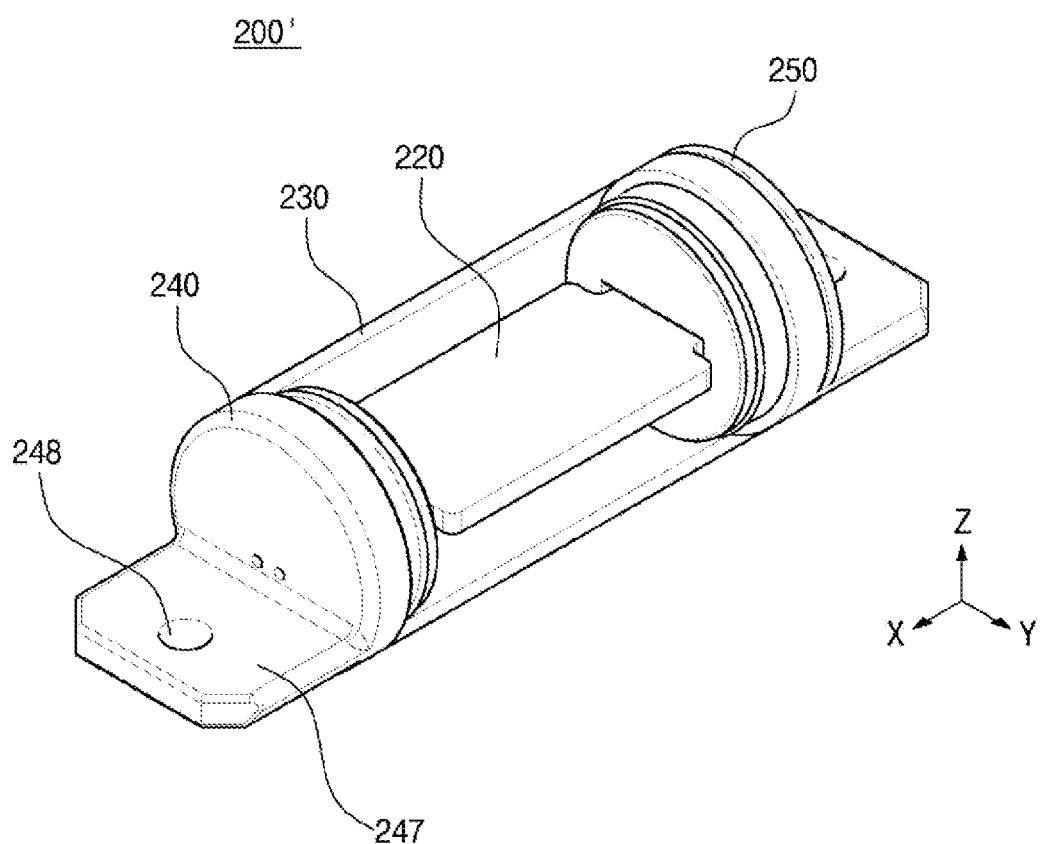
FIG. 20A and FIG. 20B are perspective views illustrating a sterilization module in different directions, according to another exemplary embodiment.
Figure 20B:
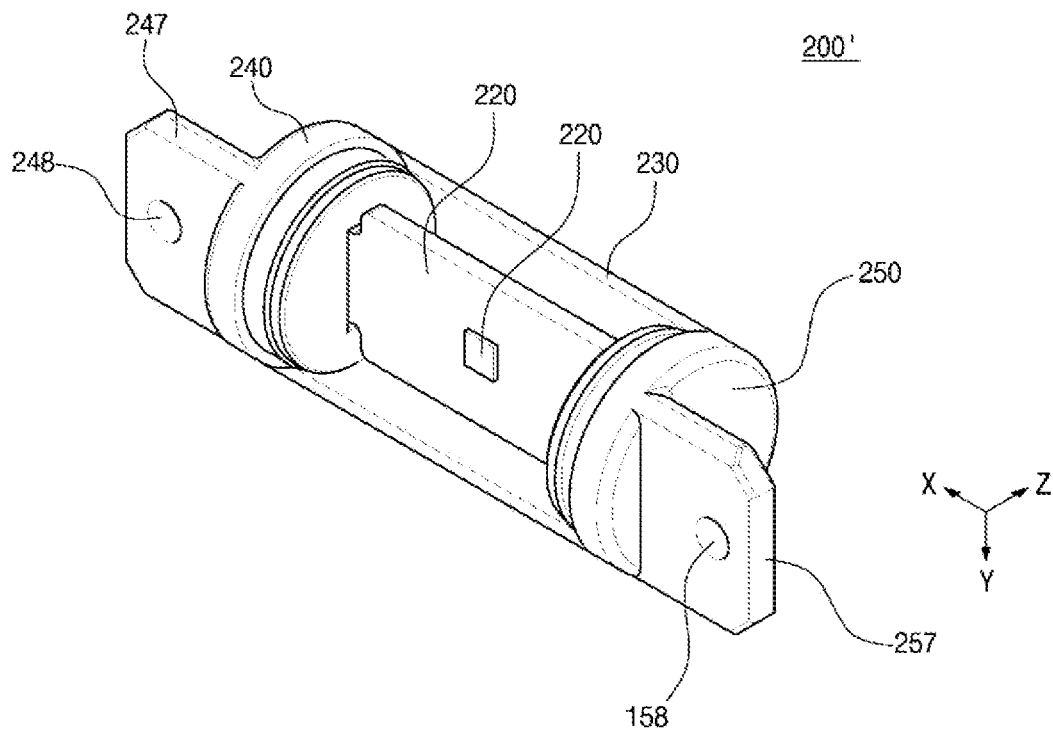

FIGS. 20A and 20B are perspective views illustrating a sterilization module 200' in different directions, according to another exemplary embodiment. The sterilization module 200' of FIGS. 20A and 20B is similar to the sterilization module 200 of FIGS. 15 to 17. Accordingly, identical or similar components are indicated using the same or similar reference numerals, and thus, repeated descriptions thereof will be omitted below.

Referring to FIGS. 20A and 20B, the sterilization module 200' includes the light source 210, the board 220, the protective tube 230, the first base 240, and the second base 250.

Unlike the sterilization module 200 of FIGS. 15 to 17, the bases 140 and 150 of the sterilization module 200' of FIGS. 20A and 20B further include coupling parts 247 and 257, respectively. For example, the first base 240 extends along the first direction, and includes the first coupling part 247 integrally formed with the first cover part. The second base 250 is connected along the first direction, and includes the second coupling part 257 integrally formed with the second cover part. First and second coupling holes 248 and 258 are formed in the first and second coupling parts 247 and 257, respectively.

As such, the first and second coupling parts 247 and 257 may be formed in the first and second bases 240 and 250, respectively, and thus, the sterilization module 200' according to an exemplary embodiment may be easily installed in an external device, such as a reservoir.

Figure 21A:
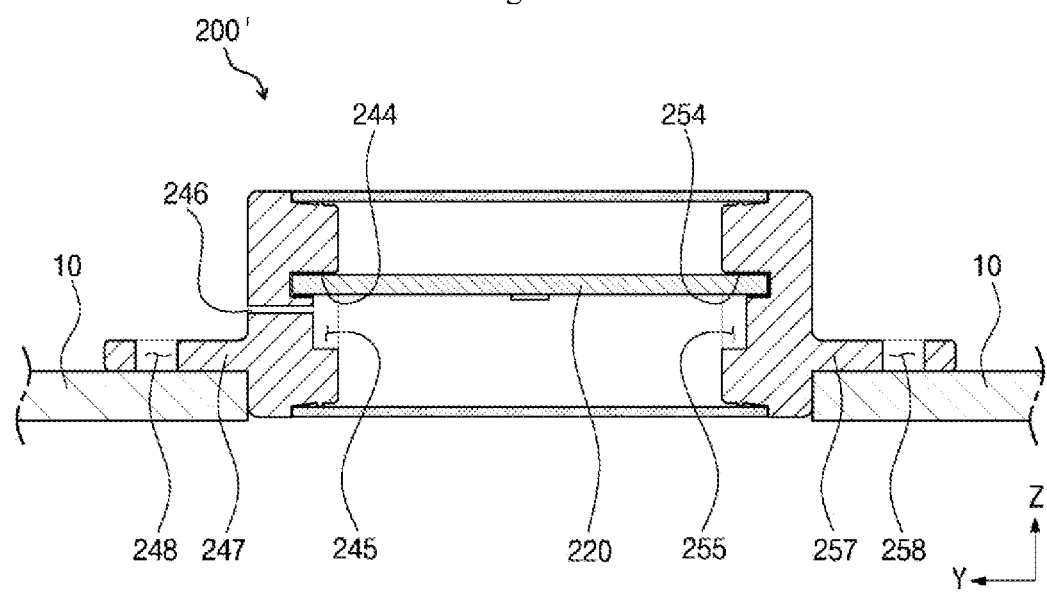
FIG. 21A, FIG. 21B, and FIG. 21C are cross-sectional views illustrating a sterilization module installed in a reservoir according to an exemplary embodiment.
Figure 21B:
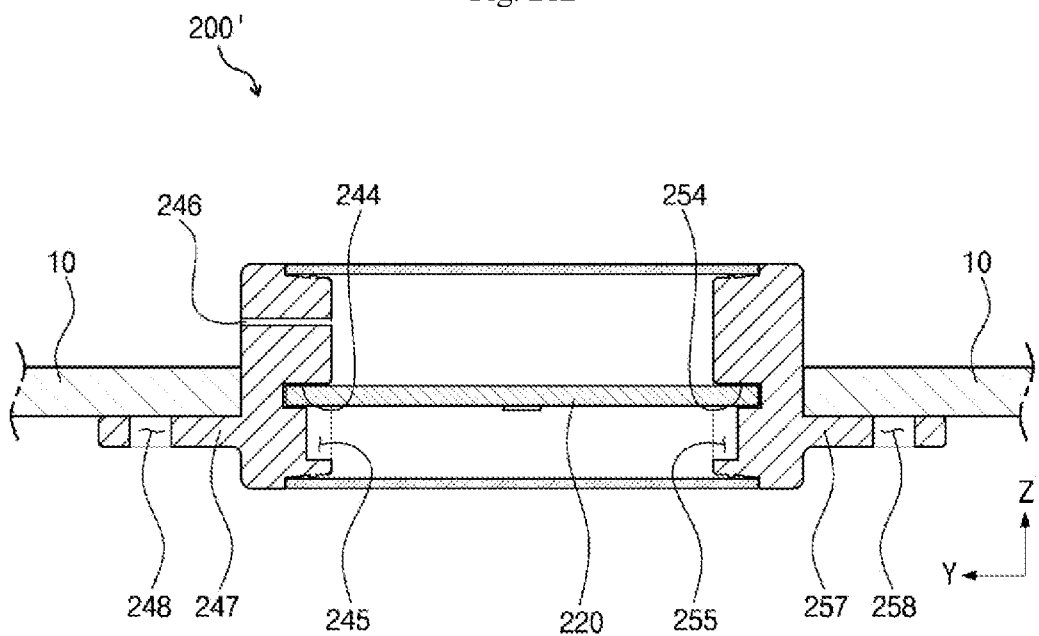
Figure 21C:
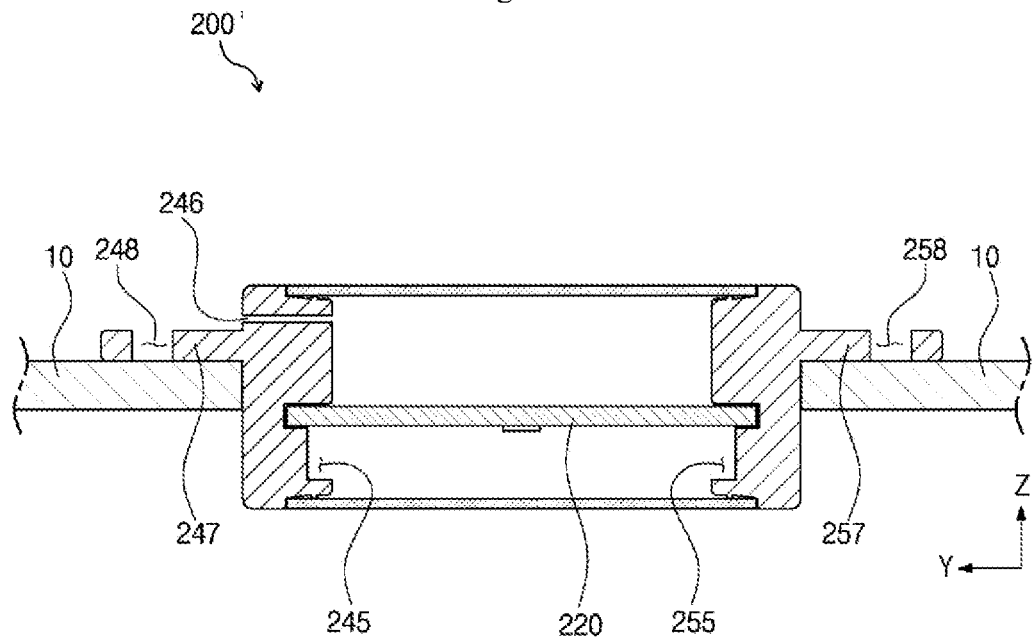

FIGS. 21A to 21C are cross-sectional views illustrating the sterilization module 200' installed in the reservoir 10.

Referring to FIG. 21A, the sterilization module 200' is installed to cover an installation hole from the outside of the reservoir 10 toward the inside of the reservoir 10. In this case, the first base 240 has a through-hole 246 that is penetrated in the first direction, and the through-hole 246 is positioned at the outside of the reservoir 10.

In more detail, each of the through-hole 246 and the first and second coupling parts 247 and 257 are positioned on an extension surface extending along the board 220 in the first direction to prevent the water inside the reservoir 10 from being penetrated via the through-hole 246.

In this case, the spaced distance in the third direction between the through-hole 246 and the extension surface is formed to be shorter than the spaced distance in the third direction between the extension surface and the first and second coupling parts 247 and 257. In other words, the first extension surface extending along the through-hole 246 in the first direction is positioned between the second extension surface extending along the board 220 in the first direction and the third extension surface extending along the first and second coupling parts 247 and 257 in the first direction.

As such, the through-hole 246 is formed to be positioned outside the reservoir 10, thereby preventing the water inside the reservoir 10 from being penetrated into the sterilization module 100 via the through-hole 246.

Referring to FIG. 21B, the sterilization module 200' may be installed to cover the installation hole from the inside of the reservoir 10 in the outside direction. In this case, the first base 240 may have the through-hole 246 that is penetrated in the first direction, and the through-hole 246 may be positioned at the outside of the reservoir 10.

In more detail, when viewed with respect to the extension surface extending along the board 120 in the first direction, the extension surface may be positioned between the through-hole 246 and the first and second coupling parts 247 and 257. That is, the through-hole 246 is located outside the reservoir 10, and the first and second coupling parts 247 and 257 may be positioned inside the reservoir 10.

In this case, an element, such as a connector, may be mounted on the back surface of the board 220, such that the wire is drawn more easily via the through-hole 246 positioned in the direction of the back surface of the board 220. That is, the board 220 may be a double-sided board. An element, such as a connector, may be mounted on the back surface of the board 220, and the light source 210 may be mounted on the front surface of board 220.

Referring to FIG. 21C, the sterilization module 200' may be installed to cover the installation hole from the outside of the reservoir 10 in the inside direction. Furthermore, in this case, the first and second coupling parts 247 and 257 may be installed in the upper portion of the first and second bases 240 and 250, such that the sterilization module 200' is deeply installed in the inside of the reservoir 10.

In more detail, each of the first and second coupling parts 247 and 257 are fastened to the outer side of the reservoir 10. The through-hole 246 is formed to be positioned outside the reservoir 10. In this case, as illustrated in FIG. 21C, the first extension surface extending along the board 220 in the first direction is positioned between the second extension surface extending along the through-hole 246 in the first direction and the third extension surface extending along the first and second coupling parts 247 and 257 in the first direction.

In this case, an element, such as a connector, may be mounted on the back surface of the board 220, such that the wire is drawn more easily via the through-hole 246 positioned in the direction of the back surface of the board 220. That is, the board 220 may be a double-sided board. An element, such as a connector, may be mounted on the back surface of the board 220, and the wire may be drawn to the outside through the first and second through-holes 146 and 156.

FIGS. 22 to 25 are views for describing a sterilization module 300 according to an exemplary embodiment.

Figure 22:
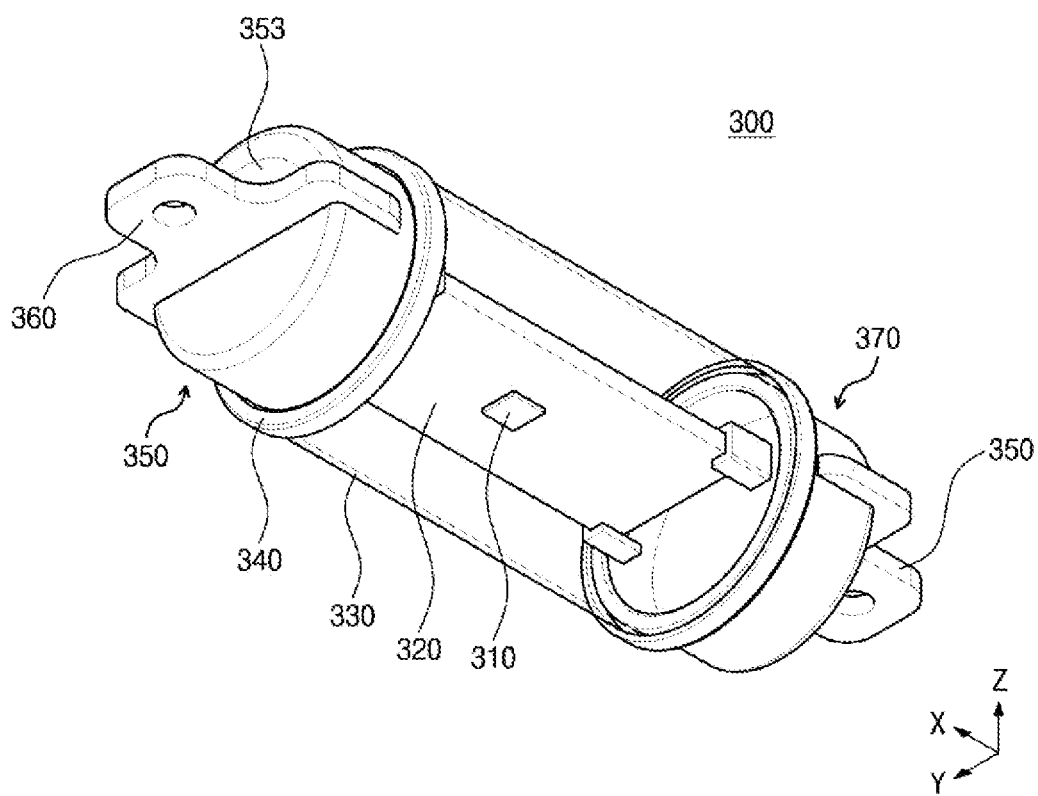
FIG. 22 is a perspective view illustrating a sterilization module according to an exemplary embodiment.
Figure 23:
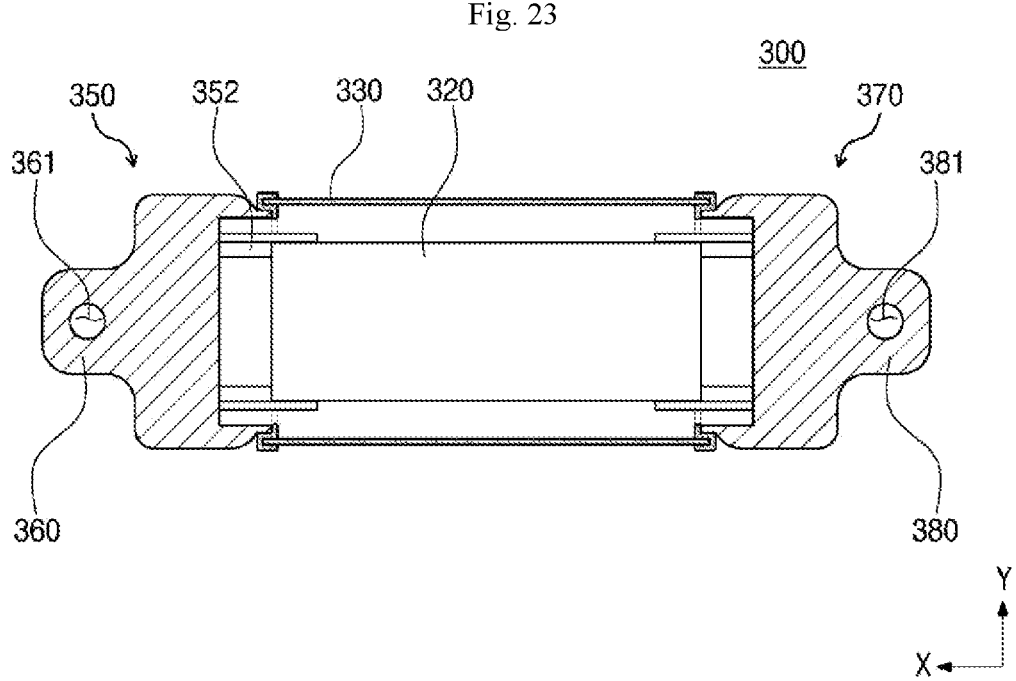
FIG. 23 is a plan view of a sterilization module.
Figure 24:
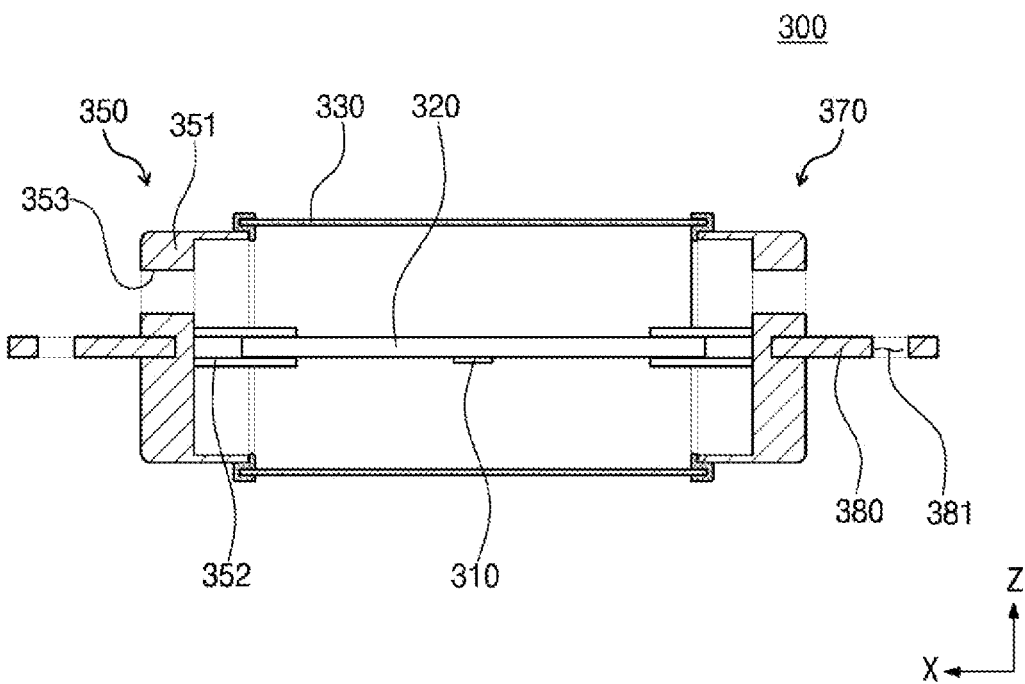
FIG. 24 is a cross-sectional view of a sterilization module.
Figure 25:
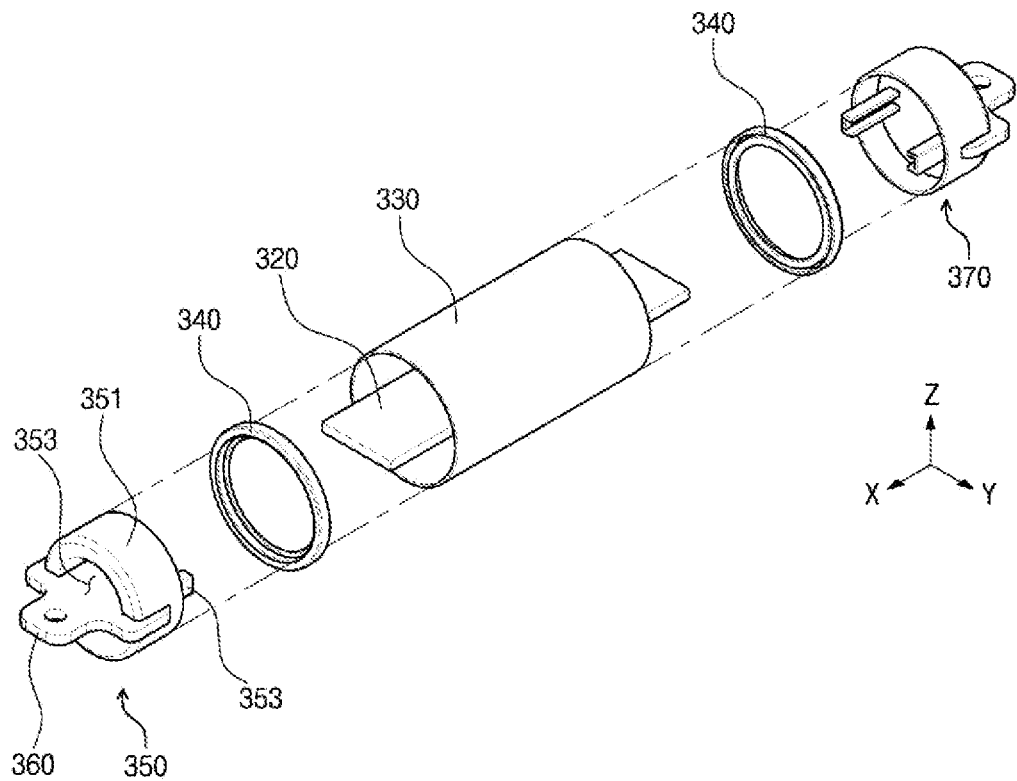
FIG. 25 is an exploded perspective view of a sterilization module.

FIG. 22 is a perspective view illustrating the sterilization module 300 according to an exemplary embodiment. FIG. 23 is a plan view of the sterilization module 300. FIG. 24 is a cross-sectional view of the sterilization module 300. FIG. 25 is an exploded perspective view of the sterilization module 300.

The sterilization module 300 of FIGS. 22 to 25 is similar to the above-described sterilization module 100 or 200. Accordingly, the same or similar components will be described using the same or similar reference numeral, and thus, repeated descriptions thereof will be omitted below.

Referring to FIGS. 22 to 25, the sterilization module 300 includes a light source 310, a board 320, a protective tube 330, a sealing part 340, a first base 350, a first coupling part 360, a second base 370, and a second coupling part 380.

Unlike the above-described sterilization module 100 or 200, the sterilization module 300 according to an exemplary embodiment includes the rectangular board 320, and has a support guide 352 for supporting the board 320. That is, in the above-described sterilization module 100 or 200, the board is coupled to be inserted into the fixation groove recessed from the surface of the base, and thus, the board is fixed. On the other hand, in the sterilization module 300 of FIGS. 22 to 25, the board is fixed via the support guide 352 formed in the first base 350.

Also, the base of the above-described sterilization module 100 or 200 is coupled to the protective tube without steps. n the other hand, there is a step between the base 350 or 370 of the sterilization module 300 of FIGS. 22 to 25 and the protective tube 330. Accordingly, the sterilization module 300 may be installed in the customized reservoir including an installation hole corresponding to the shape of the sterilization module 300 to perform a sterilization operation.

In more detail, the light source 310 emits UV light and may be mounted on the board 320. The protective tube 330 is formed to surround the light source 310 and the board 320, and both ends of the protective tube 330 are coupled to be inserted into the base 350 or 370.

The sealing part 340 is positioned between the protective tube 330 and the bases 350 and 370, and prevents moisture from being penetrated into the sterilization module 300. For example, the sealing part 340 may be formed of an elastic body having a predetermined elasticity as a soft material, such as an O-ring. Thermoplastic resin, thermosetting resin, silicone resin, or the like may be used as the elastic body. The shape of the sealing part 340 according to an exemplary embodiment will be described in more detail below.

The bases 350 and 370 are provided at both ends in the length direction of the board 320, respectively. A receiving space for accommodating the board 320, more specifically, the end portion of the board 320 is formed in each of the bases 350 and 370.

The coupling parts 360 and 380 are provided at both ends of the sterilization module 300. For example, the coupling part 360 are formed along the length direction of the board 320. A coupling groove 361 for fastening the sterilization module 300 to a reservoir or the like is provided in a part of the coupling part 360.

For example, the coupling part 360 may be integrally formed with the base 350 by performing insert-injection into the base 350 provided by an injection molding scheme. As such, the coupling part 360 are integrally formed with the base 350, and thus, the number of parts is reduced. In addition, the process of assembling the coupling part 360 and the base 350 is eliminated, thereby reducing the process and costs of manufacturing the sterilization module 300.

Refer to FIGS. 22 to 25, for the purpose of accommodating the board 320 and the protective tube 330 and drawing a power line to the outside, the base 350 includes a cap 351, the support guide 352, and an outlet 353.

The cap 351 is formed in a cylindrical shape to protect the board 320 and the protective tube 330 accommodated inside the base 350. The cap 351 is formed to have an inner diameter greater than the outer diameter of the protective tube 330, so as to be inserted into the protective tube 330. The sealing part 340 is interposed between the cap 351 and the protective tube 330.

The support guide 352 is coupled to be inserted into the board 320. In this manner, the support guide 352 corresponds to a structure that supports the board 320 on the base 350 to constrain the movement of the board 320. For example, the support guide 352 may include a rib and a coupling groove. The rib may be formed to protrude inside the base 350, in which the receiving space is formed. The rib is formed to protrude in a direction in parallel with the width direction of the board 320. A pair of ribs is provided inside the base 350 to face each other in a direction in parallel with the protrusion direction of the rib.

The coupling groove is formed to be concave inside the rib. The end of the board 320 is inserted into the coupling groove to be capable of being slid. The insertion coupling between the board 320 and the support guide 352 is made through the insertion of the board 320.

The board 320 may be supported on the base 350 by the insertion coupling between the board 320 and the support guide 352, so as to constrain the movement of the board 320 in the thickness direction (hereinafter referred to as "vertical direction").

The outlet 353 is formed to penetrate the end of the base 350, and to expose the receiving space inside the base 350. The wire electrically connected to the board 320 may be exposed to the outside through the outlet. The externally exposed wire may be connected to a connector (not illustrated) or power supply device, and may supply power to the board 320 and the light source 310 mounted on the board 320.

Moreover, the outlet 353 may release the heat generated during emission of UV light to the outside, thereby preventing the temperature of the sterilization module 300 from being raised more than necessary. In some exemplary embodiments, for example, a pore may be additionally formed in the base 350 in addition to the outlet, such that the generated heat may be more efficiently discharged to the outside through the pore.

FIGS. 26 to 29 are cross-sectional views illustrating the sealing part 340 of the sterilization module 300 in more detail.

In FIGS. 26 to 29, only the cap 351 of the base 350, the protective tube 330, and the sealing part 340 disposed between the cap 351 of the base 350 and the protective tube 330 are exemplarily illustrated.

As illustrated in FIGS. 26 to 29, the sealing part 340 may be implemented in various forms to prevent external moisture from being penetrated between the protective tube 330 and the base 350.

Figure 26:
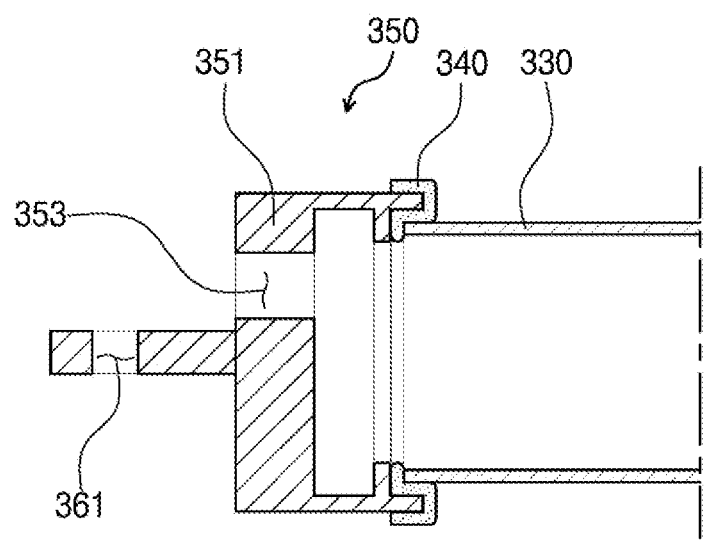
FIG. 26, FIG. 27, FIG. 28, and FIG. 29 are cross-sectional views for illustrating a sealing part of a sterilization module in more detail.

For example, as illustrated in FIG. 26, the sealing part 340 is implemented to have the shape of a rack, and one end of the cap 351 may be configured to be inserted into the rack. In this case, a stepped part is formed at the end of the cap 351. One end of the sealing part 340 may be implemented to be interposed between the stepped part and the protective tube 330.

Figure 27:
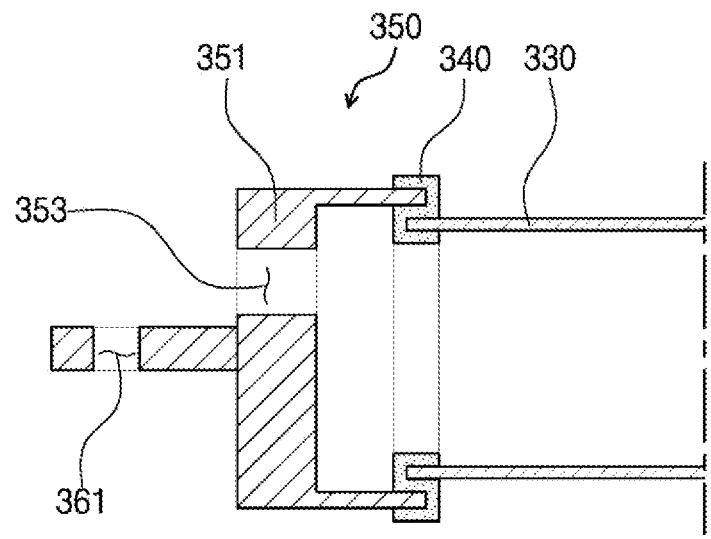

As another example, as illustrated in FIG. 27, both ends of the sealing part 340 are implemented to have a rack shape. The cap 351 is inserted into the rack formed at one end of the sealing part 340. The protective tube 330 may be implemented to be inserted into the rack formed at the other end of the sealing part 340. The sealing part 340 may be implemented to have a rigid sealing structure, thereby improving the waterproof performance of the sterilization module 300.

Figure 28:
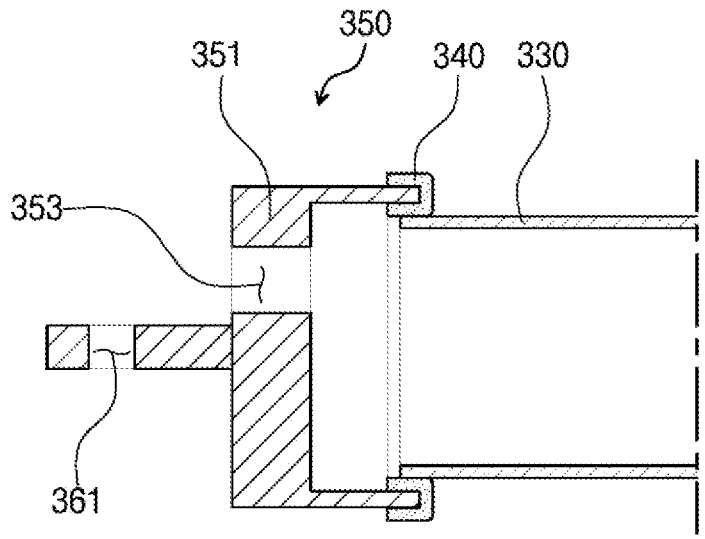
Figure 29:
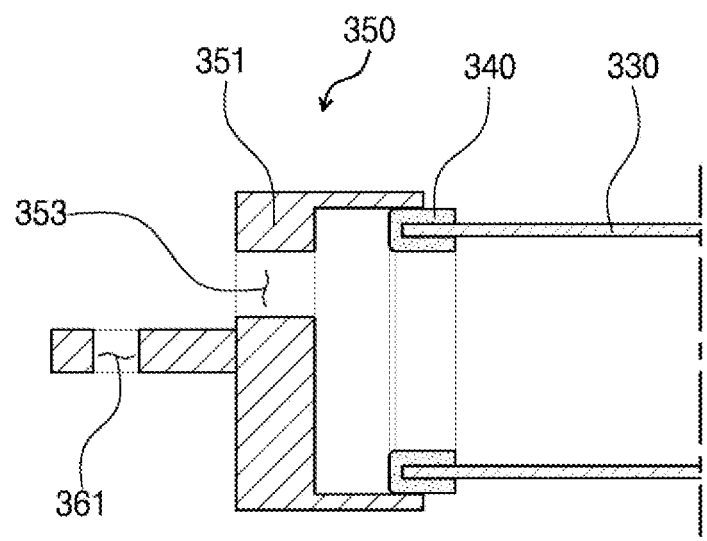

In an exemplary embodiment, as illustrated in FIGS. 28 and 29, the sealing part 340 may be implemented in a simpler form. For example, as illustrated in FIG. 28, the sealing part 340 may be interposed between the cap 351 and the protective tube 330. The sealing part 340 may be implemented to have a rack shape capable of wrapping one end of the cap 351. As another example, as illustrated in FIG. 29, the sealing part 340 may be interposed between the cap 351 and the protective tube 330. The sealing part 340 may be implemented to have a rack shape capable of wrapping one end of the protective tube 330.

As described above, the sterilization module 300 according to an exemplary embodiment is implemented to be easily fastened to a reservoir, thereby facilitating installment and replacement of the sterilization module 300. Furthermore, since the sterilization module 300 has a waterproof function to block the external moisture from being penetrated into the sterilization module 300, there is little risk of failure even when the sterilization module 300 is installed in a reservoir. In addition, the part of the sterilization module 300 is exposed to the inside of a reservoir, when the sterilization module 300 is installed in the reservoir or the like, and thus, the distance between a light source and water is shortened, thereby increasing sterilization efficiency.

Hereinafter, other examples of the sterilization module 300 according to an exemplary embodiment will be described in more detail below.

Figure 30:
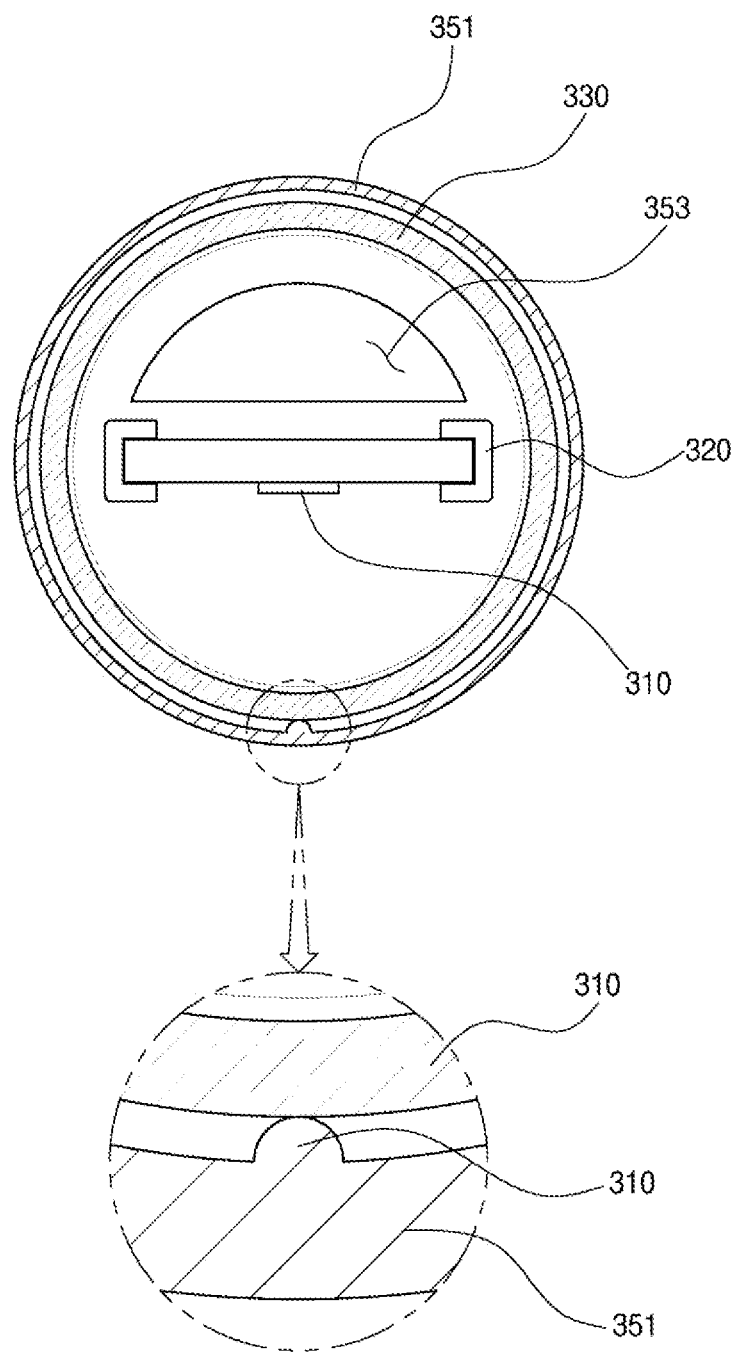
FIG. 30 is a cross-sectional view illustrating a coupling between a base and a protective tube according to another exemplary embodiment.

FIG. 30 is a cross-sectional view illustrating a coupling between the base 350 and the protective tube 330 according to another exemplary embodiment.

As illustrated in FIG. 30, the sterilization module 300 according to an exemplary embodiment may further include a protrusion 380. The protrusion 380 is formed to protrude on the inside of the base 350, more particularly, the inner peripheral surface of the protective tube mount.

According to an exemplary embodiment, the protrusion 380 is formed to protrude so as to be interposed between the cap 351 and the protective tube 330. The protrusion 380 is formed to protrude so as to overlap with the protective tube 330 coupled to be inserted into the inside of the base 350. Accordingly, the bonding force between the base 350 and the protective tube 330 may be increased.

Figure 31:
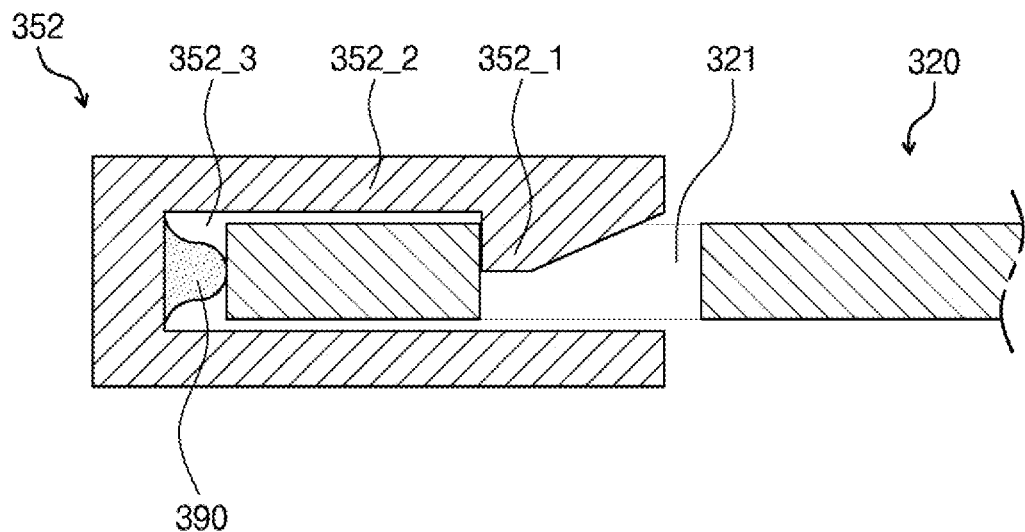
FIG. 31 is a cross-sectional view illustrating a coupling between a support guide and a board according to another exemplary embodiment.

FIG. 31 is a cross-sectional view illustrating a coupling between the support guide 352 and the board 320 according to another exemplary embodiment.

Referring to FIG. 31, the sterilization module 300 according to an exemplary embodiment may further include a configuration for improving the coupling force between the support guide 352 and the board 320.

More particularly, a latching groove 321 is formed in the portion of the board 320 inserted into a coupling groove 352_3, and a hook 352_1 is included in the support guide 352.

The latching grooves 321 are formed in both ends of the board 320, which are portions inserted into the coupling groove 352_3, respectively. The latching groove 321 may be formed to penetrate into the board 320, and may be formed to have a concave shape.

Moreover, the hook 352_1 is formed to have a shape protruding toward the coupling groove 352_3 from a rib 352_2 at the support guide 352, more particularly, the end of the rib 352_2. Furthermore, the rib 352_2, in which the hook 352_1 is formed, may be provided such that elasticity in the vertical direction is changed.

When the board 320 is completely inserted into the coupling groove 352_3, the provided hook 352_1 is inserted into the latching groove 321 and then fixes the board 320 to the support guide 352. That is, as the hook 352_1 is inserted into the latching groove 321, when the board 320 receives an external force in a direction, in which the board 320 deviates from the support guide 352, the interference occurs between hook 352_1 and board 320. As such, the board 320 may be tightly fixed to the support guide 352 while the forward and backward movement of the board 320 is constrained.

In addition, by the coupling between the hook 352_1 and the latching groove 321 described above, a preliminary coupling between the board 320 and the base 350 may take place simply by inserting the board 320 into the support guide 352, thereby improving the convenience of assembling the product and shortening the time required for assembling the product.

The sterilization module 300 according to an exemplary embodiment may further include an elastic member 390. The elastic member 390 may be provided in a spring form having elasticity, such as a coil spring and a leaf spring. The elastic member 390 is installed to be supported on the inner wall surface of the support guide 352, in which the coupling groove 352_3 is formed, and provides the forward and backward pressing force.

The elastic member 390 tightly contacts the contact surface between the hook 352_1 and the board 320 by providing the pressing force for tightly contacting the board 320, into which the hook 352_1 is inserted, with the hook 352_1. The board 320 may be more tightly coupled to the support guide 352 without dangling inside the support guide 352 by the operation of the elastic member 390.

Figure 32:
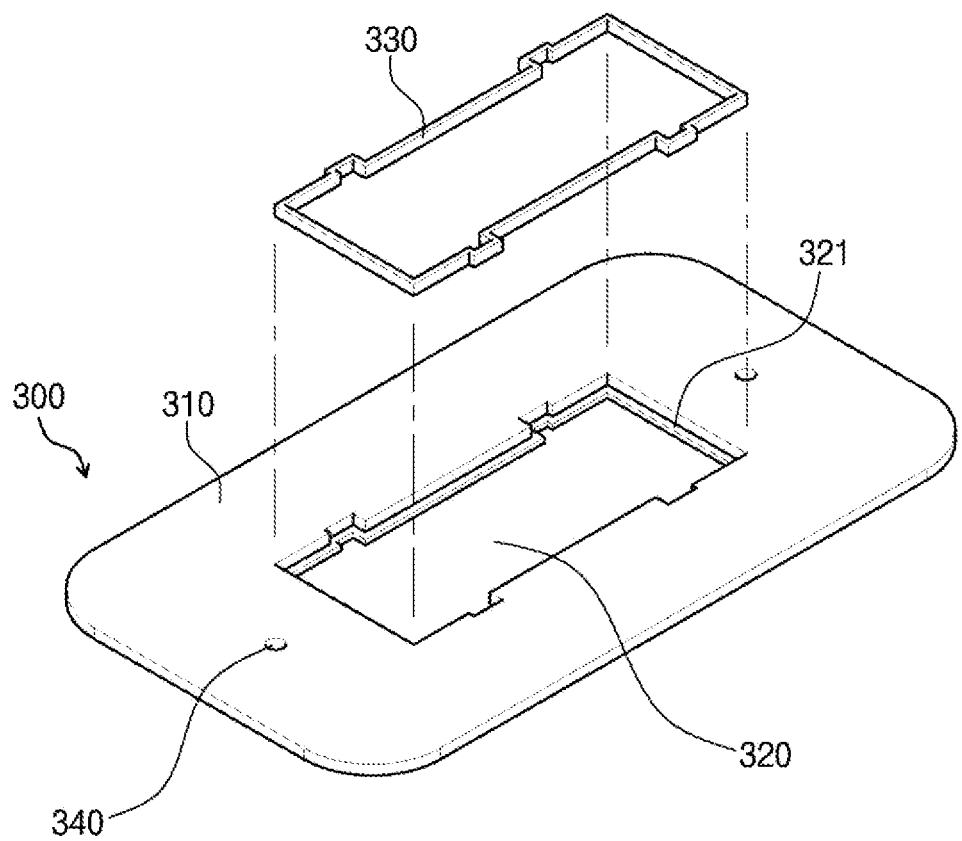
FIG. 32 is a view illustrating an exploded perspective view of a reservoir cover according to an exemplary embodiment.

FIG. 32 is a view illustrating an exploded perspective view of a reservoir cover 400 according to an exemplary embodiment. The reservoir cover 400 of FIG. 32 may be one surface of a reservoir, and may be an independent cover for shielding the reservoir, of which the upper surface is opened.

The reservoir cover 400 of FIG. 32 may be implemented to have a shape for accommodating the sterilization module 300 of FIG. 22. Referring to FIG. 32, the reservoir cover 400 includes a cover 410 and a sealing part 430.

The cover 410 is to shield the reservoir, of which the upper surface is opened, from the outside and includes a sterilization module mounting groove 420 for accommodating the sterilization module 300 of FIG. 22 in the center of the cover 410. The sterilization module mounting groove 420 may have a shape corresponding to the sterilization module 300 of FIG. 22. A stepped part 421 for stably seating the sealing part 430 or the sterilization module 300 of FIG. 22 may be formed in the lower portion. A coupling hole 440 corresponding to a coupling hole 361 of the coupling part 360 of FIG. 22 is provided in both ends of the cover 410.

The sealing part 430 may have a shape corresponding to the sterilization module 300 of FIG. 22. For example, the sealing part 430 may be seated on the stepped part 421 to accommodate the sterilization module 300, or may be coupled to be inserted into the sterilization module mounting groove 420 to accommodate the sterilization module 300.

Figure 33:
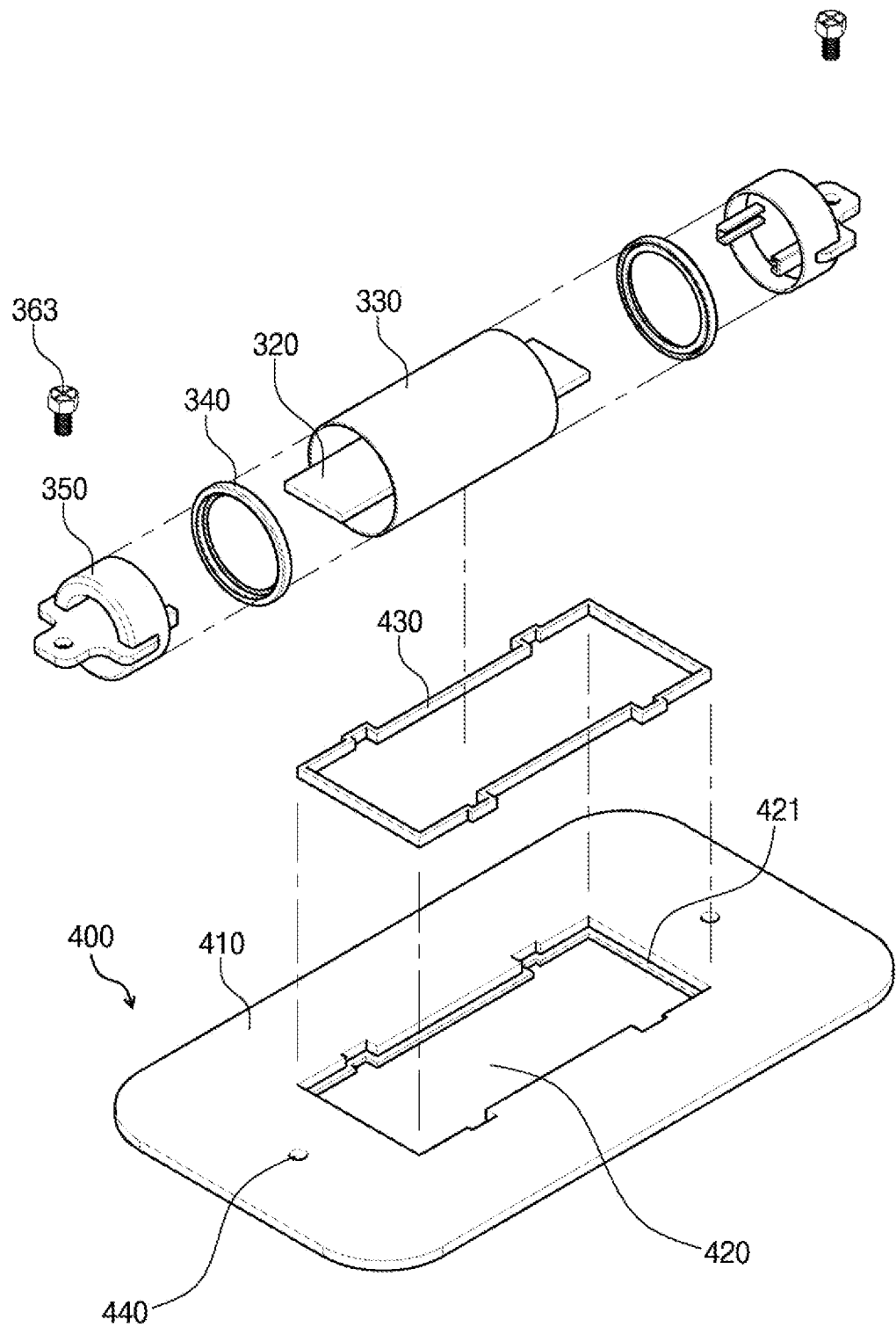
FIG. 33 is an exploded perspective view illustrating a sterilization module of FIG. 22 coupled to a reservoir cover of FIG. 32.
Figure 34:
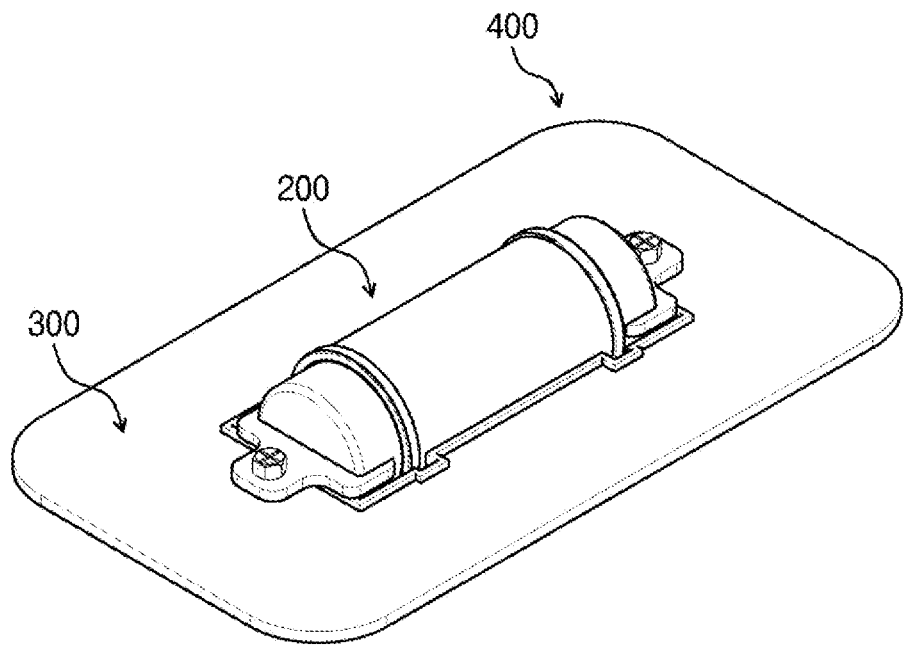
FIG. 34 is a perspective view illustrating a sterilization module mounted in a reservoir cover.

FIG. 33 is an exploded perspective view illustrating the sterilization module 300 of FIG. 22 coupled to the reservoir cover 400 of FIG. 32. FIG. 34 is a perspective view illustrating the sterilization module 300 mounted in the reservoir cover 400.

As illustrated in FIGS. 33 and 34, the sterilization module 300 may be installed in the reservoir cover 400. In this case, a part of the sterilization module 300 may be installed to be exposed in the direction of the bottom of the reservoir cover 400, and a part of the sterilization module 300 may be installed to be exposed in the direction of the top of the reservoir cover 400.

In this case, because one surface of the sterilization module 300, in which the light source 310 is installed, is exposed in the direction of the bottom of the reservoir cover 400, the sterilization module 300 may sterilize water stored in a reservoir.

Figure 35:
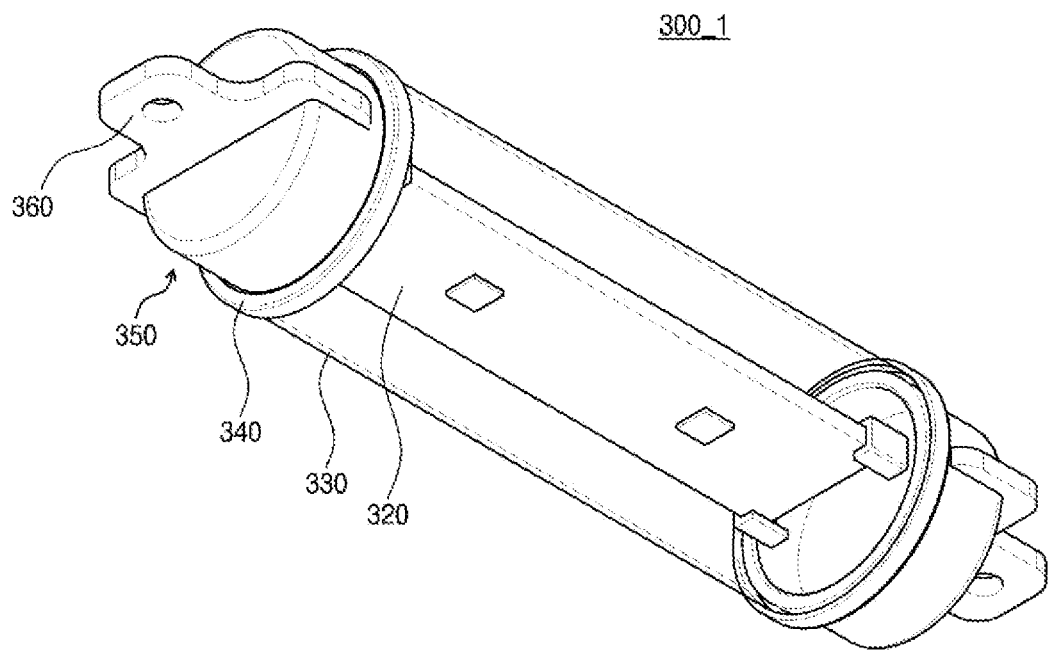
FIG. 35 is a view illustrating a sterilization module according to another exemplary embodiment.

FIG. 35 is a view illustrating a sterilization module 300_1 according to another exemplary embodiment. The sterilization module 300_1 of FIG. 35 is similar to the sterilization module 300 of FIG. 22. Accordingly, the same or similar components will be described using the same or similar reference numeral, and thus, repeated descriptions thereof will be omitted.

Unlike the sterilization module 300 of FIG. 22, a plurality of light sources are mounted on the board of the sterilization module 300_1 of FIG. 35. That is, an the sterilization module of FIG. 22 has the single light source 310 mounted on the board 320, while the sterilization module 300_1 of FIG. 35 includes a plurality of light sources.

The sterilization module 300 described above may be used for various devices necessary for sterilization. Hereinafter, application examples of the sterilization module 300 will be described in more detail.

Figure 36:
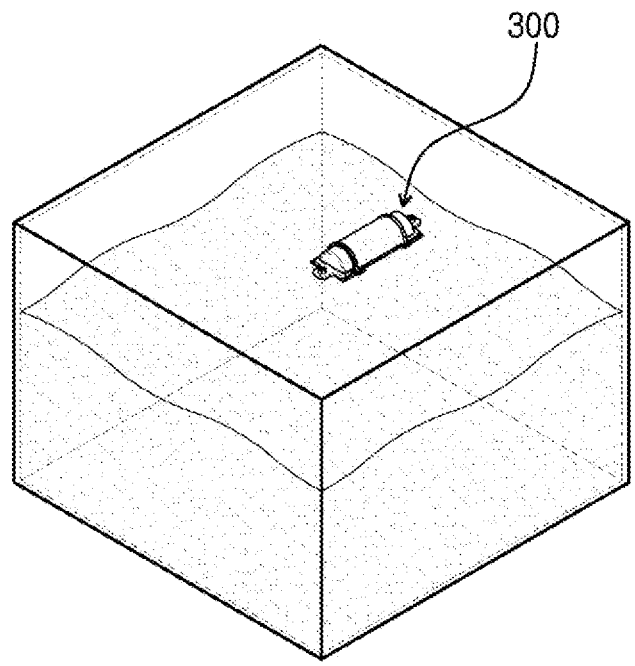
FIG. 36 and FIG. 37 are views illustrating a water purification device according to an exemplary embodiment.
Figure 37:
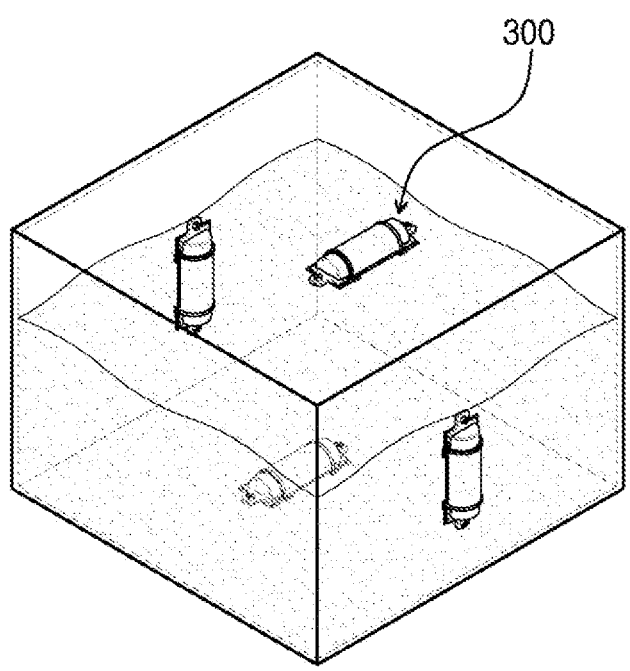

FIGS. 36 and 37 are views illustrating a water purification device according to an exemplary embodiment.

Referring to FIG. 36, a water purification device 1000 includes a reservoir, a reservoir cover covering the reservoir, and the sterilization module 300 assembled on the reservoir cover. The sterilization module 300 emits UV light in the internal direction of the reservoir, and the water stored in the reservoir is sterilized by the sterilization module 300.

FIG. 36 exemplarily illustrates that the water purification device 1000 includes a single sterilization module 300 on one surface of the reservoir cover. However, the inventive concepts are not limited thereto, and in some exemplary embodiments, a plurality of sterilization modules 300 may be provided. Although not illustrated in FIG. 36, for example, two, three, or more sterilization modules 300 may be provided to the reservoir cover. The number of sterilization modules 300 may be variously changed depending on the size of the reservoir, the shape of the reservoir, and the amount of water to be sterilized.

According to an exemplary embodiment, the sterilization module 300 may be mounted at various locations. FIG. 36 shows that the sterilization module 300 is mounted in the reservoir cover. However, the inventive concepts are not limited thereto, and the sterilization module 300 may be provided at various locations. The sterilization module 300 according to an exemplary embodiment has a waterproof effect, and thus, the sterilization module 300 may also be provided at a location where the sterilization module 300 directly contacts water.

Referring to FIG. 37, the sterilization module 300 according to an exemplary embodiment may be mounted on not only the reservoir cover of the upper surface of the reservoir, but also either the side wall or the bottom of the reservoir. Even though the sterilization module 300 is mounted on any wall of the reservoir, a part of the outer peripheral surface of the protective tube mounted in the sterilization module 300 is exposed to the inside of the reservoir with respect to the reservoir wall, and the other part of the outer peripheral surface of the protective tube is exposed outside of the reservoir.

Figure 38:
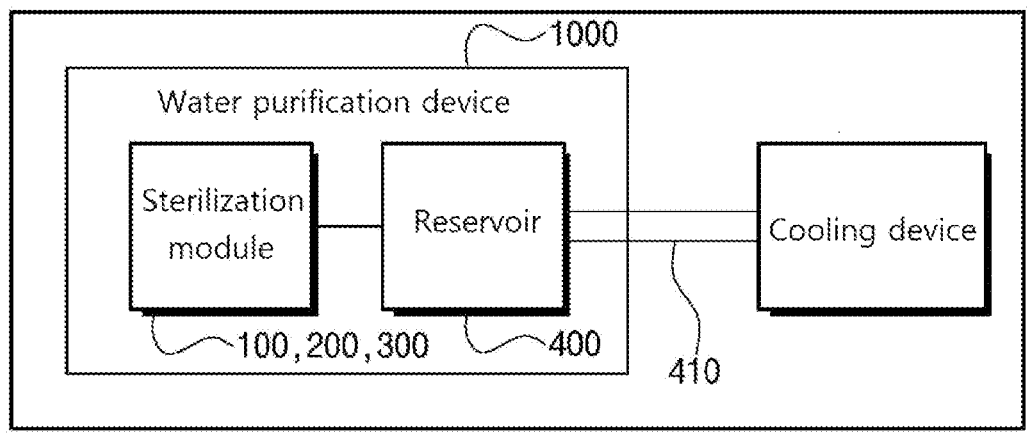
FIG. 38 is a block diagram illustrating a water purification system according to an exemplary embodiment.

FIG. 38 is a block diagram illustrating a water purification system 3000 according to an exemplary embodiment.

Referring to FIG. 38, the water purification system 3000 including the water purification device 1000 includes the water purification device 1000, a drain pipe 410, and a cooling device. For example, the water purification system 3000 including the water purification device 1000 may be a cooling system, such as an ice maker.

According to an exemplary embodiment, the water purification system 3000 including the water purification device 1000 may purify the water entered from the outside through the water purification device 1000. In this case, the water purification device 1000 allows the sterilization module 100, 200, or 300 to sterilize the water entered into the reservoir 400 and to purify the water. The purified water flows from the water purification device 1000 to a cooling device 600 via the drain pipe 410. The purified water is cooled in the cooling device 600 to become an ice, and the ice is stored inside the water purification system 300 including the water purification device 1000 or discharged to the outside.

According to an exemplary embodiment, the drain pipe 410 is a passage through which water flows. The drain pipe 410 is connected to the reservoir 400 of the water purification device 1000. Furthermore, the drain pipe 410 is connected to the cooling device 600.

FIG. 38 shows that the reservoir 400 and the cooling device 600 are connected via the drain pipe 410. However, in some exemplary embodiments, another device may be present between the reservoir 400 and the cooling device 600. Also, the flow of water between different devices in the cooling system may also be achieved via the drain pipe 410.

Figure 39:
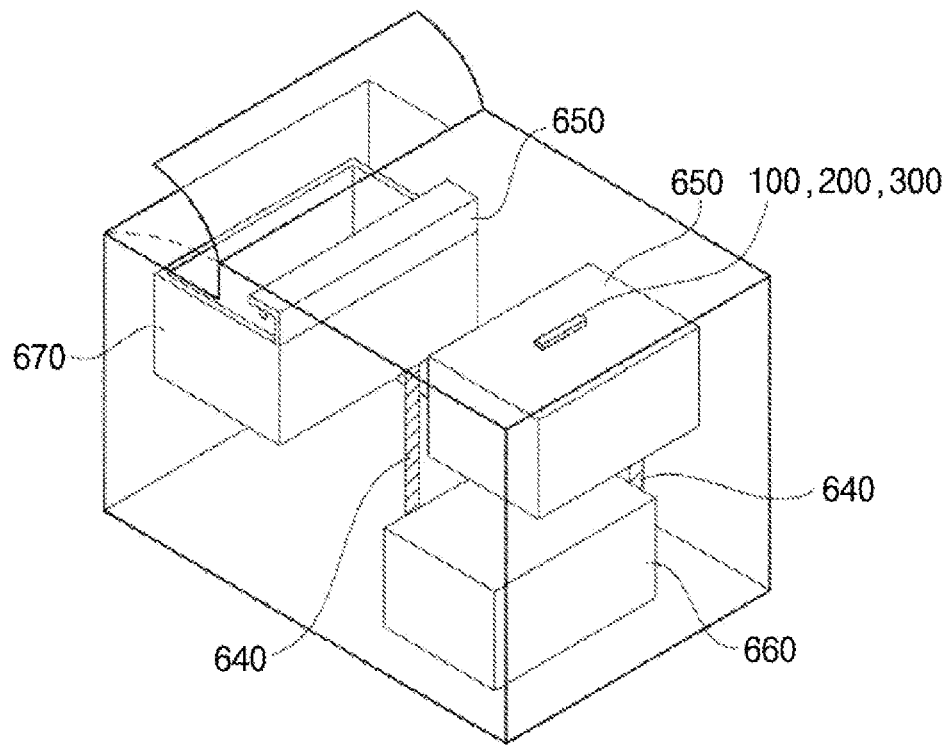
FIG. 39 is an view illustrating a cooling system according to an exemplary embodiment.

FIG. 39 is an exemplary view illustrating a cooling system 4000 according to an exemplary embodiment.

Referring to FIG. 39, the cooling system 4000 includes the water purification device 1000 including the sterilization module 100, 200, or 300, a cold water device 660, a cooling device 650, and a storage device 670. According to an exemplary embodiment, the water purification device 1000 sterilizes the water stored in the reservoir through the sterilization module 100, 200, or 300 to purify the water.

The water purified by the water purification device 1000 is supplied to the cold water device 660. The water purified by the cold water device 660 is cooled and then becomes cold water. The cold water of the cold water device 660 is supplied to the cooling device 650. The cold water becomes an ice in the cooling device 650. The ice generated by the cooling device 650 is stored in the storage device 670. At this time, when the water flows between the water purification device 1000, the cold water device 660, and the cooling device 650, the water may flow through a drain pipe 640. The cooling device 650 according to an exemplary embodiment operates in a manner as in a conventional cooling device. Furthermore, various ice making and deicing methods well known in the art may be applied to the cooling device 650.

Figure 40:
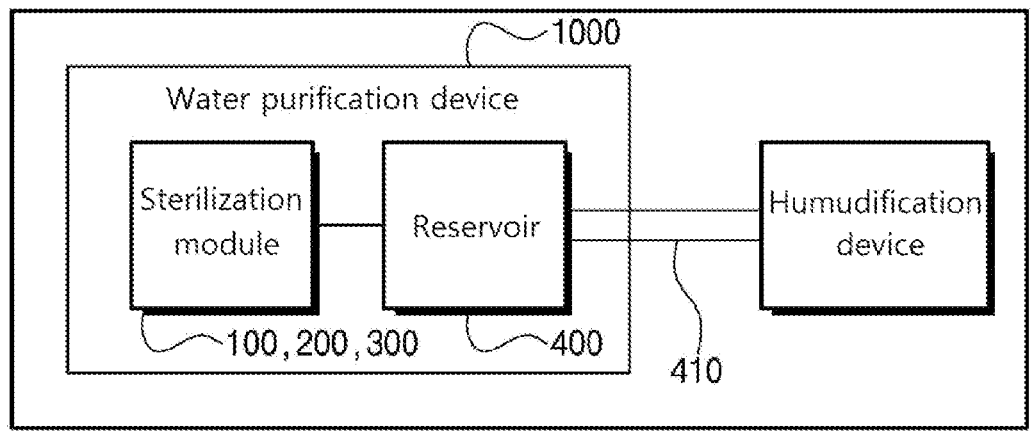
FIG. 40 is a block diagram illustrating a system including a water purification device according to another exemplary embodiment.

FIG. 40 is a block diagram illustrating a system 5000 including the water purification device 1000 according to another exemplary embodiment.

Referring to FIG. 40, the system 5000 including the water purification device 1000 may purify the water entered from the outside, through the water purification device 1000. At this time, the water purification device 1000 allows the sterilization module 100, 200, or 300 to sterilize the water entered to the reservoir 400 and to purify the water. The purified water flows from the water purification device 1000 to a humidification device 700 via the drain pipe 410. The purified water is converted into vapor by the humidification device 700, and then the vapor is discharged to the outside.

According to an exemplary embodiment, a system including a water purification device is described as an example of a cooling system and a humidification system. However, the type of system to which the system including the water purification device is applied is not limited thereto. The system including the water purification device according to an exemplary embodiment may be applied to any system using water.

Furthermore, the sterilization module 100, 200, or 300 according to an exemplary embodiment of the inventive concept, the water purification device 1000, and the system including the water purification device 1000 are exemplarily described purifying water. However, the inventive concepts are not limited thereto, and may be applied to a technology of sterilizing air, as well as water.

Figure 41:
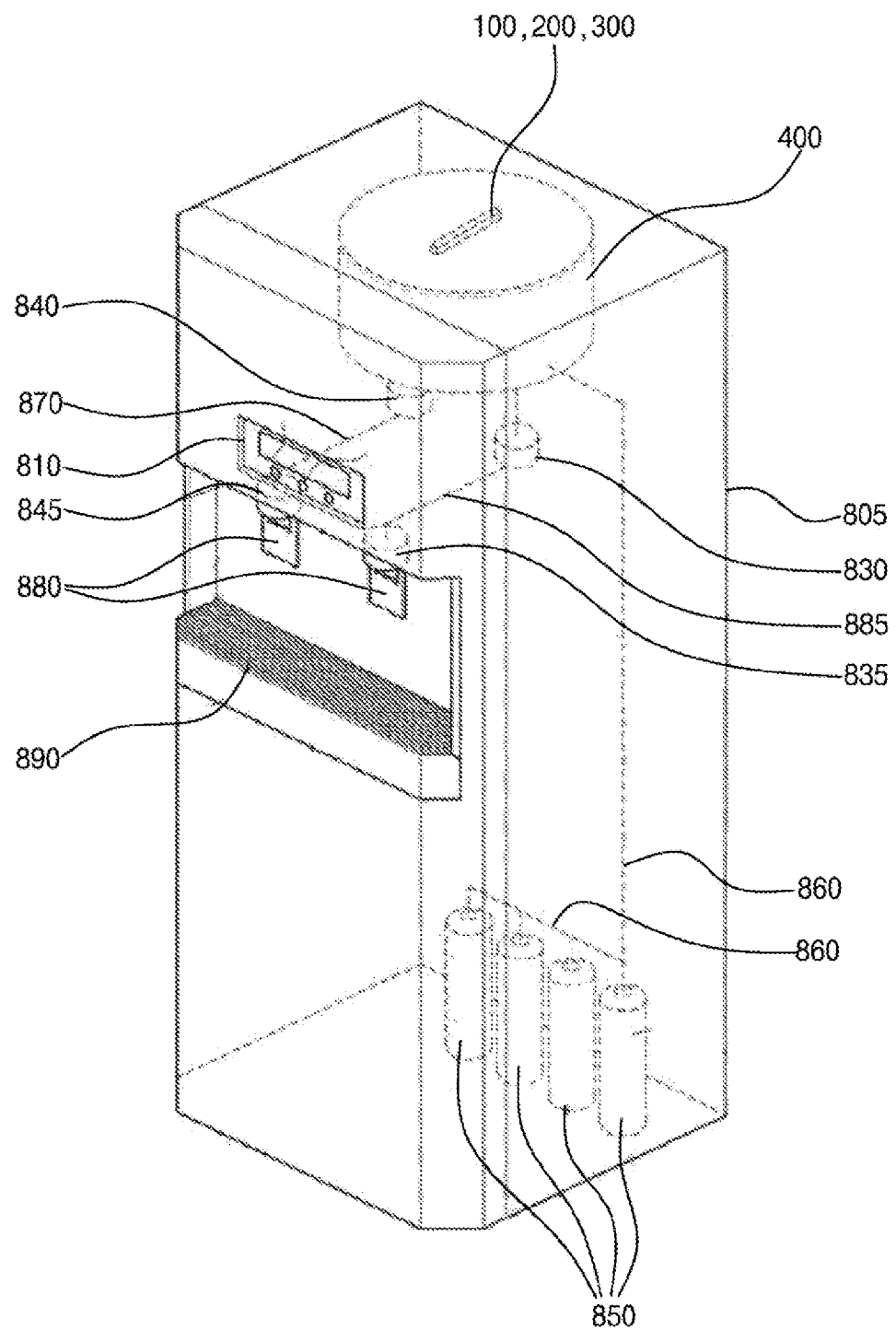
FIG. 41 is a perspective view of the water purification device of FIG. 38 according to an exemplary embodiment.

FIG. 41 is a perspective view of the water purification device of FIG. 38 in detail according to an exemplary embodiment.

A water purification device 6000 according to an exemplary embodiment includes a housing 805 that forms an exterior and protects and supports the internal structure. The housing 805 may be implemented to include a water supply part for supplying water to be purified to a water purification device, a filter part 850 for purifying the water supplied from the water supply part, a water purification supply pipe 860 for delivering the water purified by the filter part 850 to the reservoir 400, the sterilization module 100, 200, or 300 that includes a UV LED therein and emits UV light to the purified water, and a drain part for bringing the sterilized water in the reservoir 400 to the outside. The reservoir 400 is a reservoir where the water purified by the filter part 850 is stored. The reservoir 400 may be in various forms.

A display device 810 displaying the storage status and the sterilization time of the purified water is formed on the surface of the housing 805 forming the exterior. The display device 810 may further include a power button for turning on/off the power of the UV LED, a timer for providing UV light from the UV LED during the time specified by a user, and the like. Furthermore, the housing 805 may be implemented to further include a waterspout shelf 890 in the lower portion of the drain part for bringing the sterilized water to the outside.

The water purification device 6000 according to an exemplary embodiment includes a water supply part, into which tap water supplied from an external water purification plant is entered. The water supply part may include a water supply adjusting valve for controlling whether to supply the tap water. The water supply part is connected to the filter part 850, which purifies the tap water supplied from the water purification plant eight times, for example. The tap water supplied from the water supply part may be transferred to the filter part 850 via a tap water supply pipe. The filter part 850 may be implemented to include at least two or more filters. For example, the filters, such as one or more carbon filters or filters in the reverse osmosis scheme, are connected to the connection pipes so as to purify the water while moving the tap water. The water purified by moving the filter part 850 may be transferred to the reservoir 400. The purified water may be transferred to the reservoir 400 via the water purification supply pipe 860. The water purification supply pipe 860 may include an adjustment valve for adjusting the transfer of the purified water.

The sterilization module according to an exemplary embodiment may also be adapted to an air conditioning device.

Figure 42:
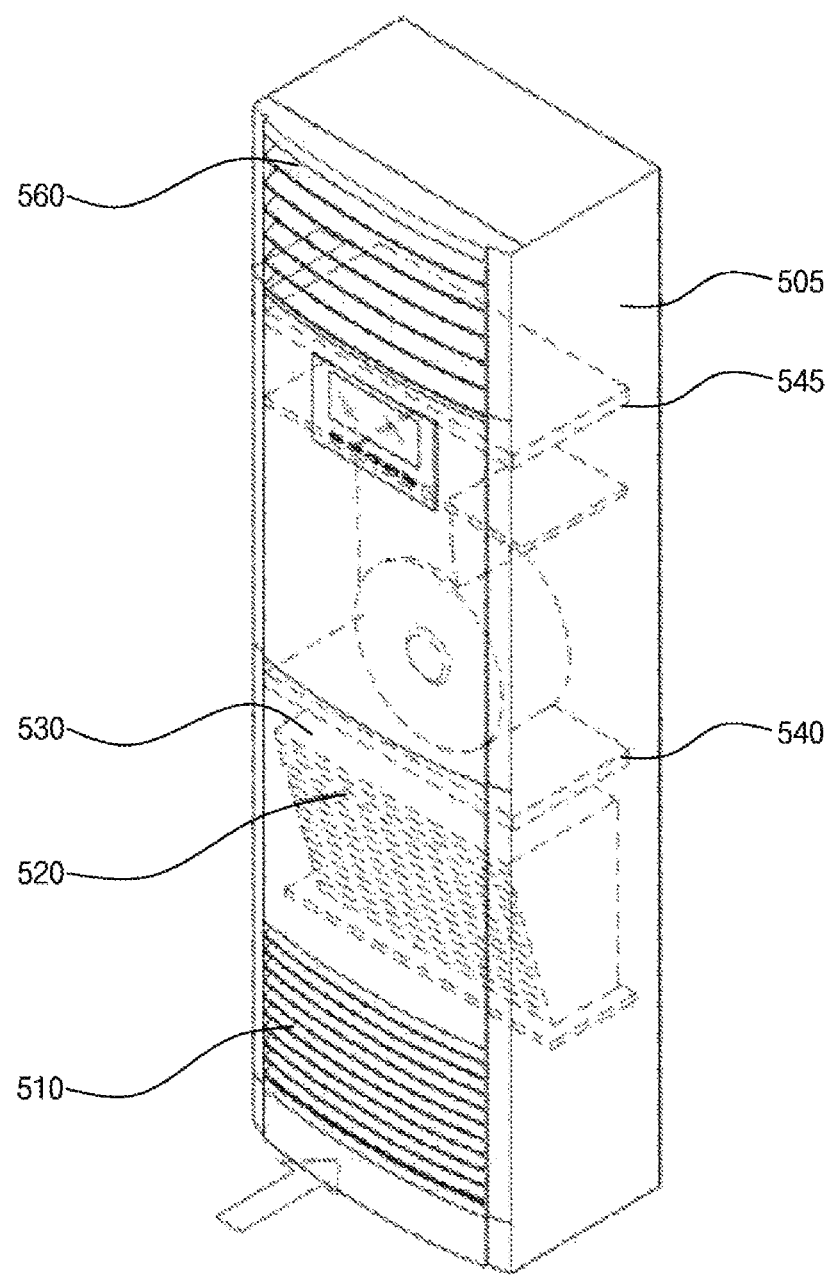
FIG. 42 is a view schematically illustrating an air conditioning device including a sterilization module.

FIG. 42 is a view schematically illustrating an air conditioning device 7000 including a sterilization module.

Referring to FIG. 42, the air conditioning device 7000 includes the body part 505 forming a frame and air purification modules 540 and 545 coupled to the body part 505. For example, the body part 505 may be an indoor unit of a standing-type air conditioner. The air purification modules 540 and 545 may include the first air purification module 540 and the second air purification module 545, which are classified depending on the location where the air purification module 540 or 545 is disposed inside the body part 505.

As illustrated in FIG. 42, the body part 505 may include an air inlet 510 disposed at the lower end of the body part 505, for the inflow of air. The air entered into the body part 505 via the air inlet 510 flows toward the upper portion, and fine particles are filtered through a filter 520. The air passing through the filter 520 is entered into an evaporator 530. The heat is exchanged in the evaporator 530, and then the air is vented at a state where the temperature is lowed. Next, the air is sterilized or deodorized while passing through the first air purification module 540. Then, the sterilized or deodorized air may flow to the upper portion through an air circulation device 550. For example, the air circulation device 550 may be a circulator. The air that flows to the upper portion by the air circulation device 550 may be re-sterilized or re-deodorized while passing through the second air purification module 545. Next, the re-sterilized or re-deodorized air is discharged outside the body part 505 via an air outlet 560 disposed at the upper end of the body part 505. As such, relatively high-temperature indoor air entered via the air inlet 510 is converted to the air in a low-temperature state via the evaporator 530, and may be sterilized or deodorized while passing through the first and second air purification modules 540 and 545. As such, the first air purification module 540 may be interposed between the evaporator 530 and the air circulation device 550, and the second air purification module 545 may be interposed between the air circulation device 550 and the air outlet 560.

In some exemplary embodiments, the air conditioning device may include only one of the first air purification module 540 and the second air purification module 545.

Each of the air purification modules 540 and 545 includes the sterilization module providing UV light. Because the configuration of the air purification module 540 or 545 is substantially the same as the configuration of the sterilization module 100, 200, or 300 described above, repeated descriptions thereof will be omitted to avoid redundancy. Herein, a plate having the shape substantially similar the shape of the reservoir cover may be provided to the sterilization module, and a sterilization module may be mounted on the plate in substantially the same way as the reservoir cover.

The sterilization module according to exemplary embodiments provides an improved sterilization efficiency and waterproof performance.

The inventive concepts described herein may be used in a sterilization module and a water purification device including the same. However, as described above, the sterilization module according to exemplary embodiments may be used for various devices, and not limited to the above-described exemplary embodiments.

Although certain exemplary embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

What is claims is:

1. A light emitting module, comprising:
   a light source configured to irradiate ultraviolet light;
   a board on which the light source is disposed;
   a tube accommodating the board and including a transparent region to transmit the ultraviolet light emitted from the light source;
   a first base coupled to one side of the tube;
   a second base coupled to the other side of the tube; and
   a fixation groove disposed in the tube and connected to at least one of the first and second bases,
   wherein the board is coupled to be inserted into the fixation groove, and
   wherein the fixation groove is spaced apart from a center of the first base when viewed in a cross-section perpendicular to a length direction of the tube.

2. The light emitting module of claim 1, wherein the board includes a light emitting surface on which the light source is disposed and a back surface opposite to the light emitting surface.

3. The light emitting module of claim 2, wherein the light emitting surface is spaced apart from the center of the first base.

4. The light emitting module of claim 2, wherein a longest distance between the light emitting surface and a first outer peripheral surface of the first base has a value different from a longest distance between the back surface and a second outer peripheral surface of the first base opposing the first outer peripheral surface.

5. The light emitting module of claim 1, further comprising a recess groove for accommodating a connector electrically connected to the light source, wherein the recess groove is spaced apart from the center of the first base.

6. The light emitting module of claim 1, wherein at least one of the first base and the second base includes a region contacting the tube.

7. The light emitting module of claim 1, wherein the fixation groove comprises:
a first fixation groove, into which one side surface of the board is to be inserted and fixed; and
a second fixation groove, into which other side surface of the board is to be inserted and fixed.

8. The light emitting module of claim 7, wherein:
the one side surface and the other side surface of the board are respectively connected to the first fixation groove and the second fixation groove; and
the board and an inner side surface of the first base are spaced apart by a predetermined distance.

9. A light emitting module, comprising:
a light source configured to irradiate ultraviolet light;
a board on which the light source is disposed;
a tube accommodating the board and including a transparent region to transmit the ultraviolet light emitted from the light source;
a first base coupled to one side of the tube;
a second base coupled to the other side of the tube; and
a fixation groove disposed in the tube and connected to at least one of the first and second bases,
wherein the board includes a light emitting surface and a back surface opposite to the light emitting surface,
wherein the board is coupled to be inserted into the fixation groove, and
wherein a longest distance between the light emitting surface and a first inner surface of the tube has a value different from a longest distance between the back surface and a second inner surface of the tube opposing the first inner surface.

10. The light emitting module of claim 9, wherein the fixation groove is spaced from a center of the tube when viewed in a cross-section perpendicular to a length direction of the tube.

11. The light emitting module of claim 9, wherein the light emitting surface is spaced apart from a center of the first base.

12. The light emitting module of claim 9, wherein a longest distance between the light emitting surface and a first outer peripheral surface of the first base has a value different from a longest distance between the back surface and a second outer peripheral surface of the first base opposing the first outer peripheral surface.

13. The light emitting module of claim 9, further comprising a recess groove for accommodating a connector electrically connected to the light source, wherein the recess groove is spaced apart from a center of the first base.

14. The light emitting module of claim 9, wherein the fixation groove comprises:
a first fixation groove, into which one side surface of the board is to be inserted and fixed; and
a second fixation groove, into which other side surface of the board is to be inserted and fixed.

15. The light emitting module of claim 14, wherein:
the one side surface and the other side surface of the board are respectively connected to the first fixation groove and the second fixation groove; and
the board and an inner side surface of the first base are spaced apart by a predetermined distance.

16. A light emitting module, comprising:
a board including a light emitting surface and a back surface opposite to the light emitting surface;
a light source disposed on the light emitting surface of the board and configured to irradiate light;
a tube accommodating the board and including a transparent region to transmit light emitted from the light source;
a first base coupled to one side of the tube;
a second base coupled to the other side of the tube; and
a fixation groove disposed in the tube and connected to at least one of the first and second bases,
wherein the board is coupled to be inserted into the fixation groove, and
wherein a longest distance between the light emitting surface and a first inner surface of the tube has a value different from a longest distance between the back surface and a second inner surface of the tube opposing the first inner surface.

17. The light emitting module of claim 16, wherein the fixation groove is spaced from a center of the tube when viewed in a cross-section perpendicular to a length direction of the tube.

18. The light emitting module of claim 16, wherein the first base includes a receiving groove through which external current is configured to be supplied, the receiving groove has a greater thickness than the fixation groove, and at least a portion of the receiving groove is disposed further away from a center of the tube than the fixation groove in a direction perpendicular to a length direction of the tube.

19. The light emitting module of claim 16, wherein the fixation groove comprises:
a first fixation groove, into which one side surface of the board is to be inserted and fixed; and
a second fixation groove, into which other side surface of the board is to be inserted and fixed.

20. The light emitting module of claim 19, wherein:
the one side surface and the other side surface of the board are respectively connected to the first fixation groove and the second fixation groove; and
the board and an inner side surface of the first or second base are spaced apart by a predetermined distance.

* * * * *